(12) United States Patent
Frenkel et al.

(10) Patent No.: US 7,534,913 B2
(45) Date of Patent: *May 19, 2009

(54) CRYSTALLINE FORM OF NATEGLINIDE

(75) Inventors: Gustavo Frenkel, Beer Sheva (IL); Boaz Gome, Rishon-Lezion (IL); Shlomit Wizel, Petah Tiqva (IL)

(73) Assignee: Teva Pharmaceutica Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/746,697

(22) Filed: Dec. 24, 2003

(65) Prior Publication Data

US 2005/0014836 A1  Jan. 20, 2005

Related U.S. Application Data

(63) Continuation-in-part of application No. 10/622,905, filed on Jul. 18, 2003, now Pat. No. 7,420,084, and a continuation-in-part of application No. 10/693,166, and a continuation-in-part of application No. PCT/US03/22375, filed on Jul. 18, 2003.

(60) Provisional application No. 60/396,904, filed on Jul. 18, 2002, provisional application No. 60/413,622, filed on Sep. 25, 2002, provisional application No. 60/423,750, filed on Nov. 5, 2002, provisional application No. 60/432,093, filed on Dec. 10, 2002, provisional application No. 60/432,962, filed on Dec. 12, 2002, provisional application No. 60/442,109, filed on Jan. 23, 2003, provisional application No. 60/449,791, filed on Feb. 24, 2003, provisional application No. 60/479,016, filed on Jun. 16, 2003.

(51) Int. Cl.
*C07C 229/00* (2006.01)
*A61K 31/195* (2006.01)
(52) U.S. Cl. ................................... 562/450; 514/563
(58) Field of Classification Search ................ 562/450; 514/563

See application file for complete search history.

(56) References Cited

U.S. PATENT DOCUMENTS

| 4,816,484 | A | 3/1989 | Toyoshima et al. |
| RE34,878 | E | 3/1995 | Toyoshima et al. |
| 5,463,116 | A | 10/1995 | Sumikawa et al. |
| 5,488,150 | A | 1/1996 | Sumikawa et al. |

(Continued)

FOREIGN PATENT DOCUMENTS

SK        200200360        7/2002

(Continued)

OTHER PUBLICATIONS

Harry G. Brittain, Polymorphism in Pharmaceutical Solids, 1999, Marcel Dekker ,Inc. (p. 236). p. 4.*

(Continued)

*Primary Examiner*—Taylor Victor Oh
(74) *Attorney, Agent, or Firm*—Kenyon & Kenyon LLP

(57) ABSTRACT

Provided are crystalline forms of nateglinide, labeled Forms A, C, D, F, G, I, J, K, L, M, N, O, P, Q, T, U, V, Y, α, β, γ, δ, ε, σ, θ and Ω, processes for their preparation and processes for preparation of other crystalline forms of nateglinide. Also provided are their pharmaceutical formulations and methods of administration.

36 Claims, 69 Drawing Sheets

FORM A

U.S. PATENT DOCUMENTS

| | | |
|---|---|---|
| 6,548,529 B1 | 4/2003 | Robl et al. |
| 6,555,519 B2 | 4/2003 | Washburn |
| 6,861,553 B2 * | 3/2005 | Yahalomi et al. ........... 562/450 |
| 2001/0044584 A1 | 11/2001 | Kensey |
| 2002/0032149 A1 | 3/2002 | Kensey |
| 2002/0061835 A1 | 5/2002 | Kensey |
| 2003/0069221 A1 | 4/2003 | Kosoglou et al. |
| 2003/0078517 A1 | 4/2003 | Kensey |
| 2004/0077725 A1 | 4/2004 | Reguri et al. |
| 2005/0014836 A1 | 1/2005 | Frenkel et al. |
| 2005/0090552 A1 * | 4/2005 | Yahalomi et al. ........... 514/563 |

FOREIGN PATENT DOCUMENTS

| | | |
|---|---|---|
| WO | WO 01/21159 | 3/2001 |
| WO | WO 02/32854 | 4/2002 |
| WO | WO 02/34254 | 5/2002 |
| WO | WO 02/34285 | 5/2002 |
| WO | WO 02/34713 | 5/2002 |
| WO | WO 02/40010 | 5/2002 |
| WO | WO 03/022251 | 3/2003 |
| WO | WO 03/076393 | 9/2003 |
| WO | WO 03/087038 | 10/2003 |
| WO | WO 03/087039 | 10/2003 |
| WO | WO 03/093222 | 11/2003 |
| WO | WO 2004/020396 | 3/2004 |

OTHER PUBLICATIONS

Hiroko Takesada et al., "Structure Determination of Metabolites Isolated from Urine and Bile after Administration of AY4166, a Novel $_D$-Phenylalanine-Derivative Hypoglycemic Agent," Bioorganic & Medicinal Chemistry, vol. 4, No. 10, 1996, pp. 1771-1781.

Hisashi Shinkai et al., "N-(Cyclohexylcartonyl)-D-phenylalanines and Related Compounds. A New Class of Oral Hypoglycemic Agents. 2," J. Med. Chem., vol. 32, 1989, pp. 1436-1441.

Xue-yan Zhu et al., "Study on Synthesis of Nateglinide," Hecheng Huaxue, vol. 9, No. 6, 2001, pp. 537-540.

Li Gang et al., "A New Crystal Form of Nateglinide," Acta Pharmaceutica Sinica, vol. 36, No. 7, 2001, pp. 532-534.

Li Gang et al., "Found a New Crystal Structure in Nateglinide by X-ray Powder Diffraction," Chinese Journal of Pharmaceutical Analysis, vol. 21, No. 5, 2001, pp. 342-344.

A nateglinide having the enclosed XRD (see fig. 17) was purchased before Jul. 3, 2002 in a foreign country from a supplier in another foreign country.

Terence L. Threlfall, "Analysis of Organic Polymorphs a Review," Analyst, vol. 120, Oct. 1995, pp. 2435-2460.

* cited by examiner

FORM A

FORM C

FORM D

FORM E

FORM F

FORM G

FORM I

FORM J

FORM K

FIG. 10 FORM L

FIG. 12 FORM N

FORM O

FORM P

FORM Q

FORM T

FORM U

FORM Y

FIG. 21 FORM α

FORM β

FIG. 23 FORM ρ

FORM δ

FORM ε

FORM ~ (σ)

FIG. 27 FORM φ

THERMAL STABILITY CHART

\* TRANSFORMATION MAY PROCEED THROUGH ANOTHER TERM.
\*\* THERMALLY STABLE AT LOWER HEATING TEMPERATURES (~50°C).
\*\*\* THERMALLY STABLE FORMS.
→ TRANSFORMATION AFTER STORAGE AT ROOM TEMPERATURE.
m MIXTURE WITH STARTING FORM.
\*\*\*\* WHEN STARTING MATERIAL CONTAINS SEEDS.
sol RESULTS MIGHT VARY DEPENDING ON THE SOLVATE OF FORM EPSILON USED.

FORM A

FORM D

FORM E

FORM I

FORM J

FORM K

FORM M

FORM N

FORM O

FORM P

FORM Q

FORM T

FIG. 51 FORM U

FORM V

FORM Y (CHLOROFORM SOLVATE)

FORM Y (DICHLOROMETHENE SOLVATE)

FORM α

FORM BETA

FORM DELTA

FORM EPSILON

FORM GAMMA

FORM SIGMA ~ (σ)

FORM THETA σ

Comparison between the impurity profile of Nateglinide crystallized in IPA-H₂O and Nateglinide in Methanol-H₂O

| Sample No | Solvent | Impurity profile by RRT [% w/w] | | | | | |
|---|---|---|---|---|---|---|---|
| | | D-PA (0.23) | (0.25) | (0.46) | (0.80) | Ipcha (0.89) | Dimer (1.38) | Methyl Ester (1.51) | Isopropyl Ester (2.3) |
| RL-2155/1 | Methanol-H₂O | <0.01 | | | 0.02 | 0.03 | 0.02 | 2.91 | |
| RL-2163/4 | IPA-H₂O | <0.01 | 0.04 | | | 0.02 | 0.01 | 0.03 | 0.02 |

Note: D-PA means D-Phenyl Alanine
Ipcha means Iso propyl cyclohexyl carboxylic acid
Both are the starting materials of the product (-)-N-[(trans-4-isopropyl cyclohexane)carbonyl]-D-phenylalanine

FIG. 64

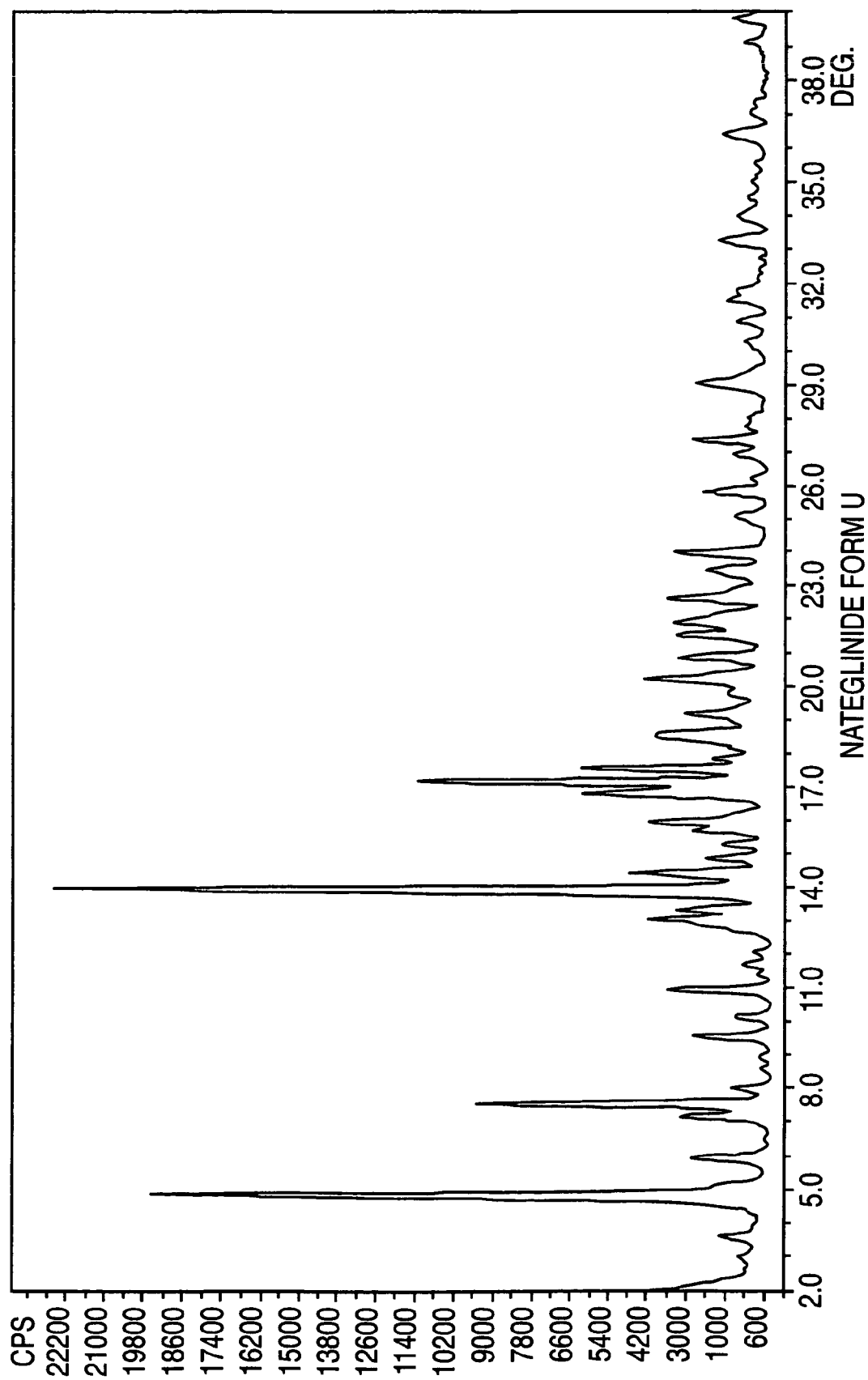

CRYSTALLINE FORM OF NATEGLINIDE

CROSS-REFERENCE TO RELATED APPLICATIONS

This application is a continuation-in-part of U.S. patent applications Ser. No. 10/622,905, filed Jul. 18, 2003; Ser. No. 10/693,166, filed Oct. 23, 2003 and International Application No. PCT/US03/22375, filed Jul. 18, 2003, and claims the benefit of U.S. Provisional Applications Ser. No. 60/442,109, filed Jan. 23, 2003; Ser. No. 60/449,791, filed Feb. 24, 2003 and Ser. No. 60/479,016, filed Jun. 16, 2003, the contents of all of which are incorporated herein by reference. U.S. patent application Ser. No. 10/693,166 is a continuation of U.S. patent application Ser. No. 10/622,905, and claims the benefit of the following U.S. Provisional Applications: Ser. No. 60/396,904, filed Jul. 18, 2002; Ser. No. 60/413,622, filed Sep. 25, 2002; Ser. No. 60/414,199, filed Sep. 26, 2002; Ser. No. 60/423,750, filed Nov. 5, 2002; Ser. No. 60/432,093, filed Dec. 10, 2002: Ser. No. 60/432,962, filed Dec. 12, 2002; Ser. No. 60/442,109, filed Jan. 23, 2003; Ser. No. 60/449,791, filed Feb. 24, 2003; and Ser. No. 60/479,016, filed Jun. 16, 2003.

FIELD OF THE INVENTION

The present invention relates to the solid state chemistry of nateglinide.

BACKGROUND OF THE INVENTION

Nateglinide, known as (−)-N-(trans-4-isopropylcyclohexanecarbonyl)-D-Phenylalanine, has the following structure and characteristics:

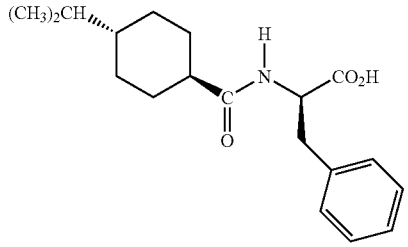

Formula         $C_{19}H_{27}NO_3$
Molecular Weight  317.42
Exact Mass        317.199093
Composition       C 71.89% H 8.57% N 4.41% O 15.12%

Nateglinide is marketed as STARLIX, which is prescribed as oral tablets having a dosage of 60 mg and 120 mg for the treatment of type II diabetes. STARLIX may be used as monotherapy or in combination with metaformin to stimulate the pancreas to secrete insulin. According to the maker of STARLIX, nateglinide is a white powder that is freely soluble in methanol, ethanol, and chloroform, soluble in ether, sparingly soluble in acetonitrile and octanol, and practically insoluble in water.

Nateglinide may be crystallized out of a mixture of water and methanol, and further dried, as disclosed in U.S. Pat. No. 4,816,484. The procedure of the '484 patent results in a hydrate labeled by the present Applicant(s) as Form Z, or in a methanolate labelled by the Applicant(s) as Form E. Drying of the wet sample results in Form B.

The present invention relates to the solid state physical properties of nateglinide. These properties may be influenced by controlling the conditions under which nateglinide is obtained in solid Form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid may have therapeutic consequences since it imposes an upper limit on the rate at which an orally-administered active ingredient may reach the patient's bloodstream. The rate of dissolution is also a consideration in formulating syrups, elixirs and other liquid medicaments. The solid state Form of a compound may also affect its behavior on compaction and its storage stability.

These practical physical characteristics are influenced by the conformation and orientation of molecules in the unit cell, which defines a particular polymorphic Form of a substance. The polymorphic Form may give rise to thermal behavior different from that of the amorphous material or another polymorphic Form. Thermal behavior is measured in the laboratory by such techniques as capillary melting point, thermogravimetric analysis (TGA) and differential scanning calorimetry (DSC) and may be used to distinguish some polymorphic forms from others. A particular polymorphic Form may also give rise to distinct spectroscopic properties that may be detectable by powder X-ray crystallography, solid state C NMR spectrometry and infrared spectrometry.

Nateglinide exists in various crystalline forms. U.S. Pat. Nos. 5,463,116 and 5,488,150 disclose two crystal forms of nateglinide, designated B-type and H-type, and processes for their preparation. These patents are incorporated herein by reference for their disclosure of the forms. Both forms are characterized by melting point, X-Ray Powder Diffraction ("XRPD") pattern, IR spectrum in KBr and DSC thermogram. According to these patents, B-type has a melting point of 129-130° C. while H-type has a melting point of 136-142° C. The H-type crystals are characterized in these patents by an XRPD pattern with peaks at 8.1, 13.1, 19.6 and 19.9±0.2 degrees 2θ, and a strong reflection between 15 and 17±0.2 degrees 2θ. The B-type crystal is reported to lack these peaks and have a weak reflection between 15 and 17±0.2 degrees 2θ. H-type crystals are reported to have an IR spectrum with characteristic absorptions at about 1714, 1649, 1542 and 1214cm$^{-1}$. These absorptions are reported to be missing in the spectrum of B-type crystals.

According to U.S. Pat. No. 5,463,116, B-type crystals are unstable and susceptible to change during grinding as demonstrated by DSC. The DSC thermogram of B-type shows a sharp endotherm at 131.4° C. before grinding while that of H-type shows a sharp endotherm at 140.3° C. After grinding, the DSC thermogram of B-type shows a second endotherm at 138.2° C., suggesting a solid-solid transformation during grinding.

According to U.S. Pat. No. 5,463,116, the temperature during crystallization and filtration determines whether the crystal Form is B-type or H-type. Temperatures above 10° C., more preferably above 15° C., lead to formation of H-type, while those below 10° C. lead to formation of B-type.

Another crystalline form of nateglinide designated Type-S is disclosed in two Chinese articles: ACTA Pharm. Sinica 2001, 36(7), 532-34 and Yaowu Fenxi Zazhi, 2001, 21(5), 342-44. Form S is reported to be distinguisheable from Forms B and H by a melting point of 172.0° C., a Fourier Transform IR with a peak at 3283 cm$^{-1}$ (as supposed to 3257 cm$^{-1}$ and 3306 cm$^{1-}$for Forms B and H respectively) and an XRPD pattern with a strong peak at 3.78±0.2 degrees 2θ.

U.S. Pat. No. 5,463,116 ("the '116 patent") lists the methanolate, ethanolate, isopropanolate and acetonitrilate solvates of nateglinide. According to the '116 patent, amorphous nateglinide may be obtained by drying the hydrate and the solvates. The hydrate may be crystallized by dissolving B-type crystals in a 1.5:1 mixture of ethanol and water, followed-by crystallization, as disclosed in Example B-3 of the '116 patent.

The present Applicants obtained a hydrate of nateglinide which the Applicants labeled as Form Z. However, repeating of Example B-3 or comparative Example A3 of the '116 patent also results in Form Z, as well as the crystallization procedure of the '484 patent. Form Z is obtained when only water is present, but Form E methanolate or ethanolate when both methanol or ethanol and water are present.

WO 02/34713, a PCT publication in Japanese, provides in its abstract: "A process for preparing B form nateglinide crystals containing substantially no H-form crystals, which comprises the step of drying wet crystals of a nateglinide solvate at a low temperature until the solvent disappears and then causing them to undergo a crystal transition." According to the Applicant's translation of Example 1 of the WO publication: "Nateglinide H-form crystals (24.5 kg) were added to ethanol (360 L) and stirred to dissolution at room temperature. After dissolution was confirmed (the mixture) was cooled to 5° C. and allowed to mature at 5° C. for one hour. The deposited crystals were separated and damp crystals (43.0 kg) obtained. These were dried at 45° C. in a rack drier for 24 hours (water content ca. 1%) and then heated for 12 hours at 90° C. to bring about a crystal transformation, when dry crystals (13.3 kg) were obtained. When these crystals were measured by DSC, the characteristic B-form peak was detected (mp ca. 130° C.) but the characteristic H-form peak (mp ca. 139° C.) was not detected. Hence the crystals obtained were of the B-form only and the H-form was concluded to be essentially absent."

According to the Applicants' translation of Page 3, Line 2 of the WO publication: "The moist solvate crystals obtained (BS: from the cooled solution) are dried till the solvent disappears. The temperature for this will differ depending on the type and quantity of solvent, but usually lies below 60° C. and preferably below 50° C. Although there is no lower limit to the temperature, [the drying] is usually carried out at 20° C. or more for economic reasons. Drying is favorably carried out at usual reduced pressure; at industrially attainable reduced pressures the drying will be complete in a short time. Though the drying at low temperature can be continued to virtual disappearance of the solvent it is not necessary to clear it completely. Even if solvent to the extent of 5% by weight is present this is no problem because it will disappear during the crystal transformation. By heating the dried crystals at 60-110° C., preferably 70-100° C., a crystal transformation into the B-form is brought about. Though the crystal transformation is usually favorably carried out in 0.5 to 48 hours, a period of 1-24 hours is most favored."

Another PCT publication, WO 03/022251 discloses a crystalline form of nateglinide labeled "AL-type". The crystalline form is characterized as having a melting point of 174-178° C., an XRPD pattern with peaks at 7.5, 15.5, 19.8 and 20.2 degrees 2θ, and an infra red spectrum with absorption bands in the region 1711.5, 1646.5, 1538.7, 1238.8, 1215.1 and 700.5 cm$^{-1}$. The crystalline form is obtained in the examples from a solution of acetonitrile under a specific temperature range.

Processes for preparation of nateglinide are disclosed in WO/0232854.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. New polymorphic forms of nateglinide have now been discovered.

SUMMARY OF THE INVENTION

The present invention provides for 26 crystalline forms of nateglinide, denominated Forms A, C, D, F, G, I, J, K, L, M, N, O, P, Q, T, U, V, Y, α (alpha), β (beta), γ (gamma), δ (delta), ε (epsilon), σ (sigma), θ (theta) and Ω (omega).

Some of these crystalline forms have bound solvents, that is solvents that are part of the crystalline structure (solvates). These solvates having bound solvent include Form A (xylene), C (dimethylacetamide-"DMA"), D (ethanol-"EtOH"), E (ethanol and methanol-"MeOH"), F (n-propanol-"n-PrOH"), G (isopropyl alcohol-"IPA"), I (n-butanol-"n-BuOH"), J (N-methylpyrrolidone-"NMP"), K (dimethylformamide-"DMF"), M (carbon tetrachloride-"CTC"), N (dichloroethane-"DCE"), O (methanol), Q (chloroform-"CHCl$_3$"), T (methanol), V (dimethoxyethane-"DME"), Y (chloroform; dichloromethane), β (N-methyl pyrolidone), γ (N-methylpyrrolidone) and ε (acetone; acetonitrile-"MeCN"; nitromethane-"NM") and θ (heptane). Form Z is a hydrate, having water in the crystalline structure. Form Ω is a solvate of both water and isopropyl alcohol.

Other crystalline forms do not have bound solvents, i.e., less than about 2% as measured by loss on drying ("LOD"), and are anhydrates. These anhydrates include crystalline Forms L, P, U, α, δ and σ.

The XRPD pattern of these forms as substantially depicted is disclosed in FIGS. 1-27 and 63, with the characteristic peaks listed in Table I. The DSC thermograms for the forms is disclosed in FIGS. 36 to 62, and the characteristic DSC peaks are listed in Table II. The FTIR spectrum of the anhydrate and hydrate Forms and their characteristic peaks are also provided. The LOD values from the TGA analysis of some of these Forms is listed in Table III. Preparation of the various Forms by crystallization procedure is listed in Table IV, while preparation by trituration is listed in Tables V and VI, data on absorption of solvent vapors is listed in Table VII, data on preparation by solvent removal is listed in Table VIII and data on crystallization from a solvent/anti-solvent system is listed in Tables IX-XI. FIG. 28 summarizes the thermal stability of the various forms.

The present invention also provides for pharmaceutical formulations of the various crystalline forms and their administration.

BRIEF DESCRIPTION OF THE FIGURES

FIG. 64 is a determination of purity of Form B prepared by Example 15.

FIG. 69 is an XRPD pattern of pure Form U, lacking the impurity at 3.8 +/−0.2 shown in FIG. 17, prepared according to the refined processes disclosed in the specification.

DETAILED DESCRIPTION OF THE INVENTION

In one aspect, the present invention provides for 26 crystalline forms of nateglinide ("NTG"), denominated Form A, C, D, F, G, I, J, K, L, M, N, O, P, Q, T, U, V, Y, α, β, γ, δ, ε, σ, θ and Ω. These crystalline forms are characterized by their XRPD pattern, DSC thermogram and TGA analysis, among others. Also provided are processes for preparation of other polymorphic forms such as Form B, E, H, S and Z.

The various crystalline forms are characterized by their XRPD pattern, which differs from one polymorph to another. Form E is rather similar by XRPD to Form Z, although some differences may be observed. The peak at 3.7 is characteristic of Form E and is not observed in the XRPD of Form Z. The pattern in the range of 19-22 degrees two theta is also somewhat different between these two forms. Table I lists the most characteristic peaks for the new crystalline forms. The XRPD patterns are illustrated in FIGS. 1-27 and 63.

TABLE I

XRPD characteristic peaks for the nateglinide crystalline forms

| Crystal Form | Characteristic XRD peaks- Within about ±0.2 degrees two theta |
|---|---|
| A | 6.6, 13.3, 13.9, 16.8, 27.2, 28.0 (FIG. 1) |
| C | 5.2, 8.2, 8.8 (FIG. 2) |
| D | 6.6, 7.5, 13.1, 16.5, 17.4, 21.1 (FIG. 3) |
| E | 3.7, 4.6, 14.9, 15.6, 16.1 (FIG. 4) |
| F | 4.8, 5.3, 15.2, 18.9, 19.6 (FIG. 5) |
| G | 14.4, 15.3, 19.3, 20.3 (FIG. 6) |
| I | 5.5, 7.4, 16.8 (FIG. 7) |
| J | 8.0, 11.2, 12.0, 15.9, 16.1, 17.7, 28.1 (FIG. 8) |
| K | 9.5, 15.4, 17.1, 21.2 (FIG. 9) |
| L | 17.6, 17.9, 19.6 (FIG. 10) |
| M | 16.2, 16.4, 17.0, 17.8, 18.6, 19.4, 19.6 (FIG. 11) |
| N | 5.3, 5.5, 8.9, 9.9, 20.4, 21.1 (FIG. 12) |
| O | 4.4, 5.2, 15.7, 16.6 (FIG. 13) |
| P | 4.0, 4.6, 13.4, 13.9, 19.1 (FIG. 14) |
| Q | 5.1, 5.6, 16.2, 19.8 (FIG. 15) |
| T | 7.2, 7.9, 8.3, 10.7 (FIG. 16) |
| U | 4.7, 7.4, 13.8, 17.0 (FIG. 17) |
| V | 4.5, 5.8, 11.4, 16.4 (FIG. 18) |
| Y | 6.1, 14.2, 15.1, 18.7 (FIG. 19) |
| Z | 4.7, 5.3, 13.5, 13.9, 15.1, 15.7, 16.1, 18.7, 19.5, 21.5 (FIG. 20) |
| α | 4.8, 5.1, 19.0, 19.4, 27.7, 28.9, 31.2 (FIG. 21) |
| β | 4.6, 9.4, 13.9, 18.8 (FIG. 22) |
| γ | 4.4, 8.9, 18.4, 18.8, 19.5 (FIG. 23) |
| δ | 5.6 14.5, 18.2, 18.9, 19.5 (FIG. 24) |
| ε | 4.2, 13.0, 13.6, 14.3, 16.2, 16.7, 19.6 (FIG. 25) |
| θ | 4.8, 7.8, 15.5, 17.7 (FIG. 26) |
| σ | 5.5, 6.1, 6.7, 14.3 (FIG. 27) |
| Ω | 4.5, 7.8, 15.5, 16.9, 17.8, 19.2, 19.7 (FIG. 63) |

The various crystalline forms of nateglinide are also characterized by their DSC thermograms. Table II lists the DSC peaks (endotherms). In addition to the peaks listed in Table II, many of the various crystalline forms show an exotherm at about 165° C. followed by an endotherm at about 174° C., probably due to recrystallization into S-Type Form.

TABLE II

DSC peaks of the nateglinide crystalline forms

Figure 36:
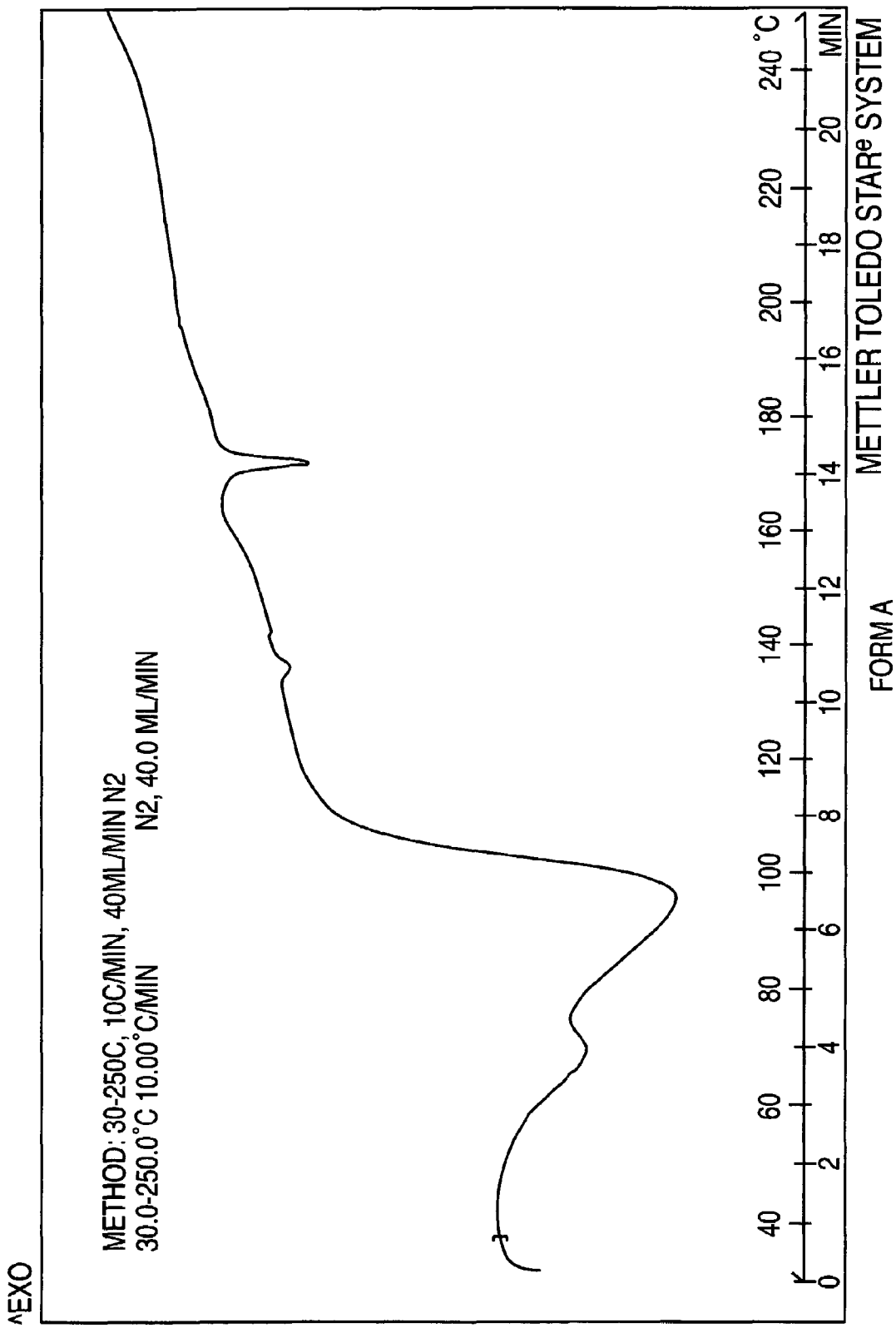
FIG. 36 is a DSC thermogram of nateglinide Form A.
Figure 37:
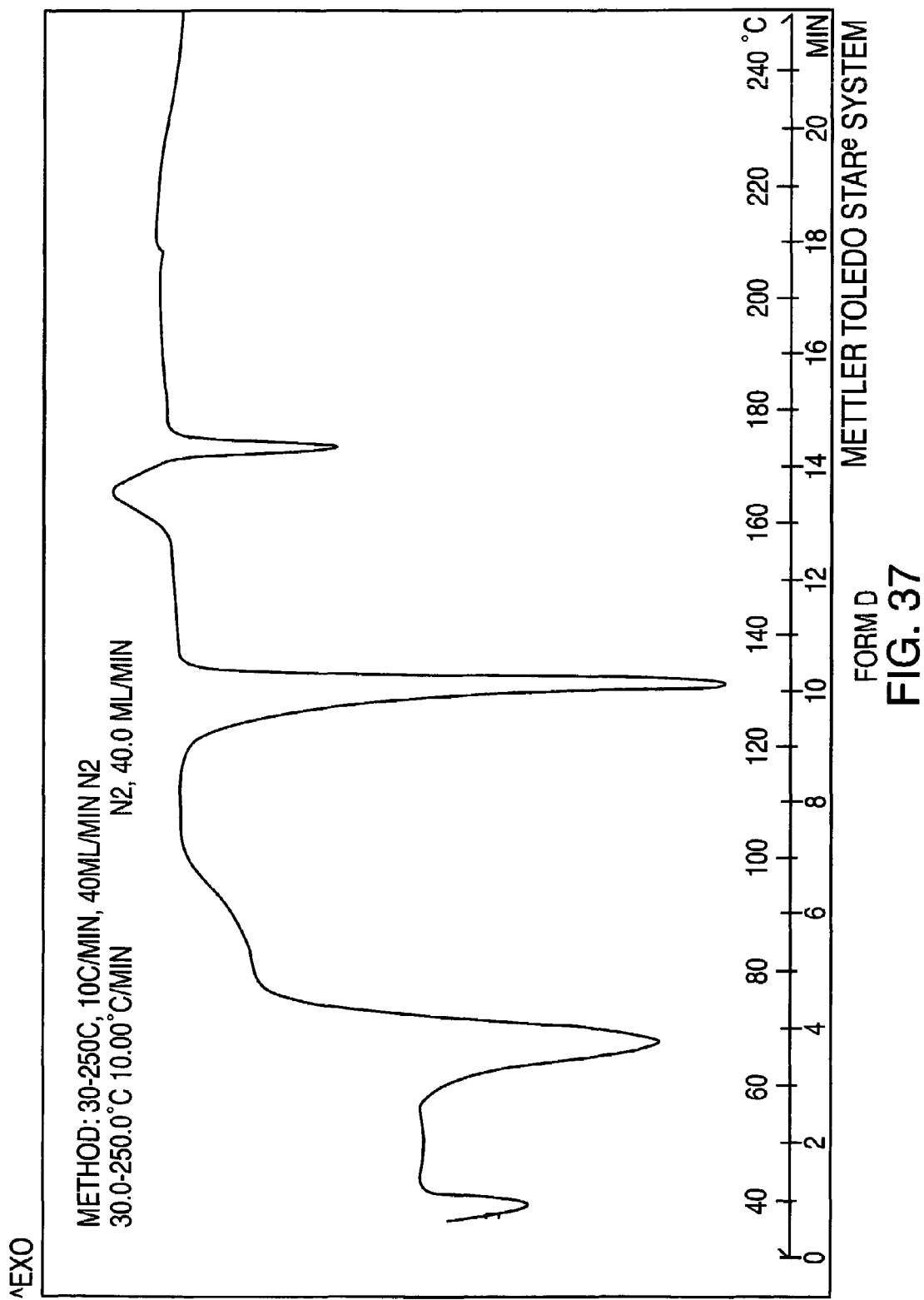
FIG. 37 is a DSC thermogram of nateglinide Form D.
Figure 38:
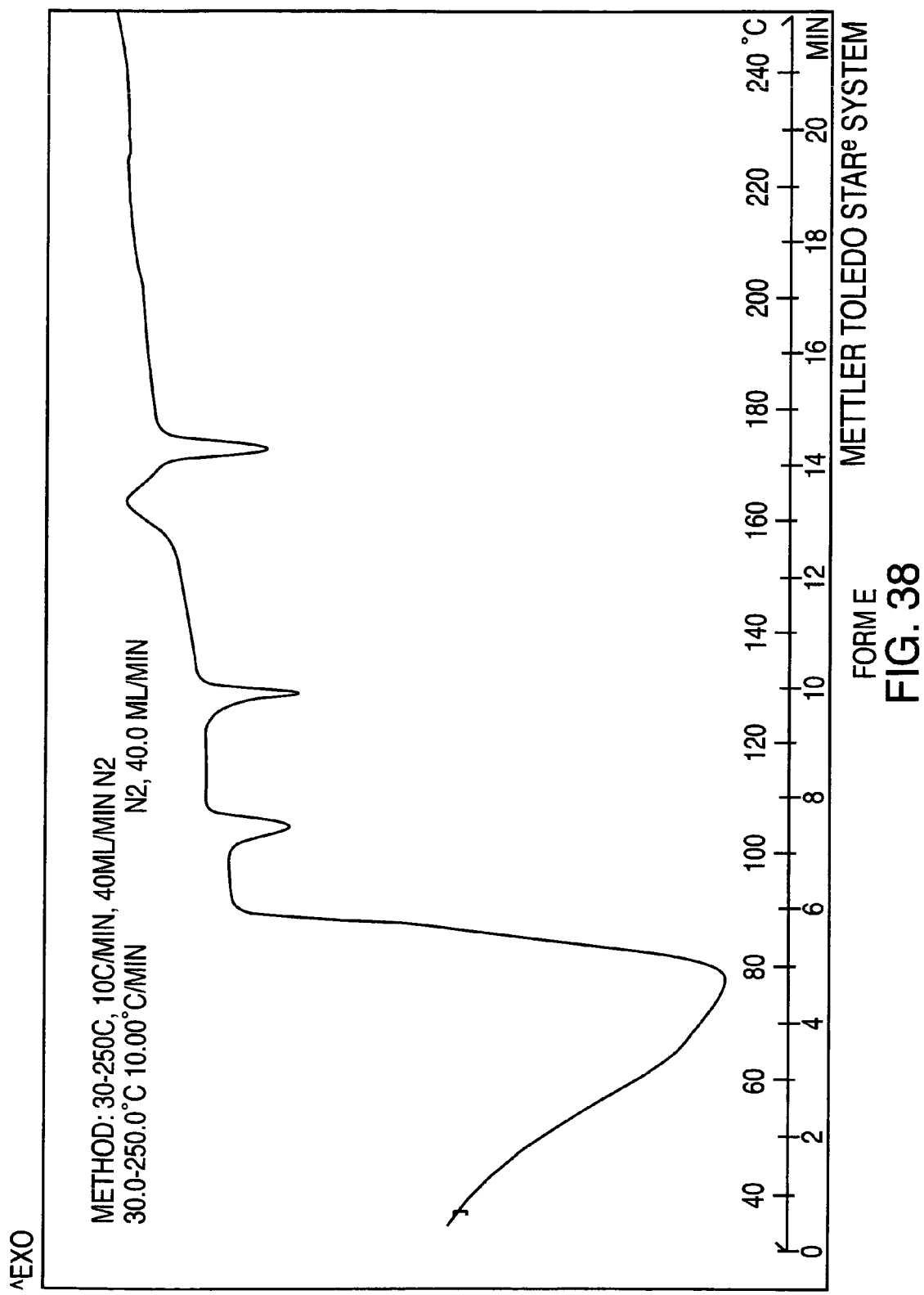
FIG. 38 is a DSC thermogram of nateglinide Form E.
Figure 39:
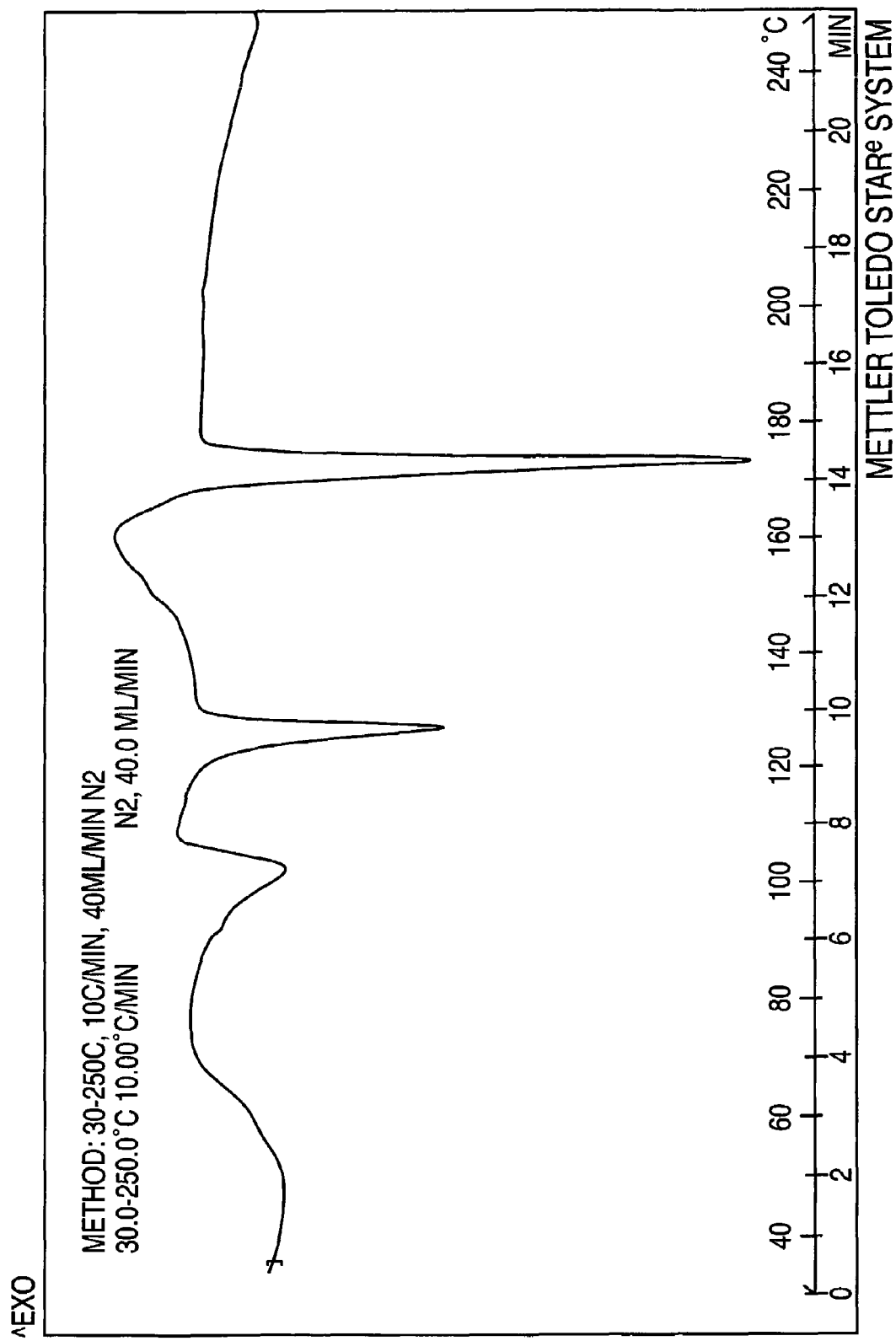
FIG. 39 is a DSC thermogram of nateglinide Form F.
Figure 40:
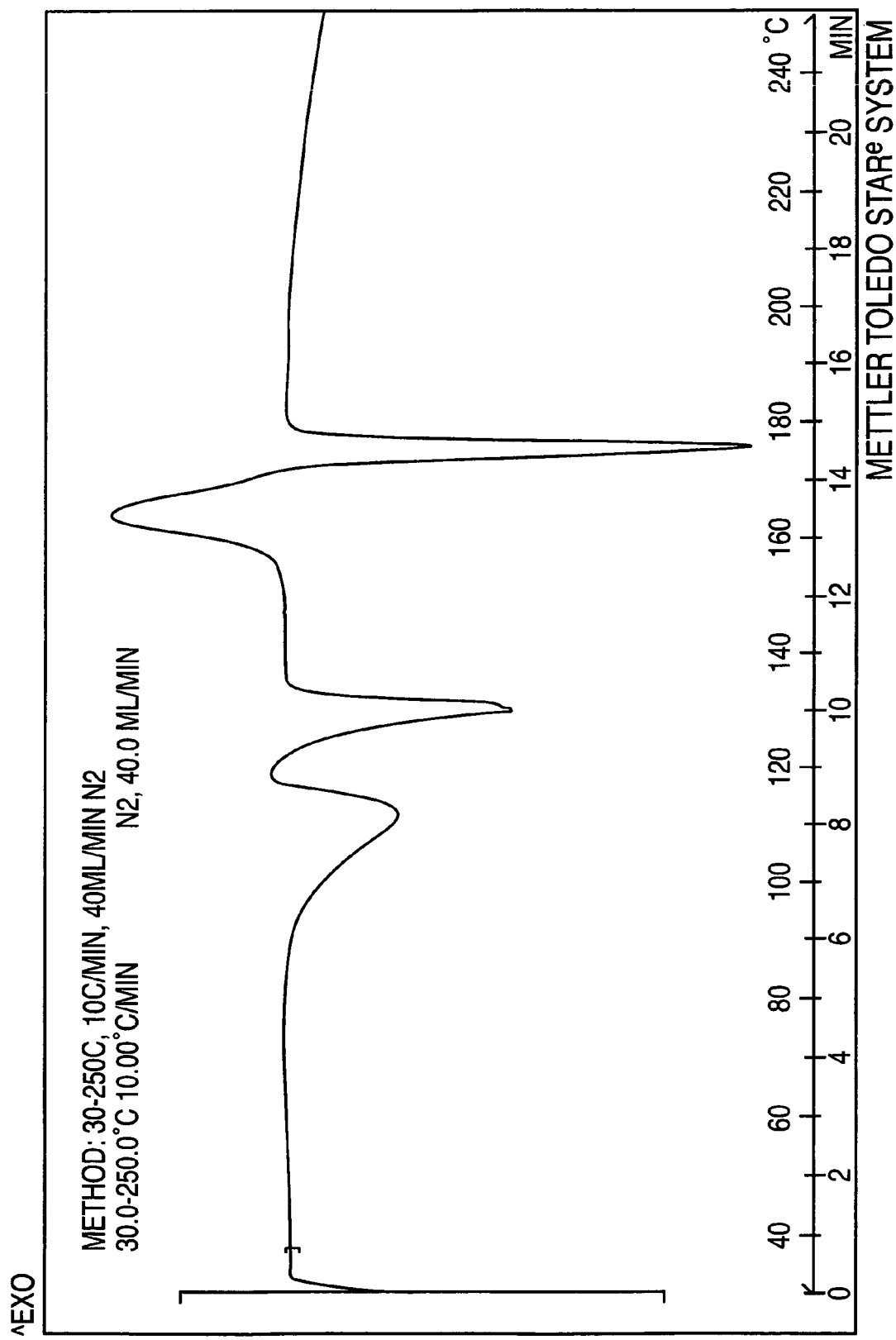
FIG. 40 is a DSC thermogram of nateglinide Form G.
Figure 41:
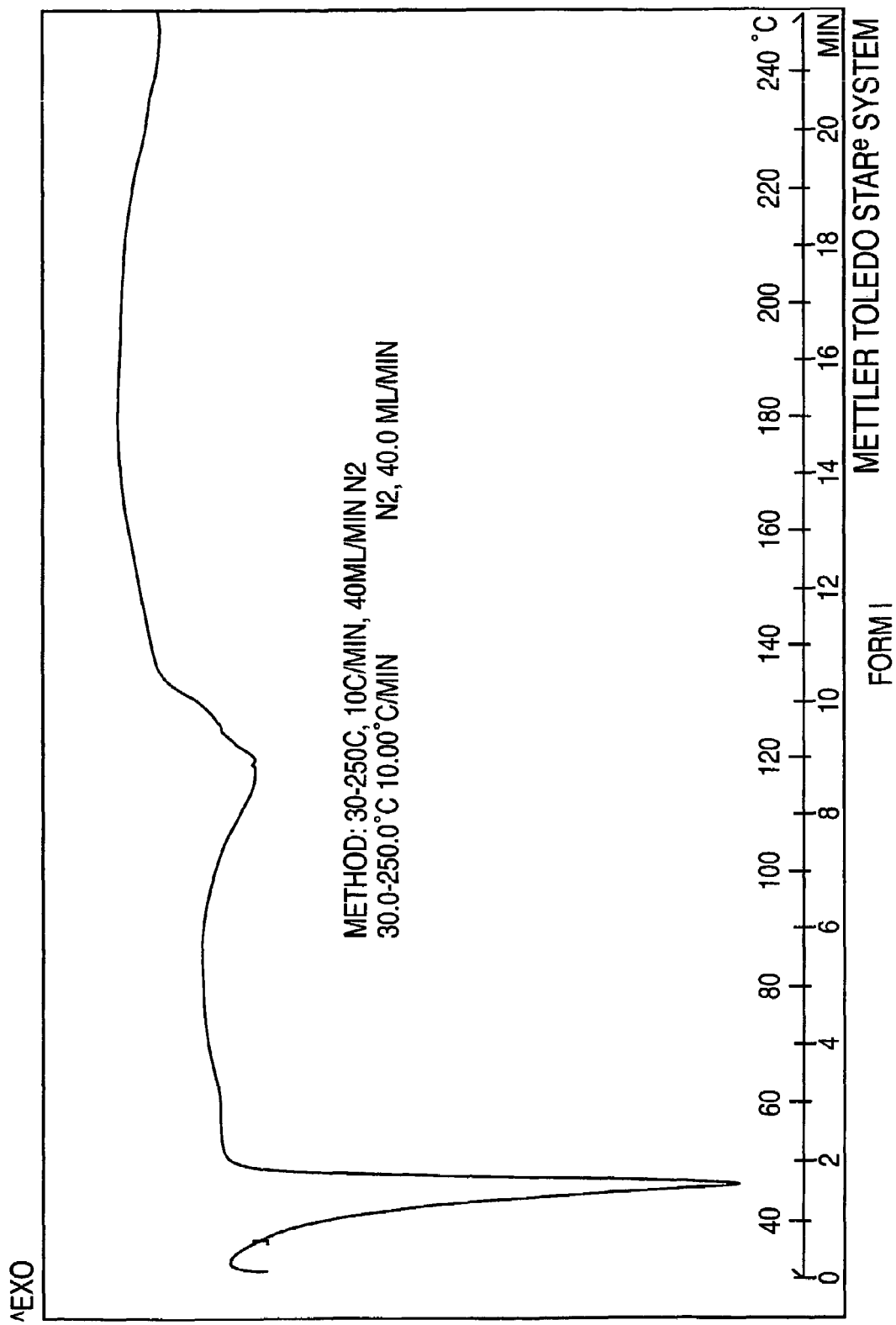
FIG. 41 is a DSC thermogram of nateglinide Form I.
Figure 42:
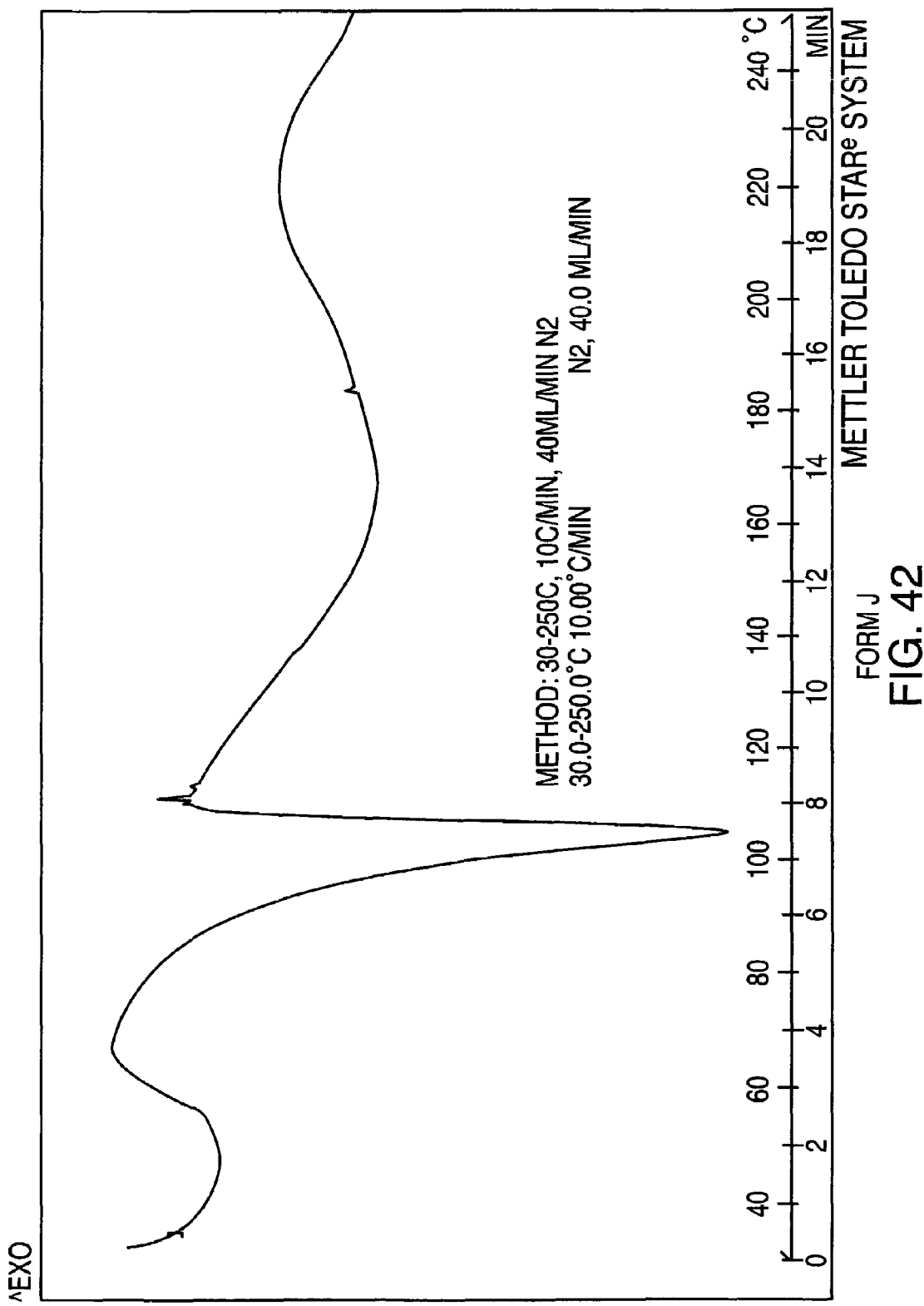
FIG. 42 is a DSC thermogram of nateglinide Form J.
Figure 43:
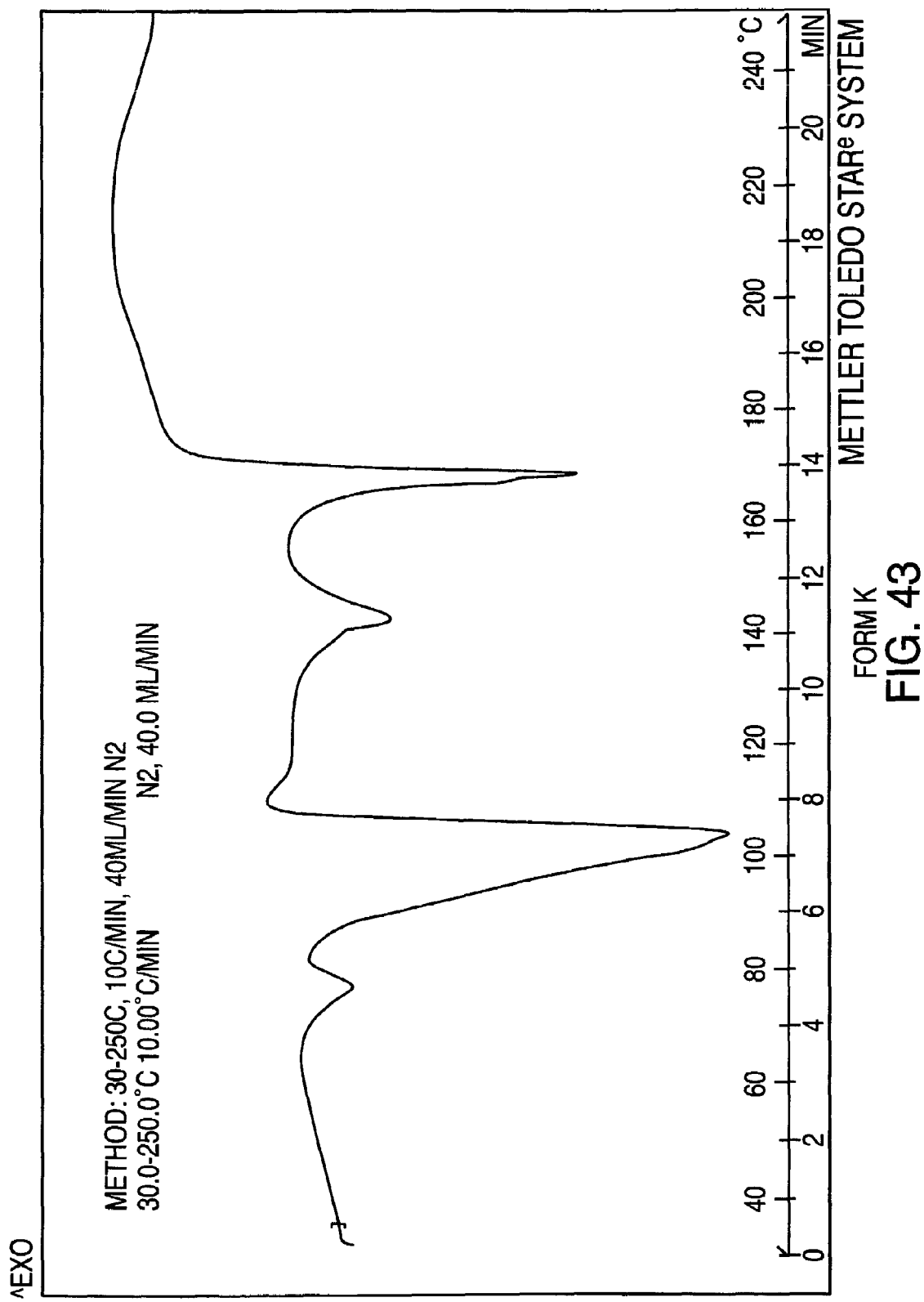
FIG. 43 is a DSC thermogram of nateglinide Form K.
Figure 44:
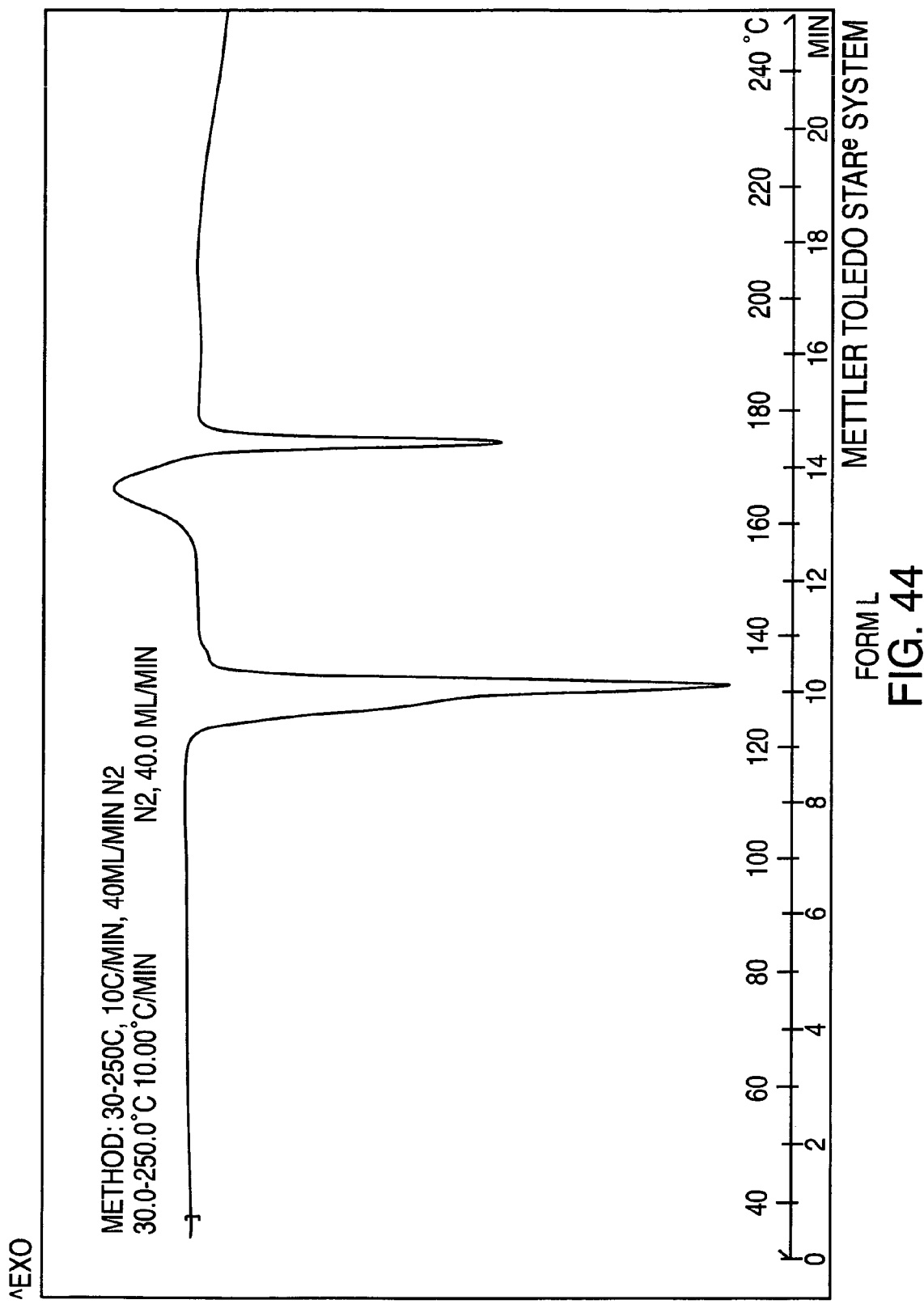
FIG. 44 is a DSC thermogram of nateglinide Form L.
Figure 45:
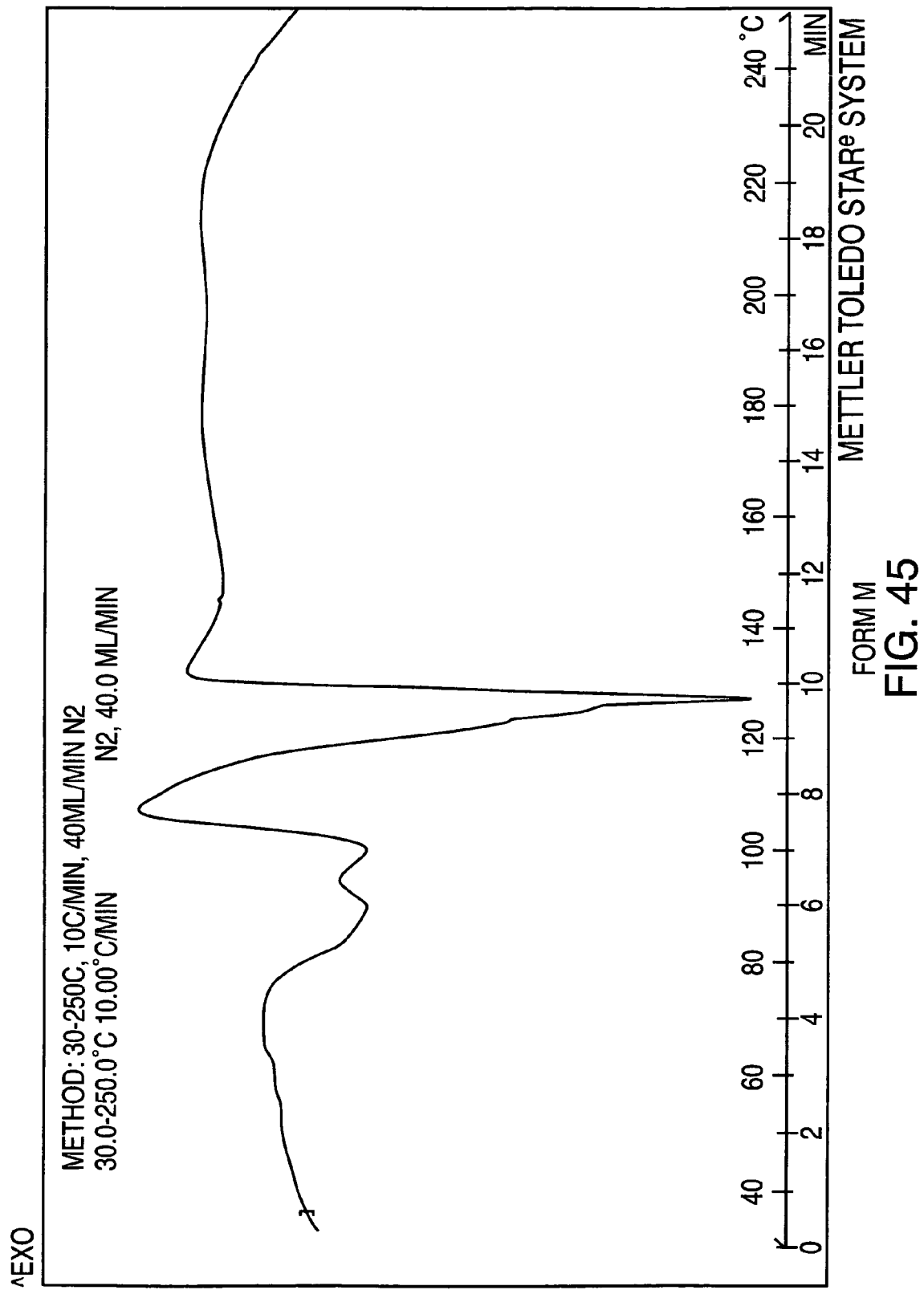
FIG. 45 is a DSC thermogram of nateglinide Form M.
Figure 46:
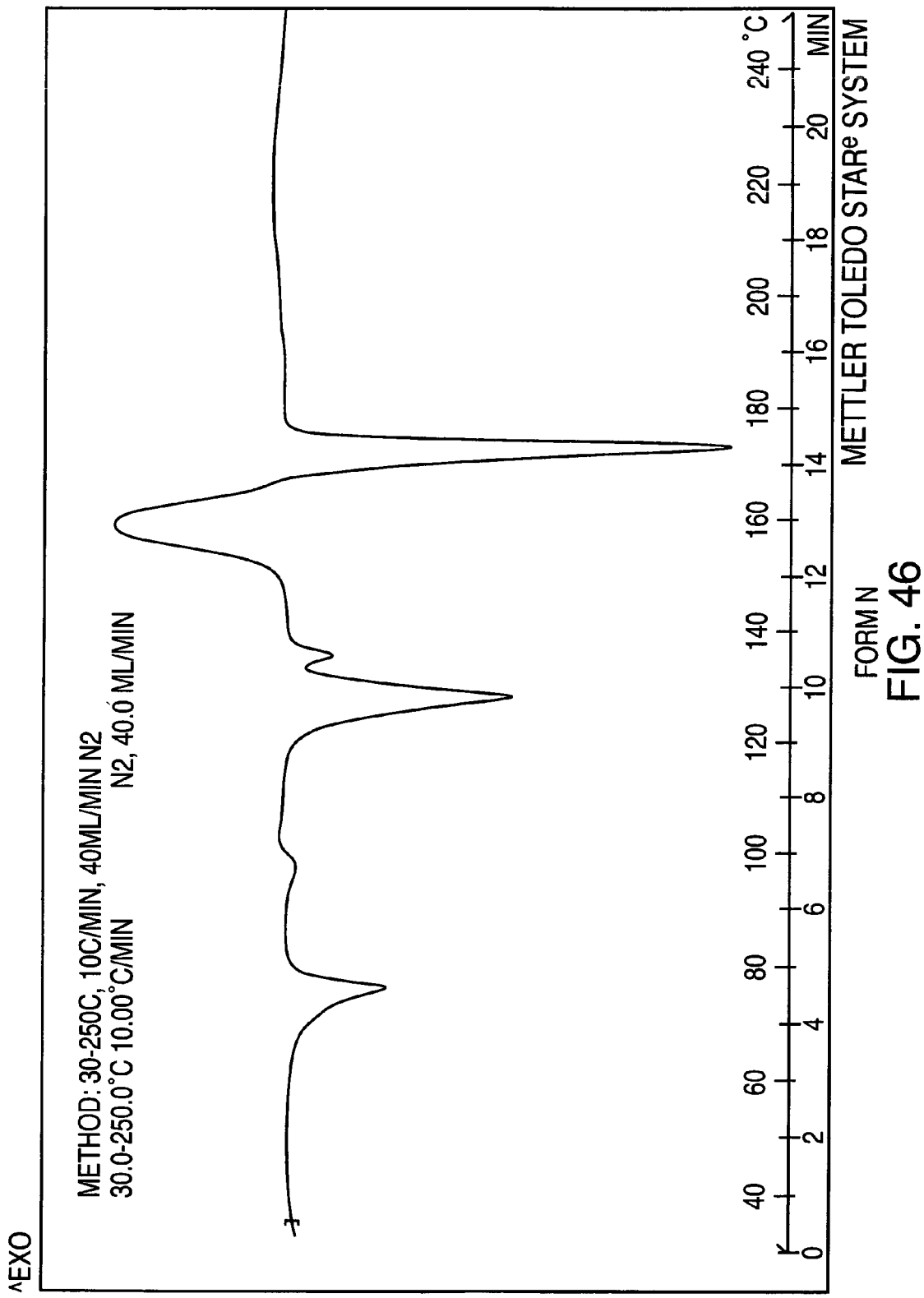
FIG. 46 is a DSC thermogram of nateglinide Form N.
Figure 47:
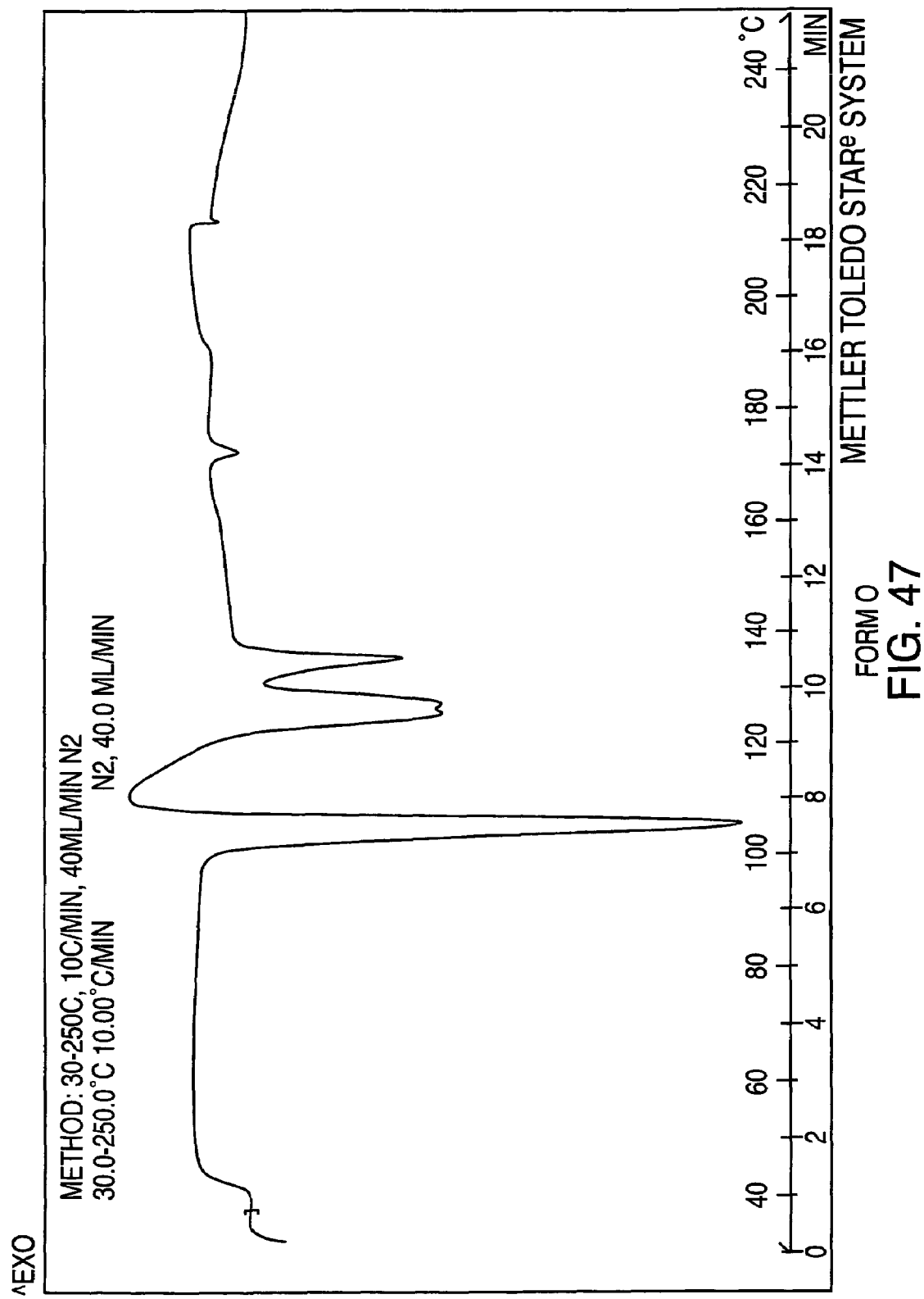
FIG. 47 is a DSC thermogram of nateglinide Form O.
Figure 48:
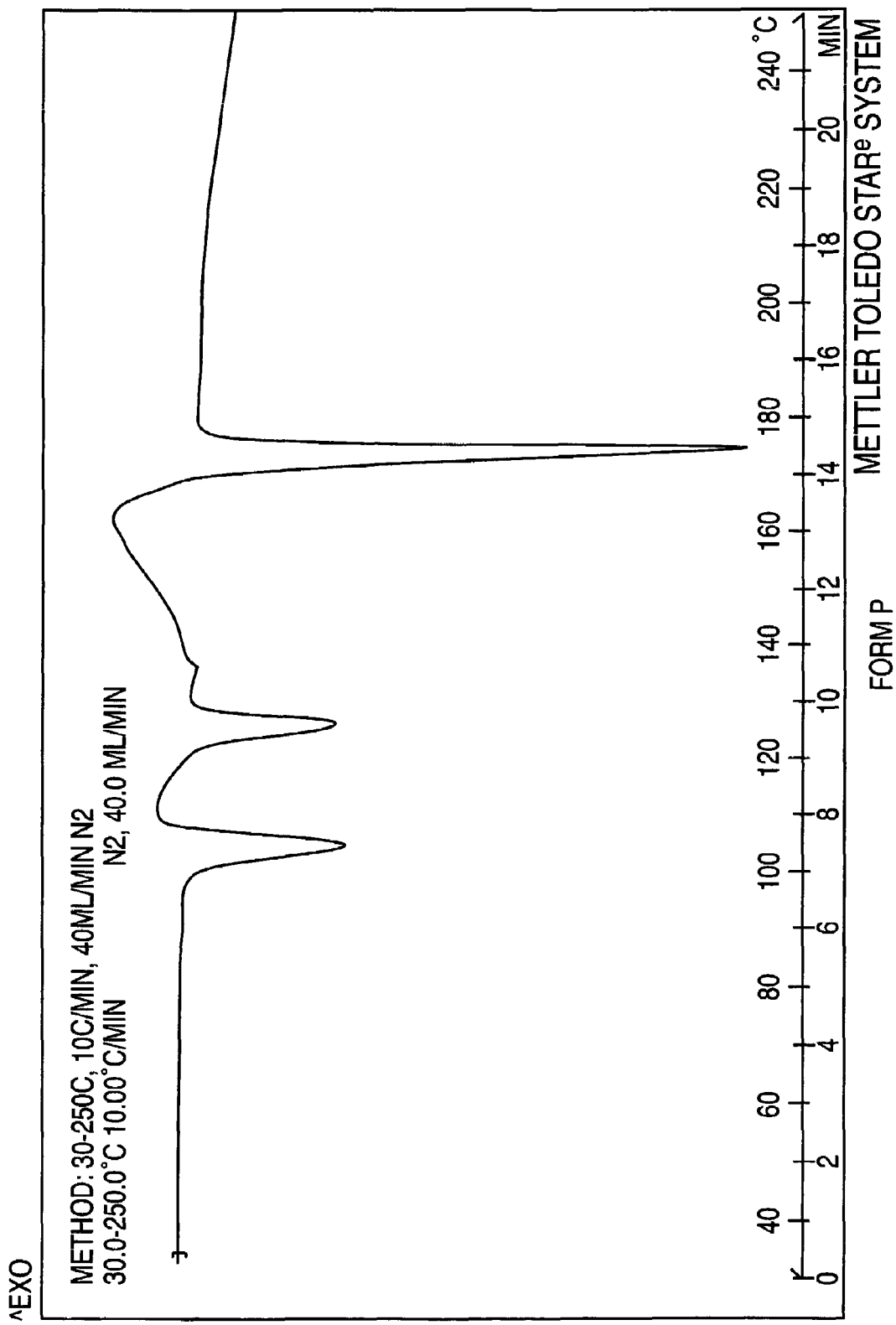
FIG. 48 is a DSC thermogram of nateglinide Form P.
Figure 49:
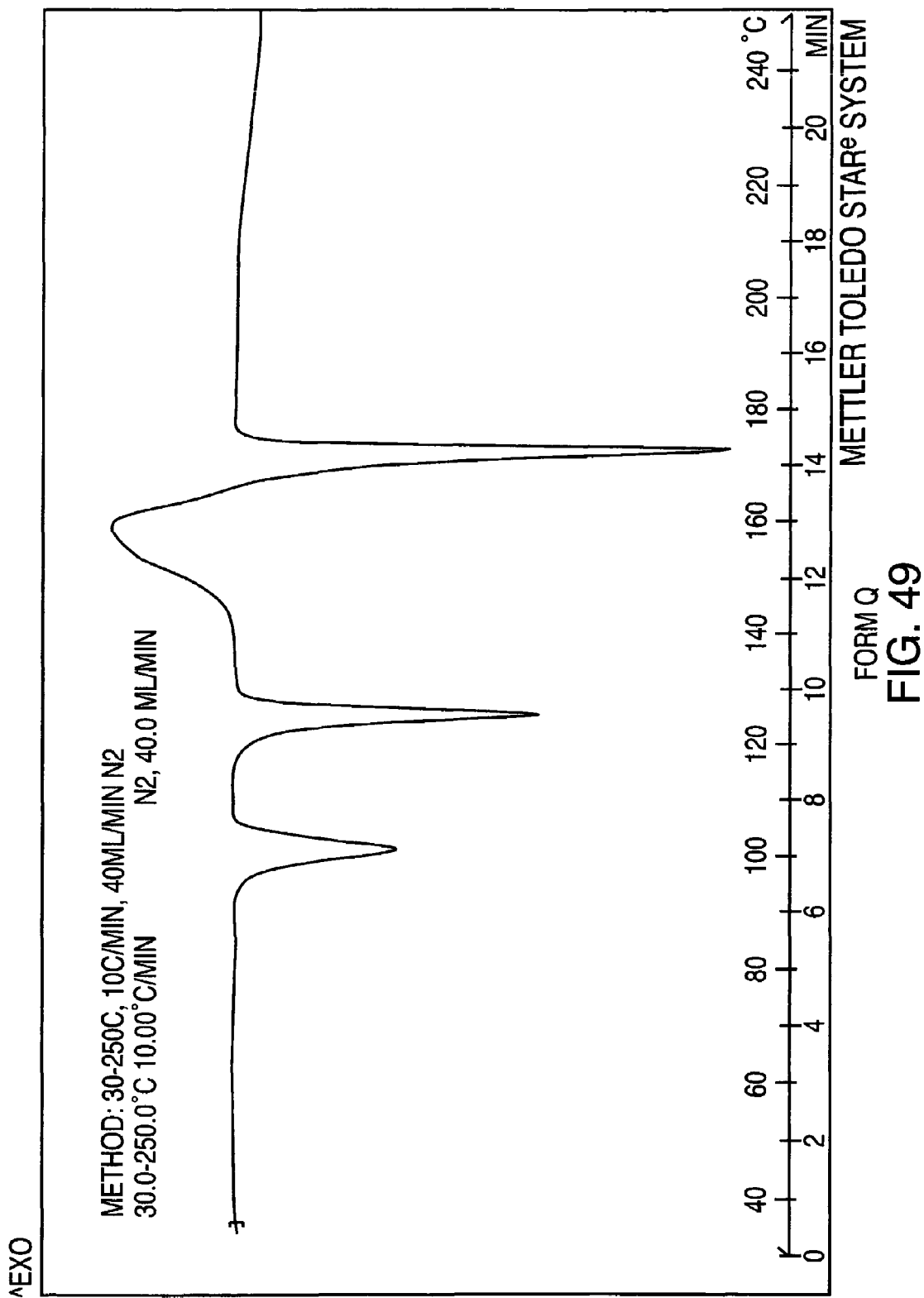
FIG. 49 is a DSC thermogram of nateglinide Form Q.
Figure 50:
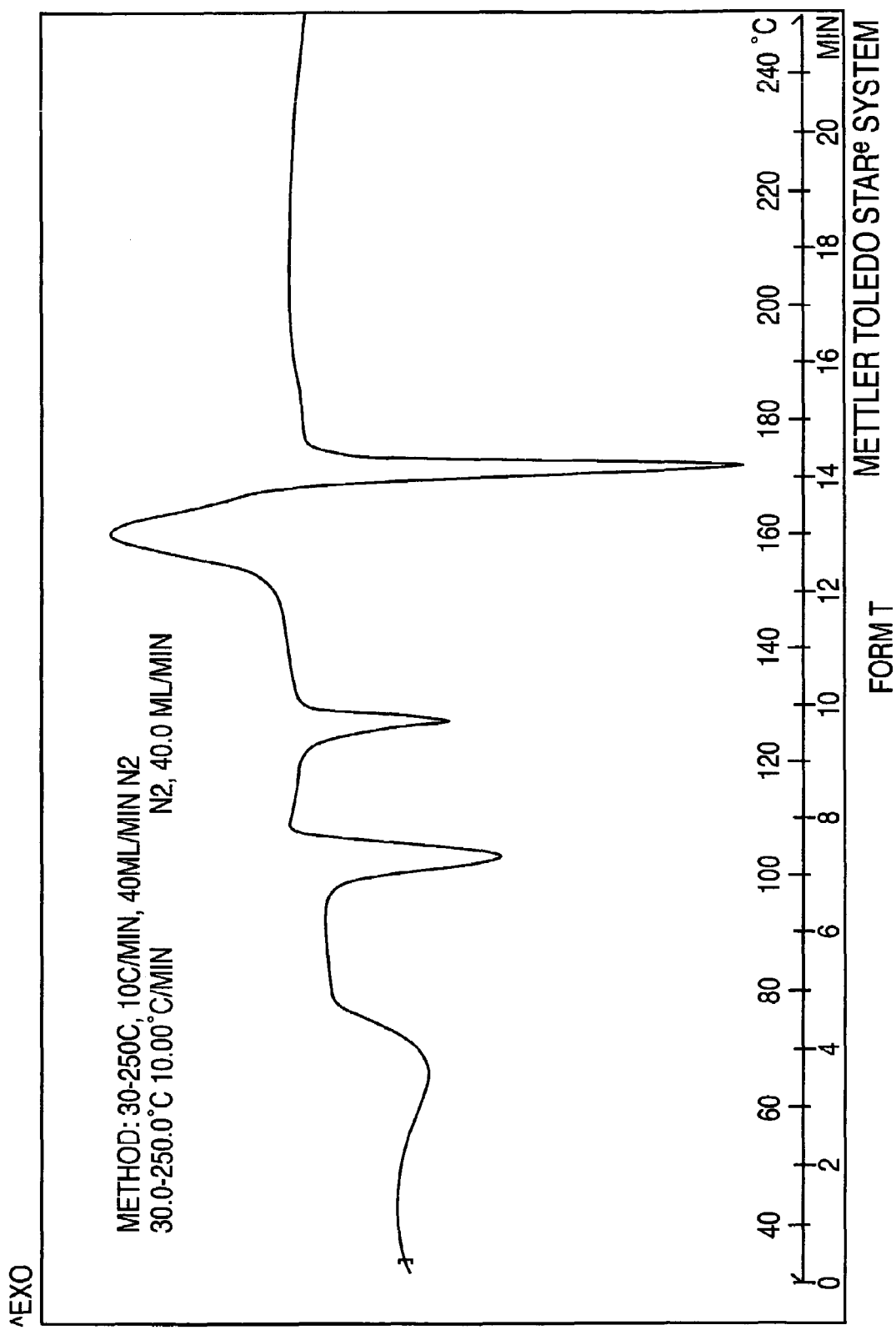
FIG. 50 is a DSC thermogram of nateglinide Form T.
Figure 51:
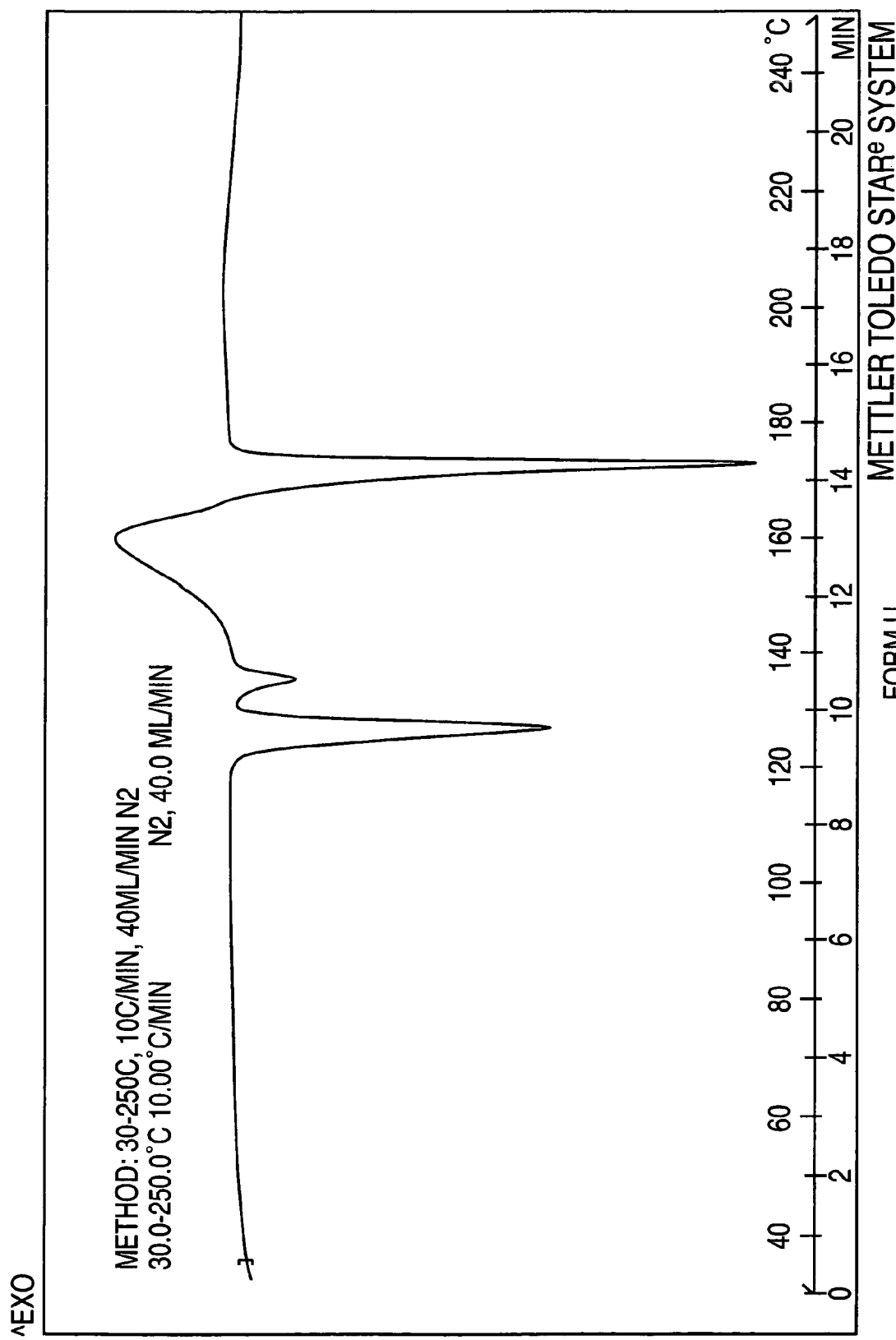
FIG. 51 is a DSC thermogram of nateglinide Form U in impure Form.
Figure 52:
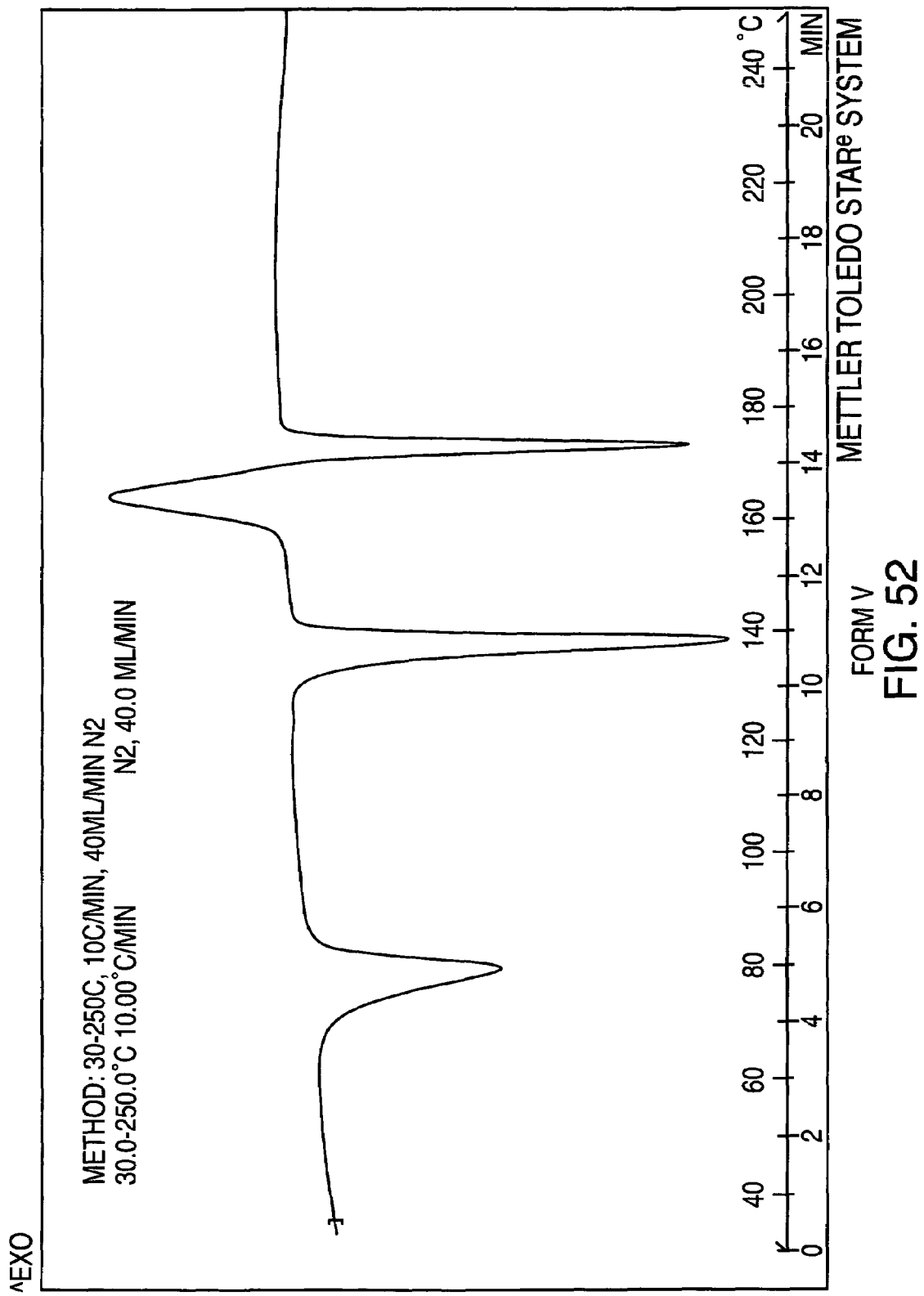
FIG. 52 is a DSC thermogram of nateglinide Form V.
Figure 53:
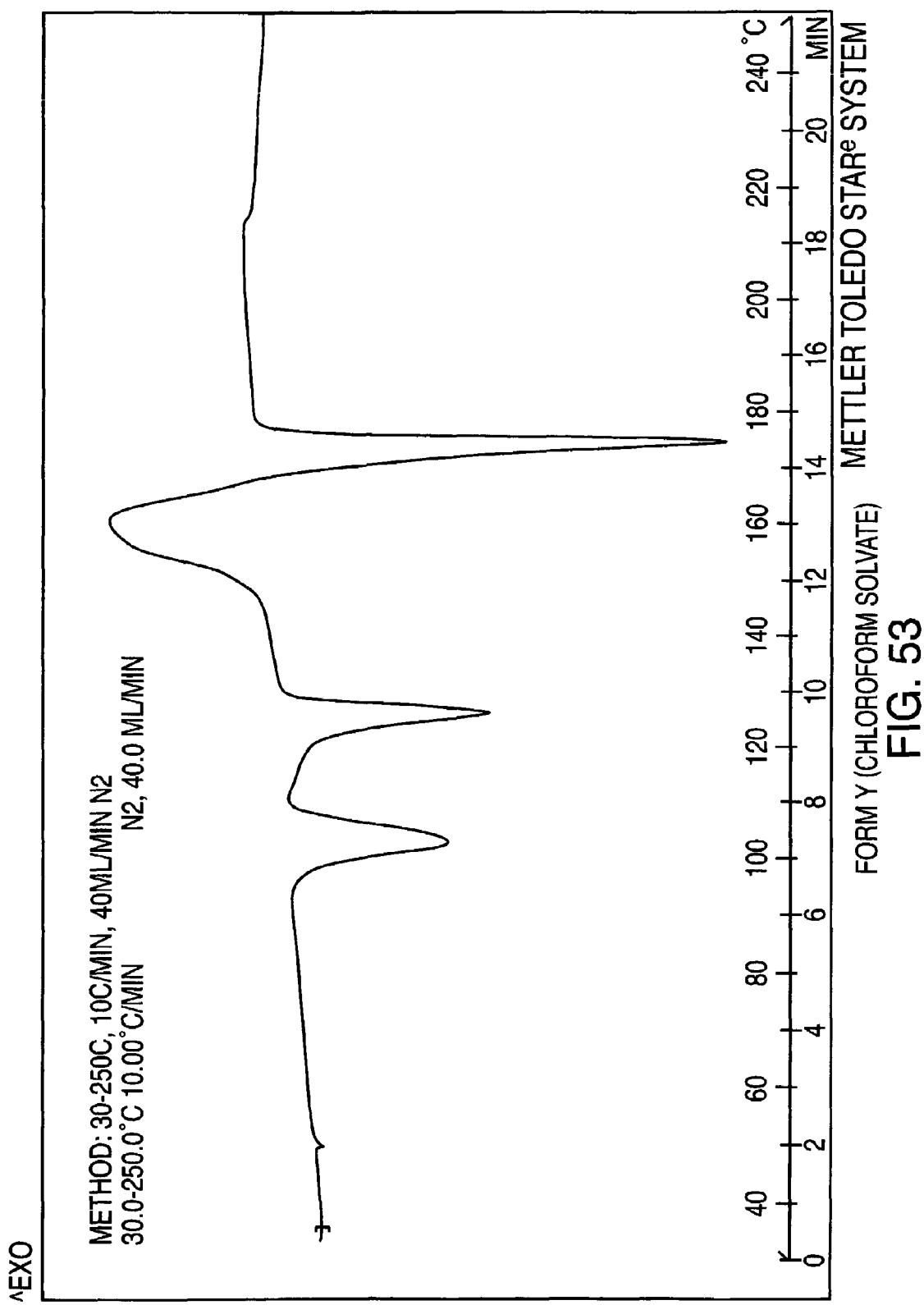
FIG. 53 is a DSC thermogram of nateglinide Form Y (chloroform solvate).
Figure 54:
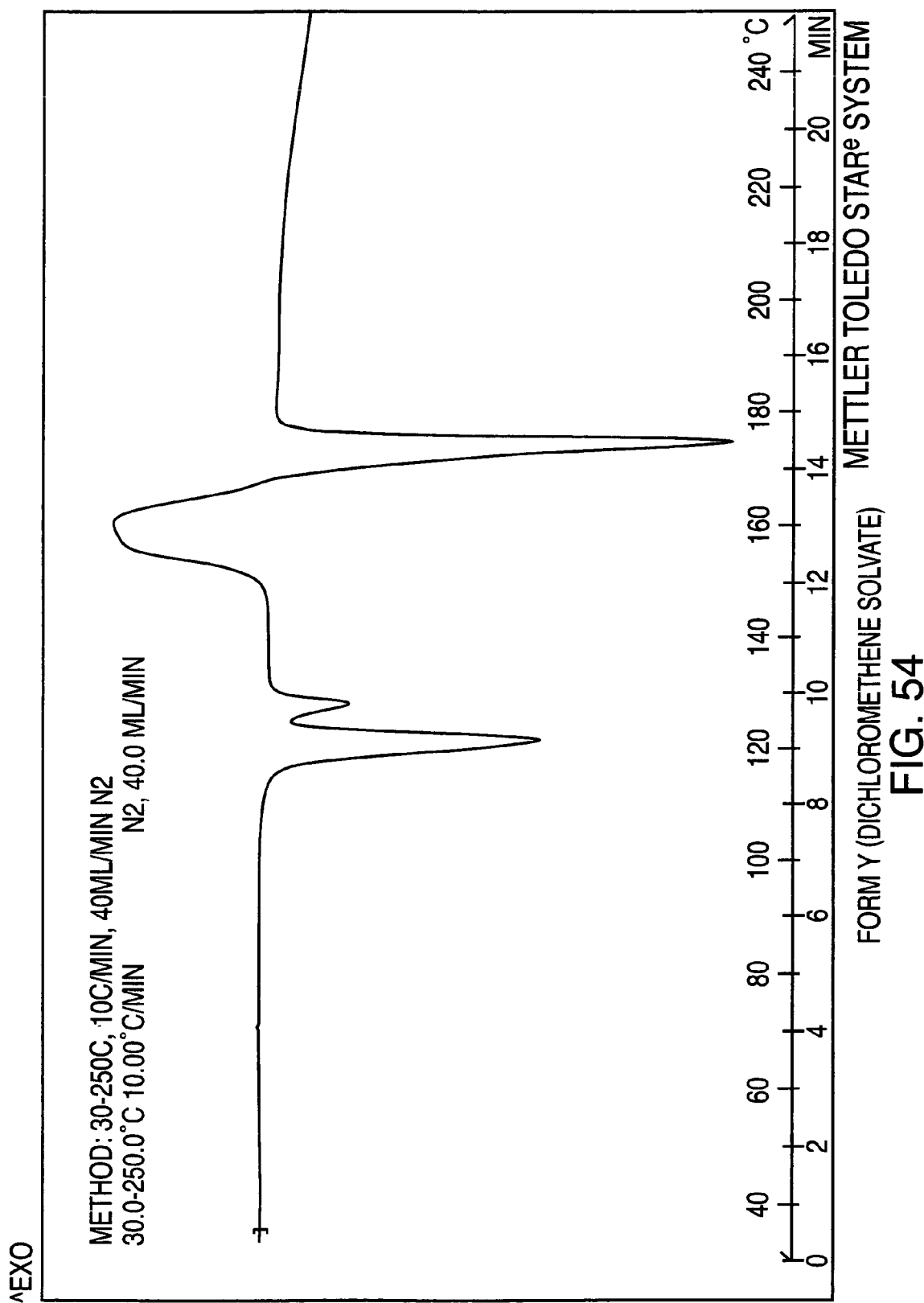
FIG. 54 is a DSC thermogram of nateglinide Form Y (dichloromethane solvate).
Figure 55:
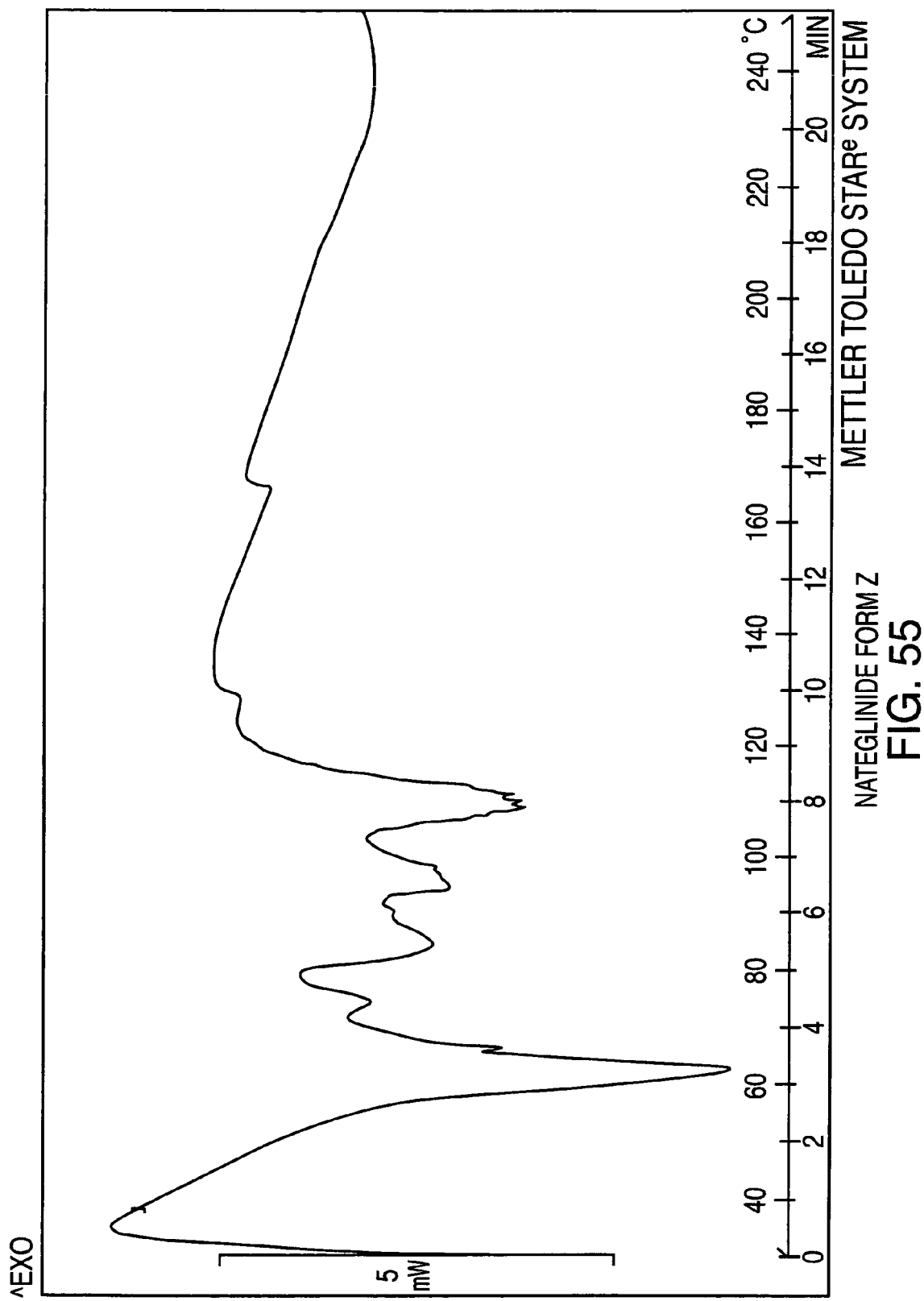
FIG. 55 is a DSC thremogram of nateglinide Form Z.
Figure 56:
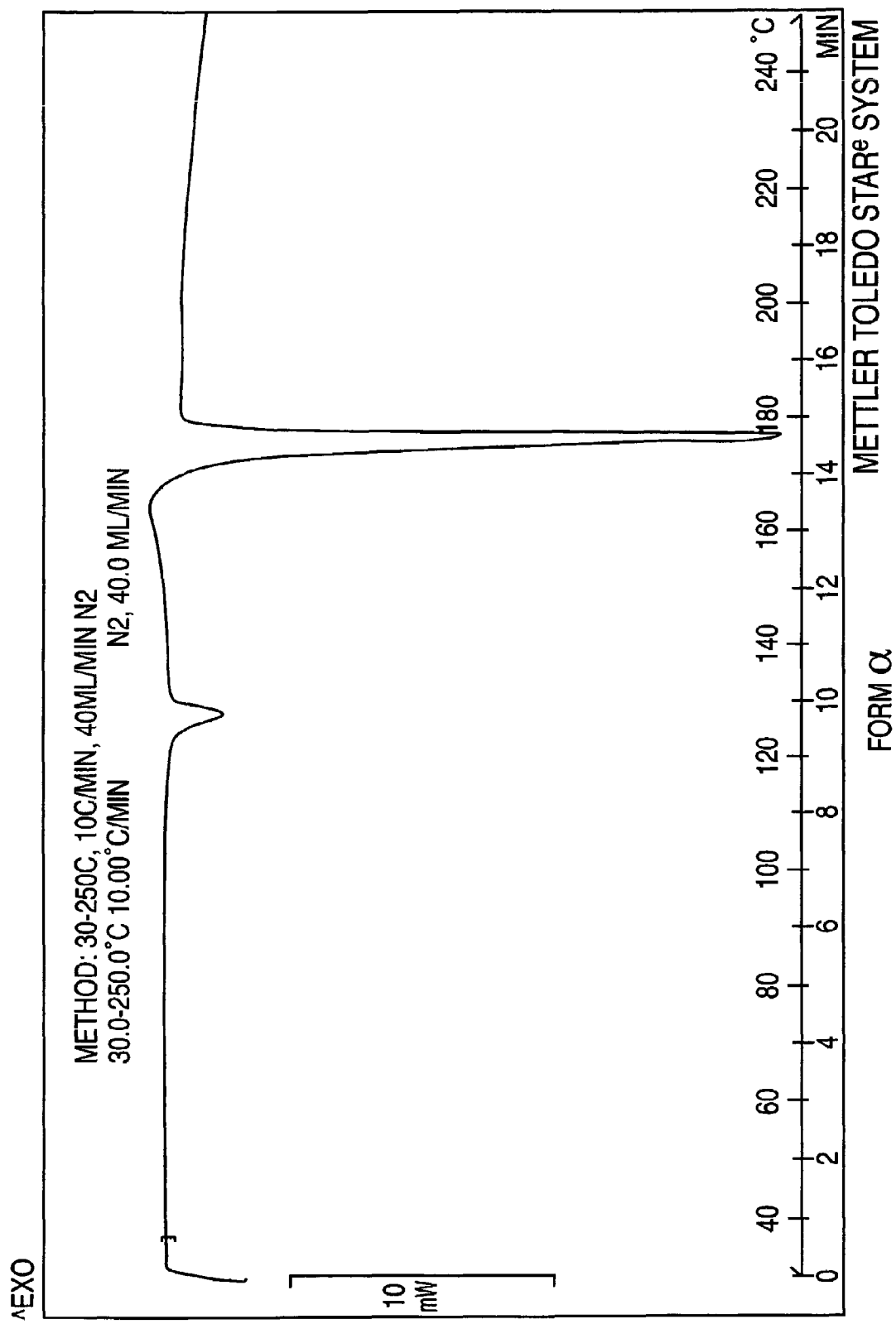
FIG. 56 is a DSC thermogram of nateglinide Form α.
Figure 57:
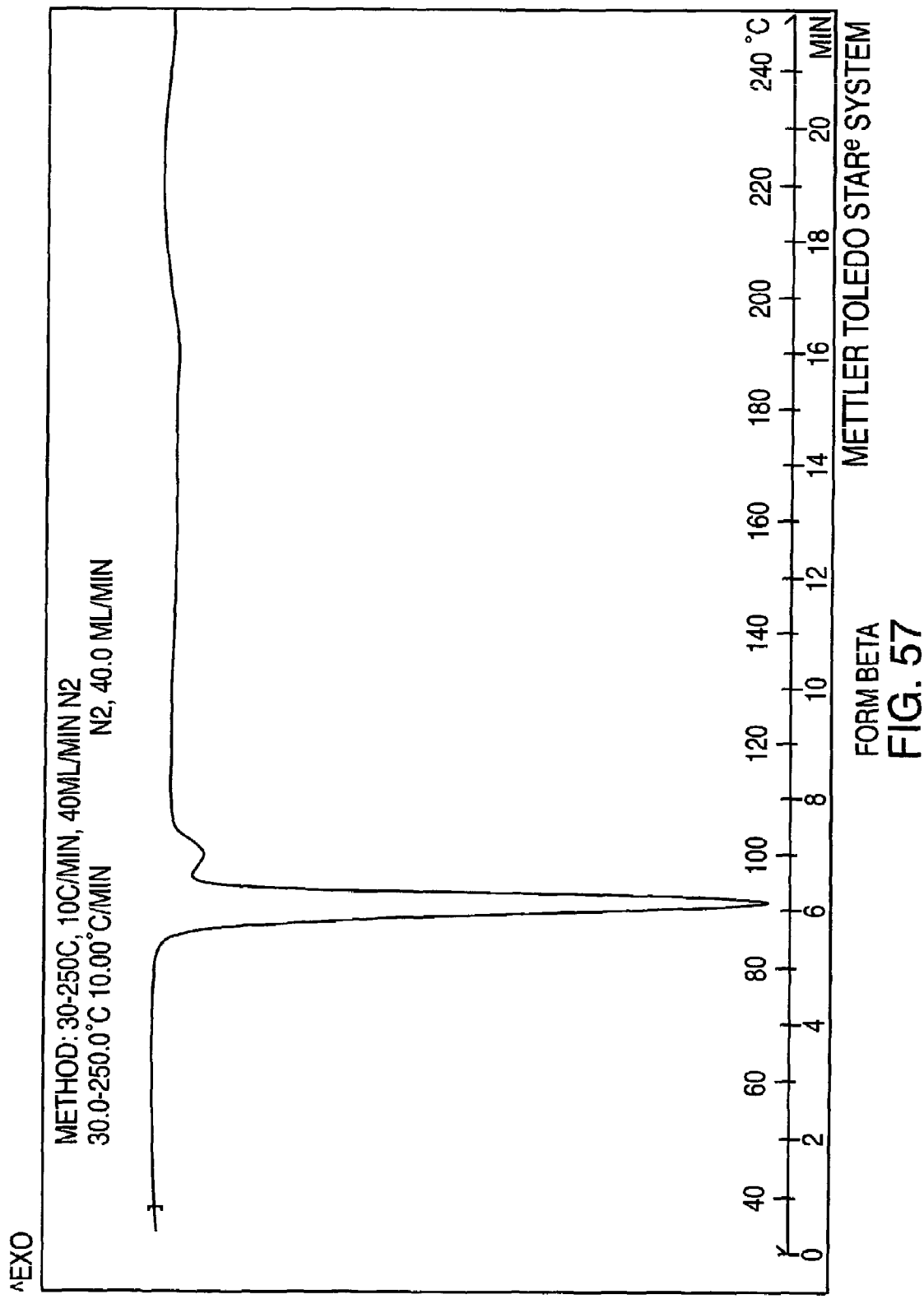
FIG. 57 is a DSC thermogram of nateglinide Form β.
Figure 58:
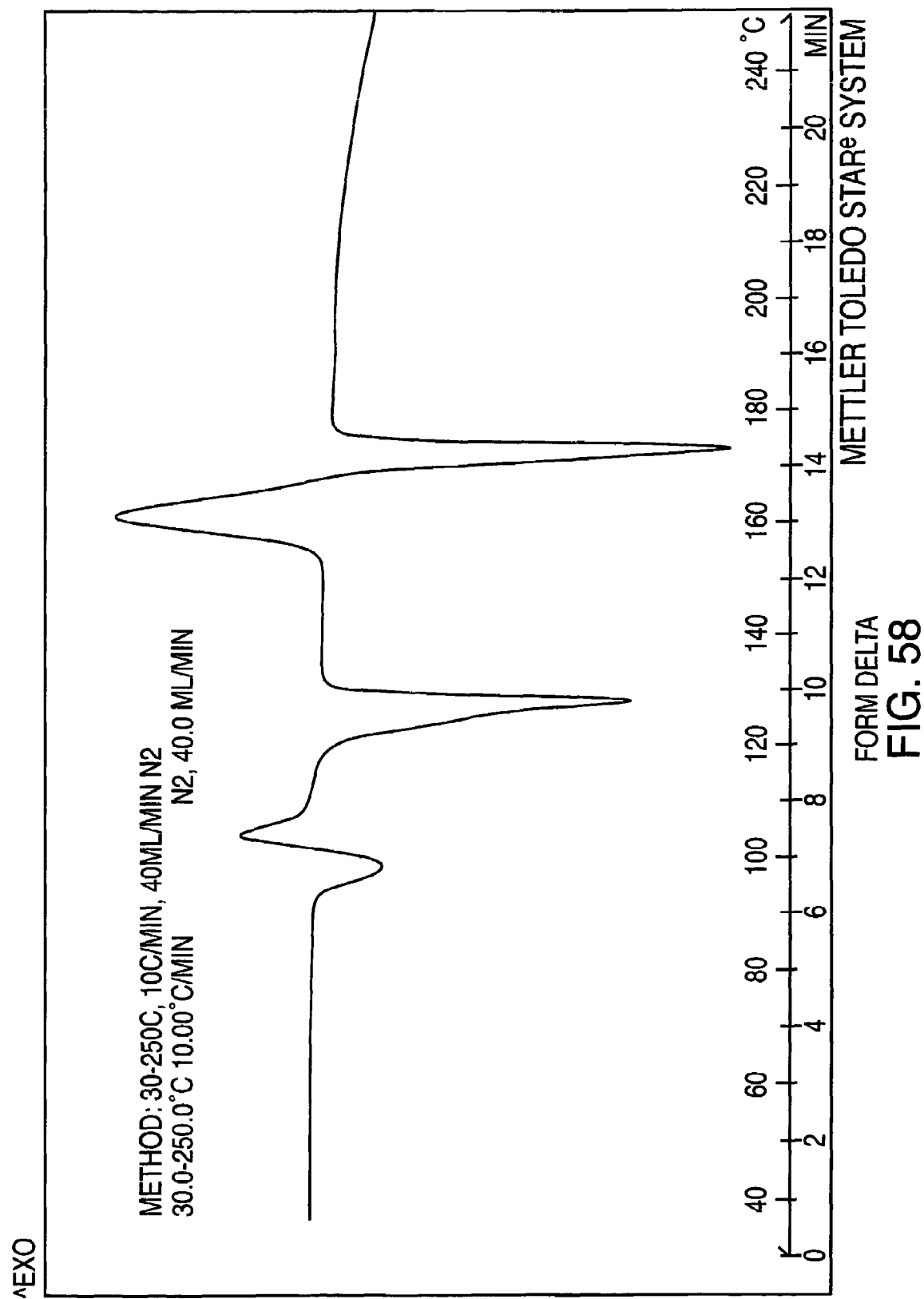
FIG. 58 is a DSC thermogram of nateglinide Form γ.
Figure 59:
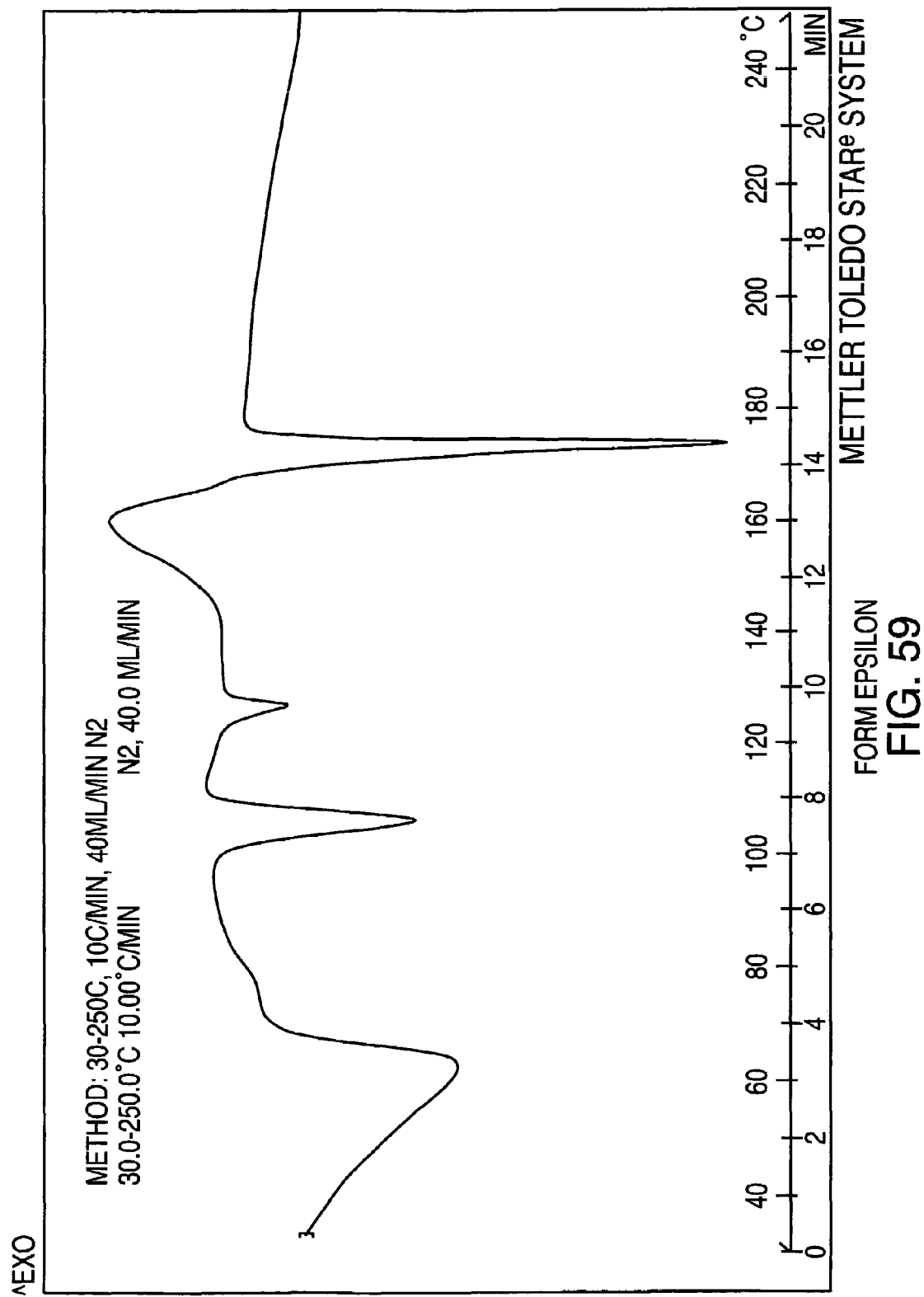
FIG. 59 is a DSC thermogram of nateglinide Form δ.
Figure 60:
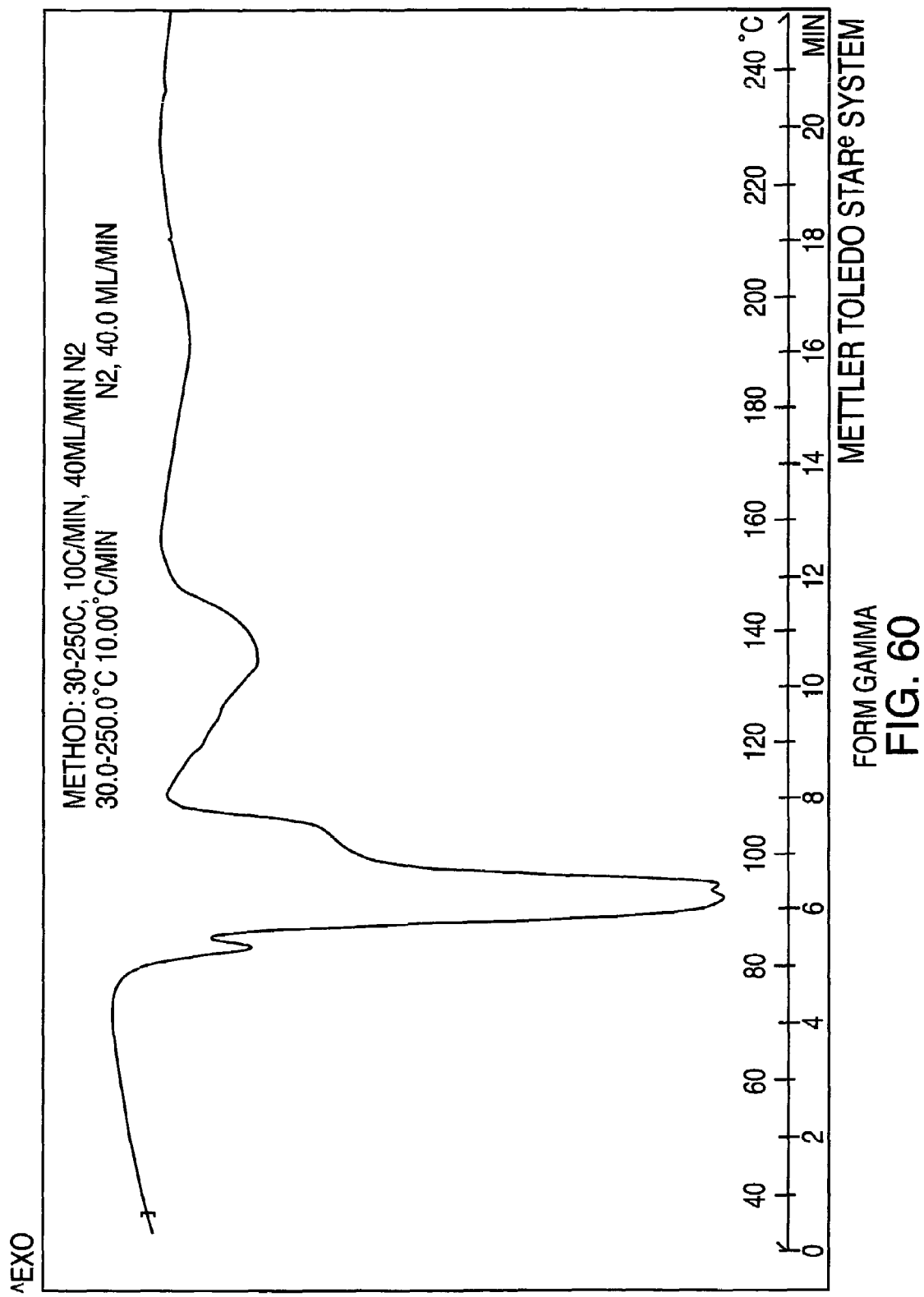
FIG. 60 is a DSC thermogram of nateglinide Form ε.
Figure 61:
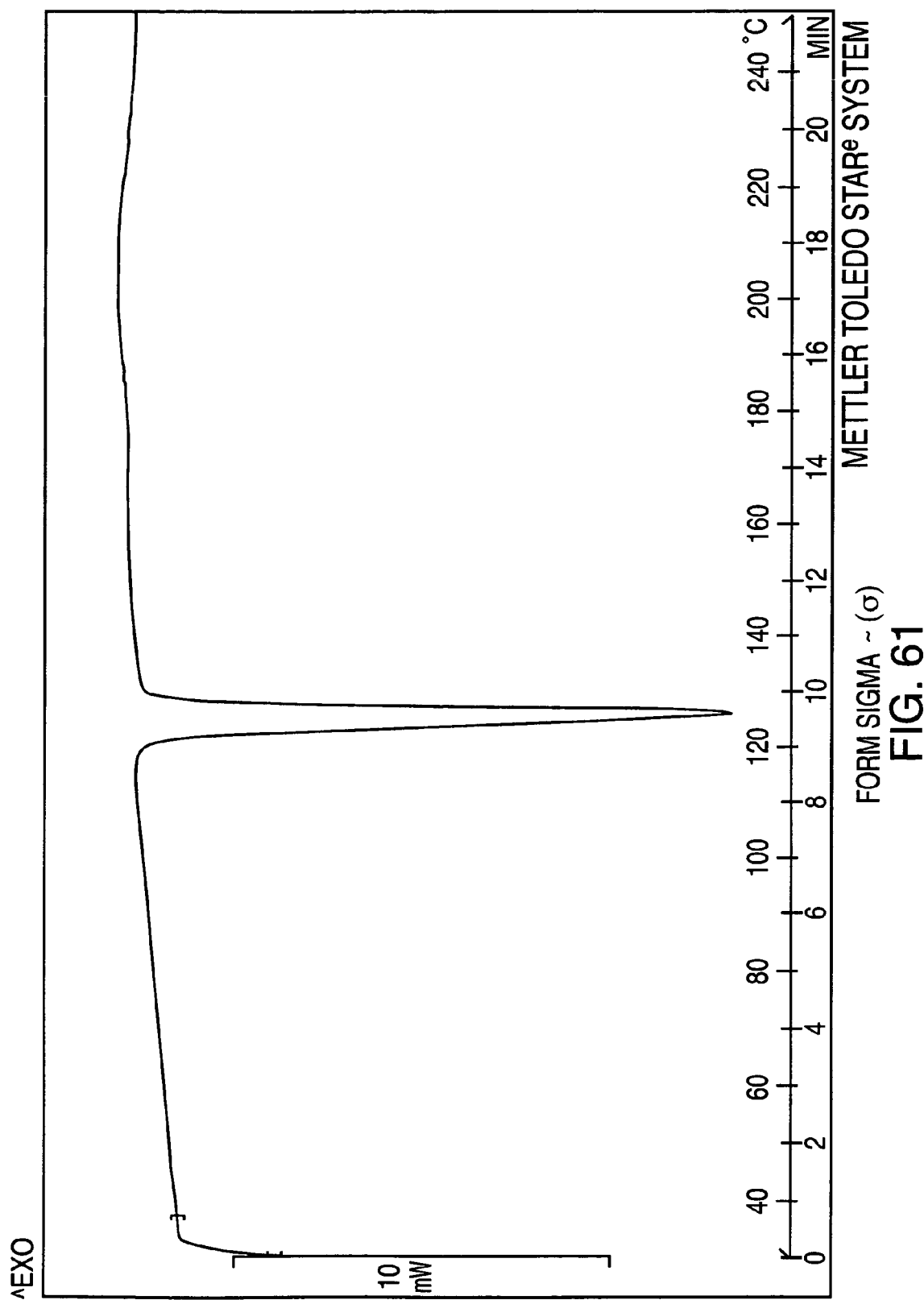
FIG. 61 is a DSC thermogram of nateglinide Form σ.
Figure 62:
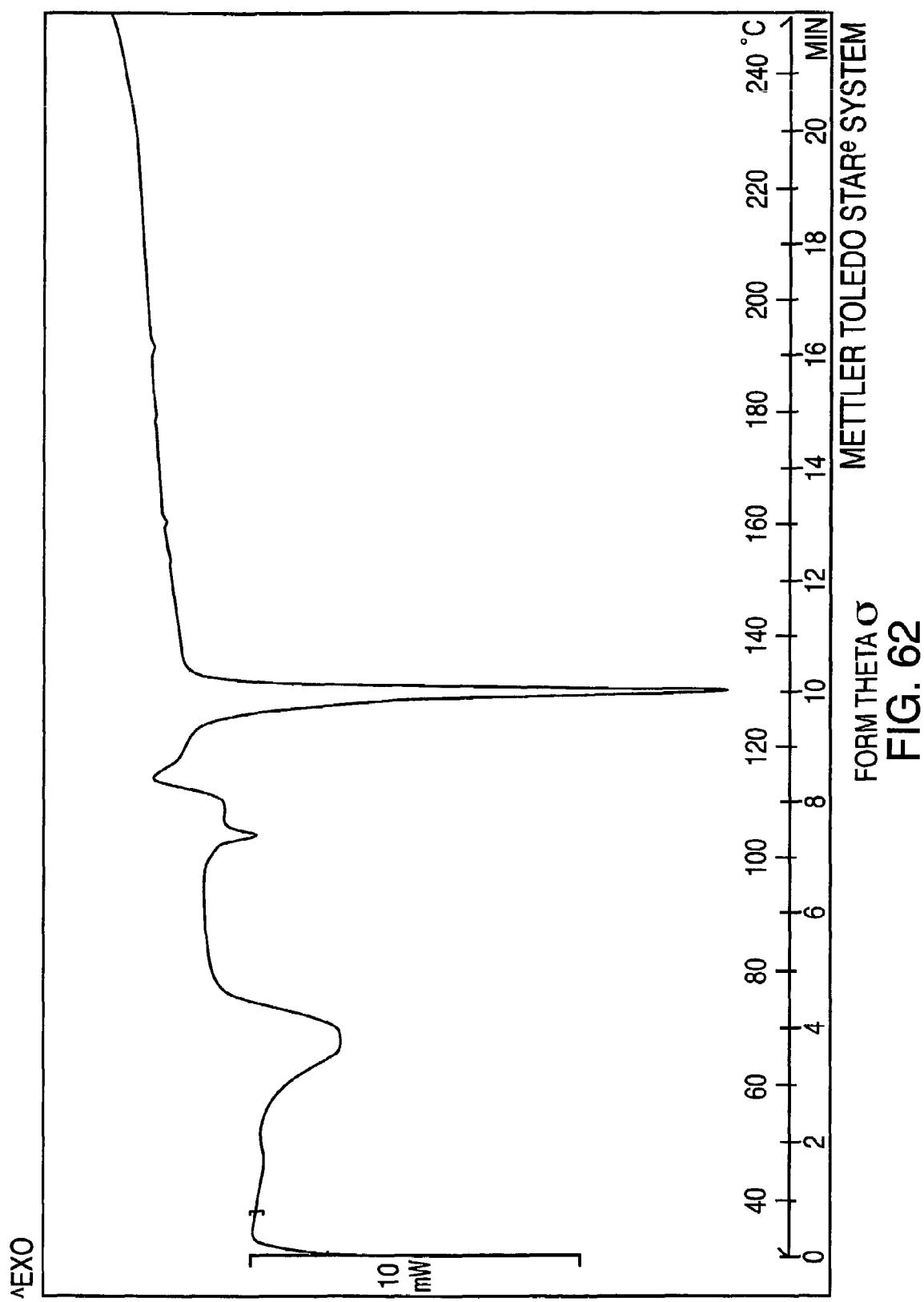
FIG. 62 is a DSC thermogram of nateglinide Form θ.
Figure 63:
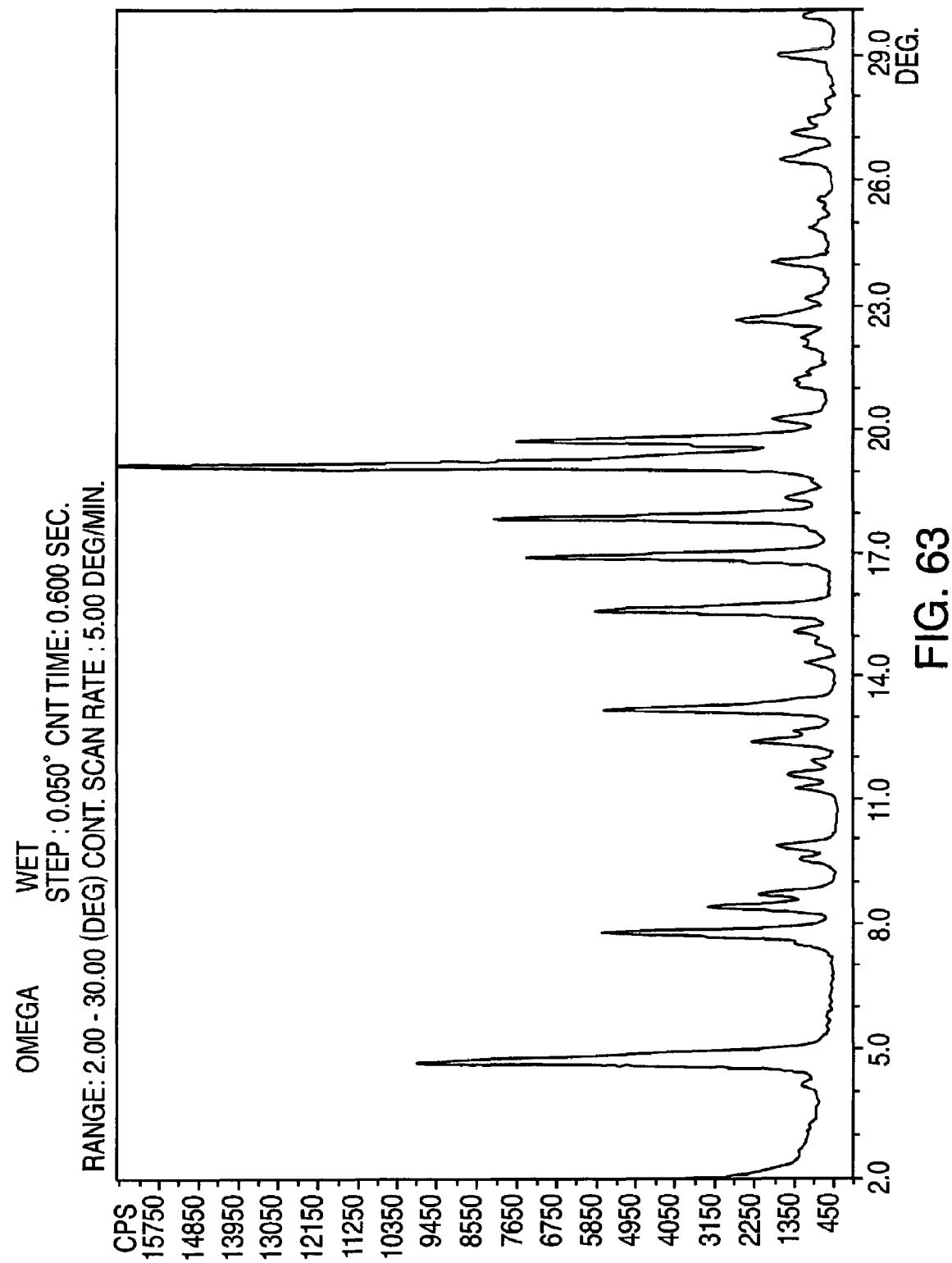
FIG. 63 is a XRPD pattern of nateglinide Form Ω.
Figure 65:
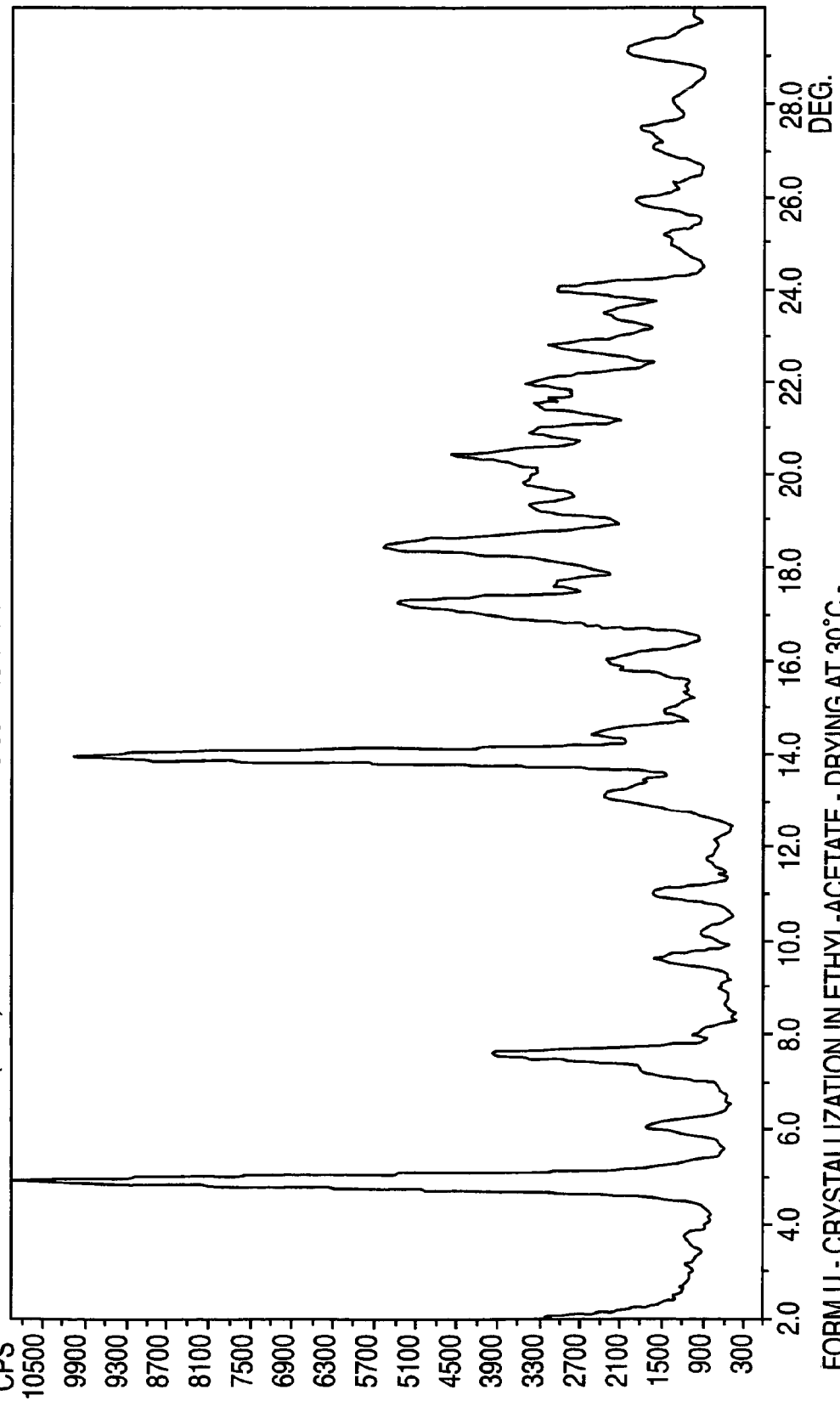
FIG. 65 is a XRPD pattern of nateglinide pure Form U prepared according to Example 17, lacking the impurity at 3.8+/−0.2 shown in FIG. 17.
Figure 66:
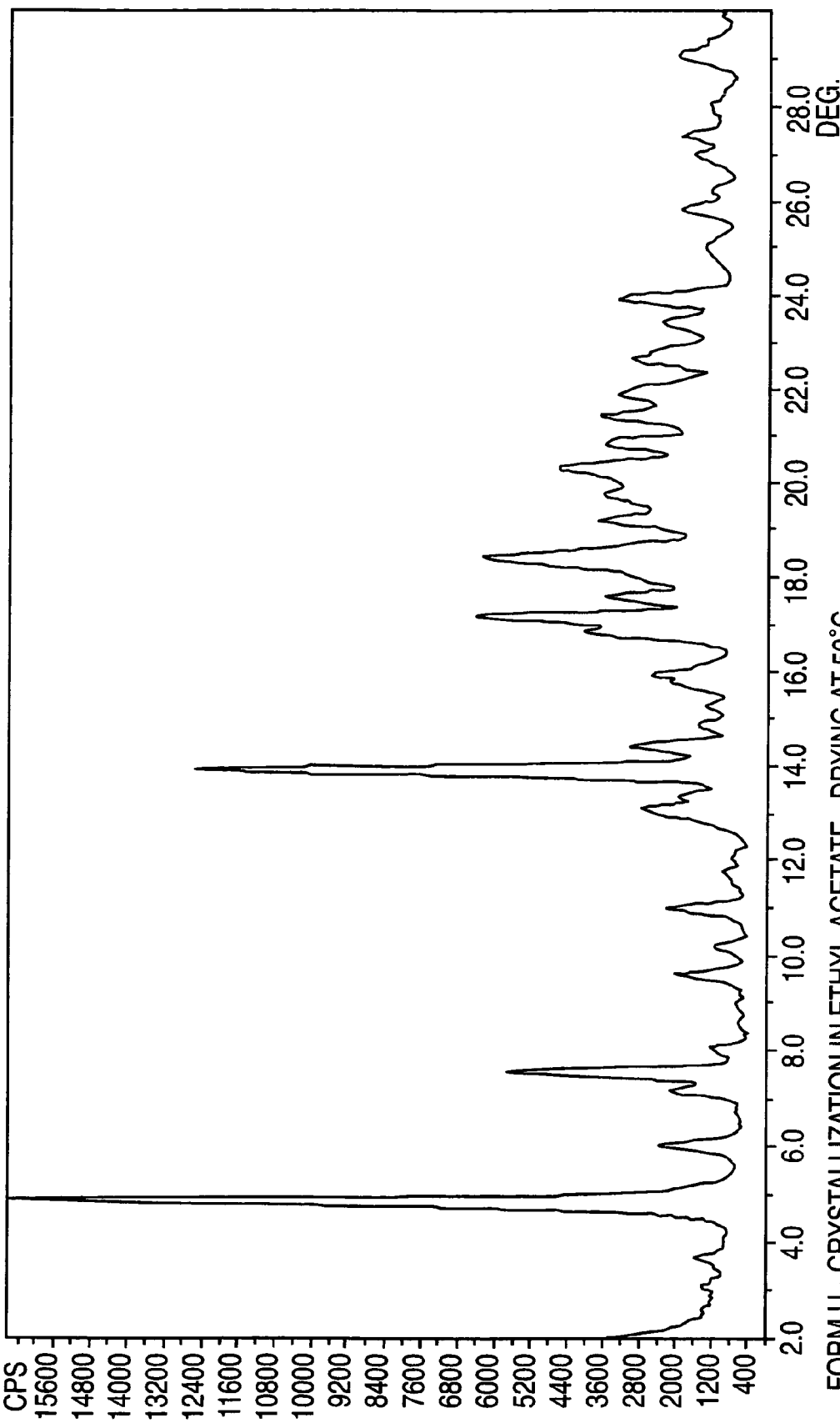
FIG. 66 is a XRPD pattern of nateglinide pure Form U prepared according to Example 17, lacking the impurity at 3.8+/−0.2 shown in FIG. 17.
Figure 67:
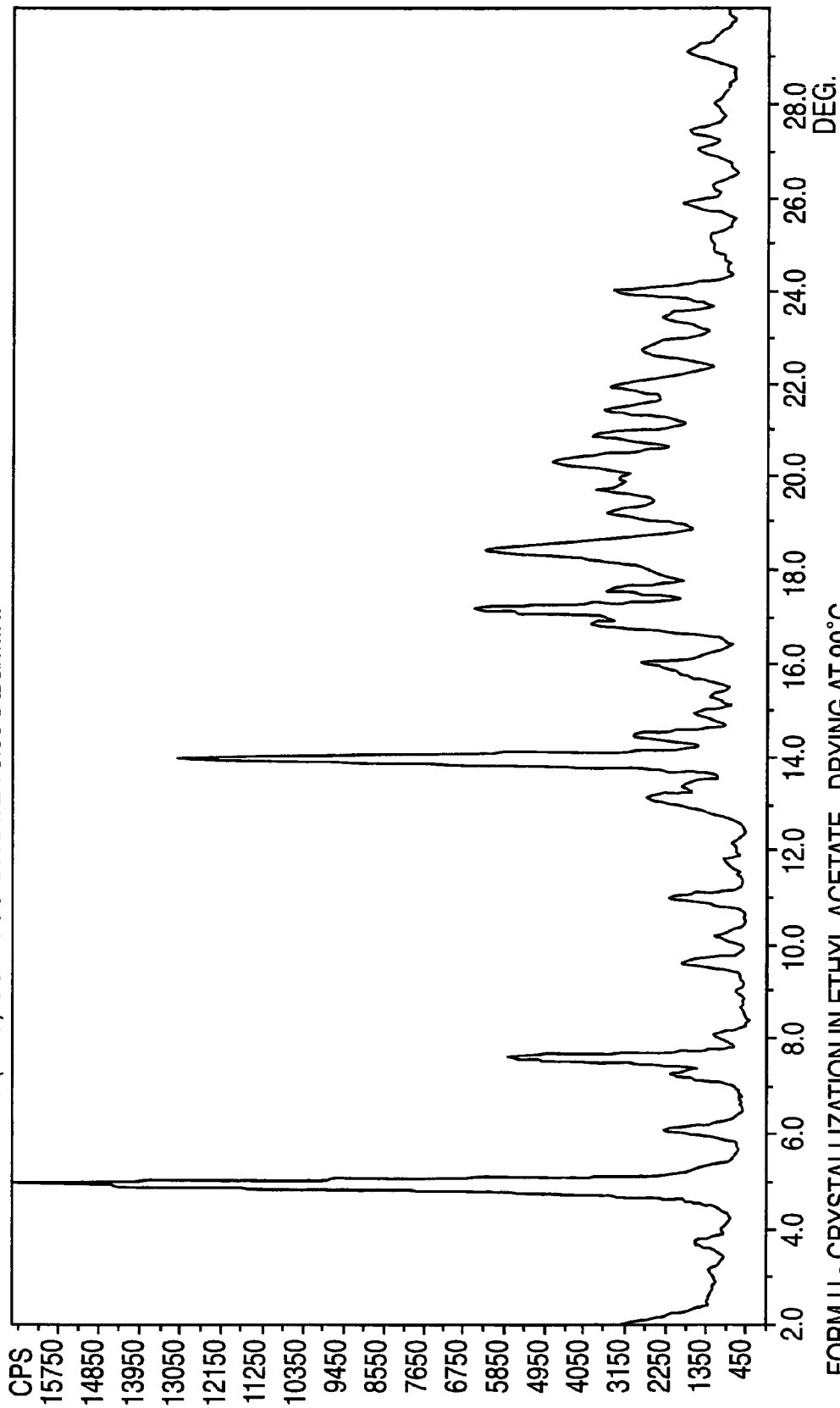
FIG. 67 is a XRPD pattern of nateglinide pure Form U prepared according to Example 17, lacking the impurity at 3.8+/−0.2 shown in FIG. 17.
Figure 68:
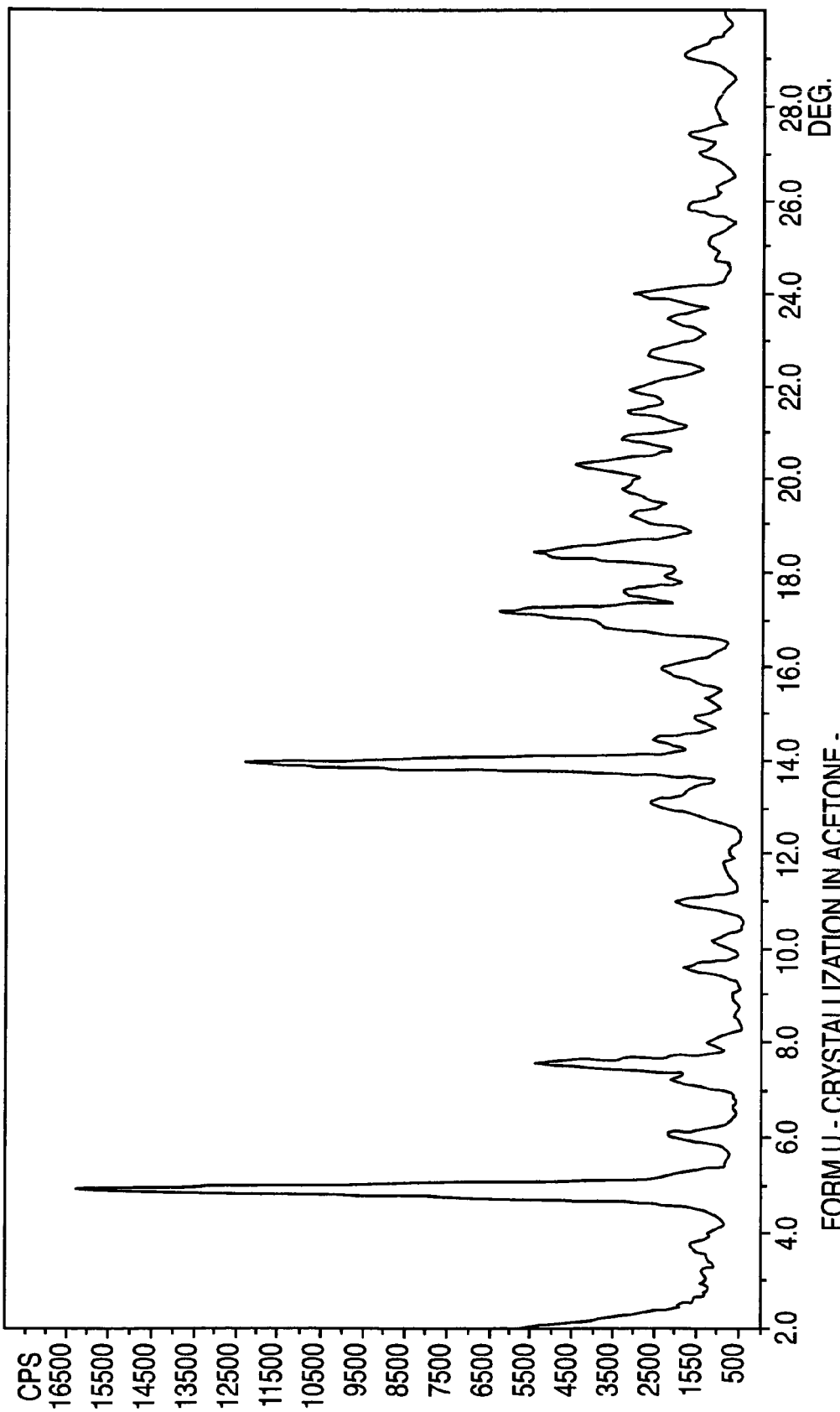
FIG. 68 is a XRPD pattern of nateglinide pure Form U prepared according to Example 17, lacking the impurity at 3.8+/−0.2 shown in FIG. 17.

| Crystal Form | DSC Peaks (° C.) | | | |
|---|---|---|---|---|
| A (FIG. 36) | 70 | 98 | 138 | — |
| D (FIG. 37) | 66 | 130 | — | — |
| E (FIG. 38) | 75 | 86 | 104 | 129 |
| F (FIG. 39) | 53 | 103 | 128 | — |
| G (FIG. 40) | 106 | 127 | — | — |
| I (FIG. 41) | 46 | 121 | — | — |
| J (FIG. 42) | 49 | 105 | 168 | — |
| K (FIG. 43) | 79 | 105 | 145 | 170 |
| L (FIG. 44) | 131 | 138 | — | — |
| M (FIG. 45) | 90 | 102 | 128 | — |
| N (FIG. 46) | 77 | 100 | 130 | 137 |
| O (FIG. 47) | 106 | 126 | 137 | — |
| P (FIG. 48) | 106 | 113 (exotherm) | 128 | — |
| Q (FIG. 49) | 102 | 126 | — | — |
| T (FIG. 50) | 68 | 106 | 130 | — |
| U (FIG. 51) | 128 | 138 | — | — |
| V (FIG. 52) | 81 | 139 | — | — |
| Y dichloromethane solvate (FIG. 54) | 122 | 130 | — | — |
| Z (FIG. 53) | 90 | 95 | | |
| α (FIG. 56) | 129 | — | — | — |
| β (FIG. 57) | 91 | 100 | — | — |
| γ (FIG. 58) | 93 | 136 | — | — |
| δ (FIG. 59) | 100 | 107 (exotherm) | 130 | — |
| ε (FIG. 60) | 64 | 108 | 129 | — |
| σ (FIG. 61) | — | — | — | 127 |
| θ (FIG. 62) | 70 | 104 | 115 (exo) | 130 |

The various crystalline forms are also analyzed by Thermal Gravimetric Analysis (TGA). TGA measurements show that Forms A, D, E, F, G, I, J, K, M, N, O, Q, T, U, V, Y, Z, β, γ, ε, θ and Ω contain significant amounts of bound solvents and may be considered as solvated forms of nateglinide. The XRPD analysis of some of these solvated forms show that some of them are unstable when left in an open bottle for 24 hours. In contrast to the above listed forms, TGA profiles of forms L, P, U, α, δ and σ show no significant weight loss. These polymorphic forms of nateglinide are free of bound solvents, i.e., less than about 2% LOD. Table III lists the solvents used for the preparation for nateglinide solvated forms, as well as LOD values based on TGA analysis.

The ethanol solvate of nateglinide disclosed herein has an ethanol content of from about 10% to about 30% by weight. The ethanol solvate of nateglinide ethanol solvate is represented by formula NTG·3/2 EtOH. Specifically, the solvate is nateglinide Form D.

The methanol solvates of nateglinide disclosed herein have a methanol content of from about 2 to about 60% by weight. Specifically, nateglinide methanol solvate exists as nateglinide Form E, Form O and Form T methanol solvate. Nateglinide methanol solvate is represented by the formula NTG*1/4 MeOH (Form O) or by the formula NTG*1/2 MeOH (form E). Nateglinide Form T contains more than about 20% methanol by weight. The methanol content of Form T is from about 20% to about 60% by weight.

The isopropyl solvate of nateglinide disclosed herein has an isopropyl alcohol content of from about 12% to about 30% by weight. Specifically, isopropyl solvate of nateglinide exists as nateglinide Form G.

A hydrate of nateglinide, Form Z, has a water content of about 10 to about 50%, more preferably about 10% to about 40%, and most preferably from about 15% to about 25%, measured either by the Karl Fischer method or LOD. Form Ω, is a hydrate-solvate of isopropanol and contains about 50% LOD water and isopropanol.

The heptane solvated form of nateglinide, Form θ, has about 7 to about 8% heptane by weight, and is represented by the formula NTG·1/4 Heptane.

TABLE III

LOD values by TGA and solvents used for the preparation of nateglinide solvated forms

| Crystal Form | Solvent | LOD by TGA (weight %) | Comments |
|---|---|---|---|
| A | Xylene | 80 | Storage at RT for 24 h is results in a partial conversion to Form B |
| C | DMA | >5 | |
| D | Ethanol | 25 | |
| E | MeOH | 4 | |
| F | n-PrOH | 16-24 | |
| G | Isopropyl Alcohol | 22-28 | |
| I | n-BuOH | 20 | Storage at RT for 24 h results in a conversion to Form L |
| J | N-Methyl Pyrolidone | 2-3 up to 100° C. sharp weight loss at 100° C. | XRD pattern slightly changed after storage at RT for overnight |
| K | Dimethyl formamide | 34 | |
| M | Carbon tetra chloride | 2 | |
| N | Dichloroethane | 8 | |
| O | MeOH | 2 | |
| Q | Chloroform | 10 | Storage at RT for 24 h results in a conversion to Form Y, which contains chloroform. |
| T | MeOH | >20 | Storage at RT for 24 h results in a conversion to Form E |

TABLE III-continued

LOD values by TGA and solvents used for the preparation of nateglinide solvated forms

| Crystal Form | Solvent | LOD by TGA (weight %) | Comments |
| --- | --- | --- | --- |
| V | Dimethoxyethane | 8-16 | A sharp weight loss step of 7-8% is observed at 70° C. |
| Y | Dichloromethane/ Chloroform | 2-8 | |
| Beta | N-Methyl Pyrolidone | — | |
| Gamma | N-Methyl Pyrolidone | — | No significant weight loss up to 90° C. Sharp weight loss at 90° C. |
| Epsilon | Acetone/ Nitromethane/ Acetonitrile | Above 4 | |
| Theta | Heptane | 7.4% | |
| Omega | IPA and Water | 50% | |

Figure 31:
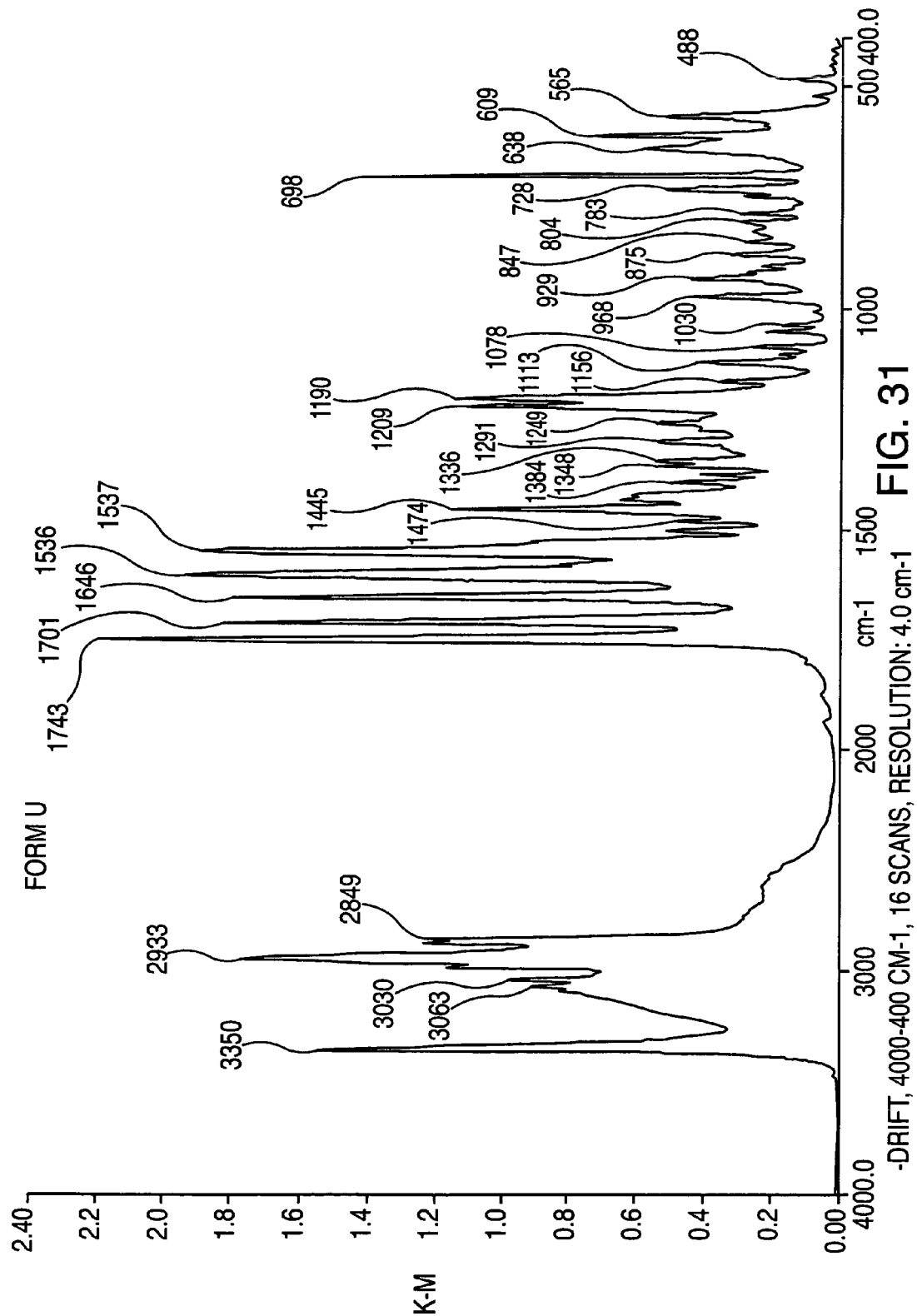
FIG. 31 is an FTIR spectrum of nateglinide Form U in pure form.

The anhydrate forms and the hydrated Form Z, are also characterized by their FTIR spectrum. Form Z is characterized by a FTIR spectrum (FIG. 31) with peaks at about 699, 1542, 1645, 1697, 2848, 2864, 2929, 3279 and 3504 cm$^{-1}$. The more characteristic peaks are observed at about 1645, 1697, 3279 and 3504 cm$^{-1}$. Characteristic FTIR peaks are for the anhydrates, specifically Forms L, U, P, α, δ and σ are disclosed in the following table.

Figure 28:
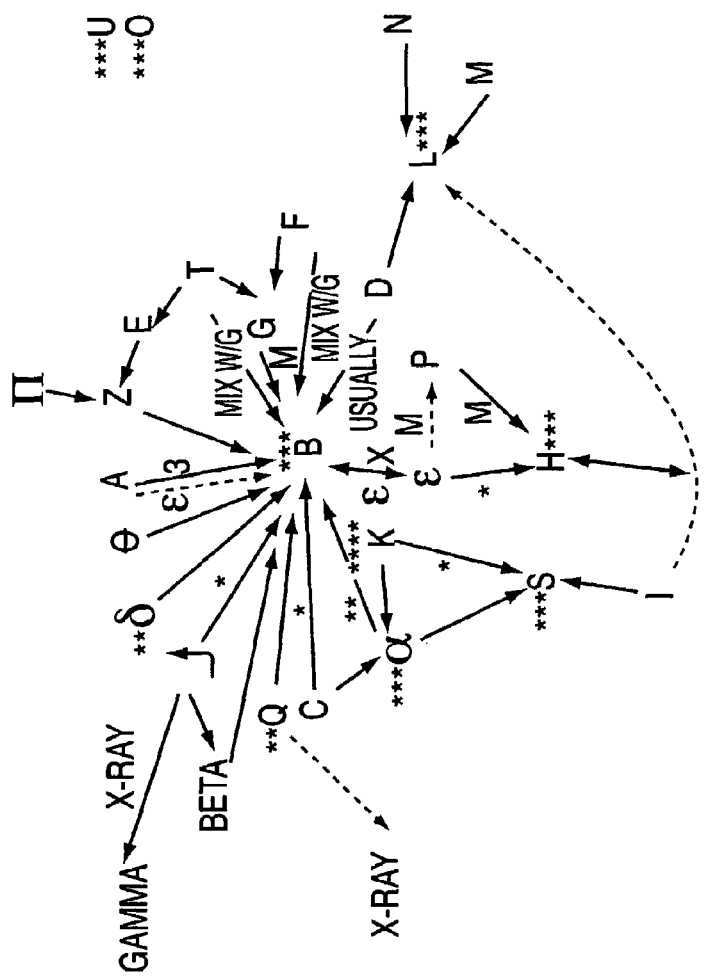
FIG. 28 is a thermal stability chart showing transformation of the forms during drying, and is a summary of a comparison between the wet and the dry forms illustrated in various tables in the present invention.
Figure 29:
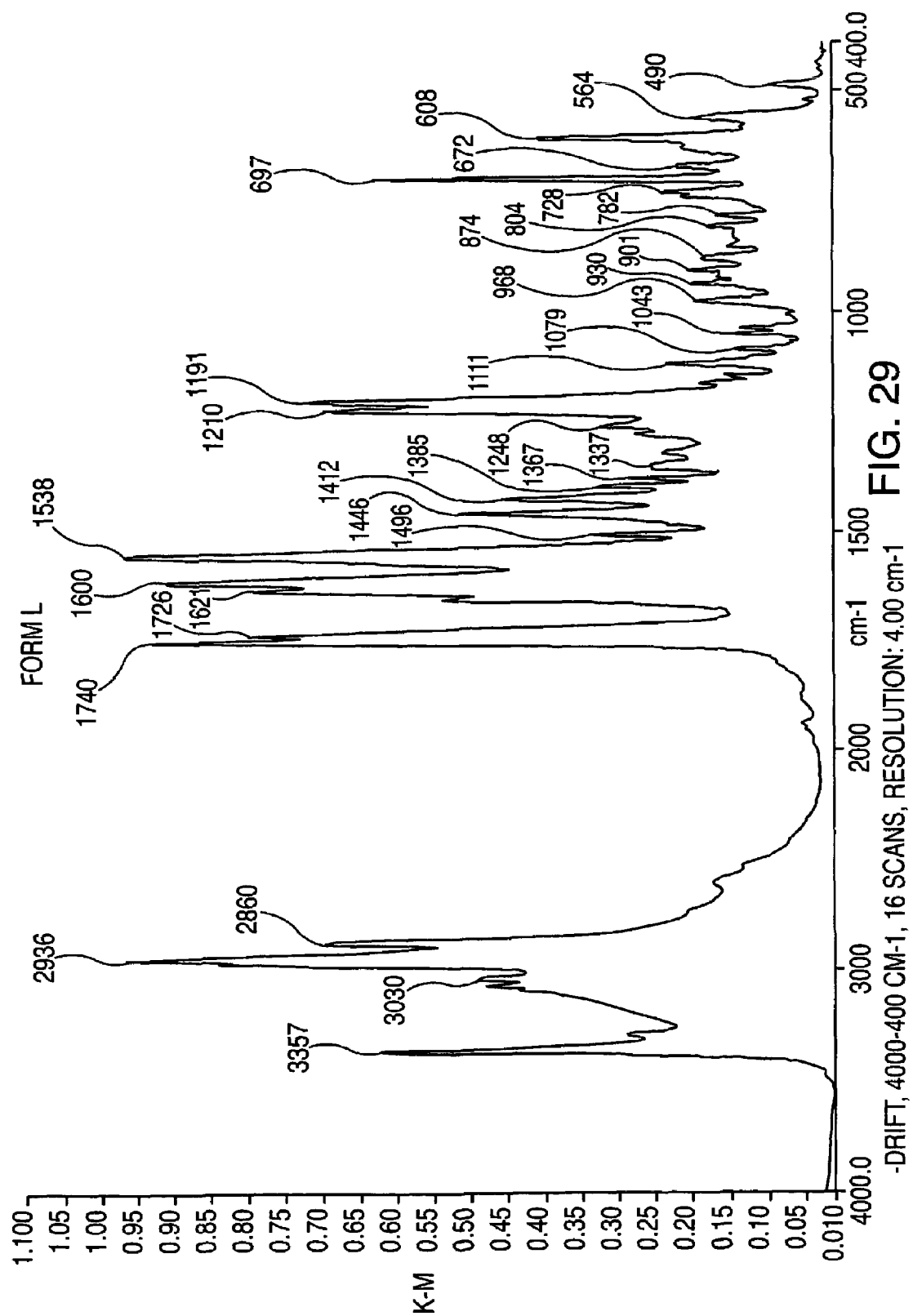
FIG. 29 is an FTIR spectrum of nateglinide Form L.
Figure 30:
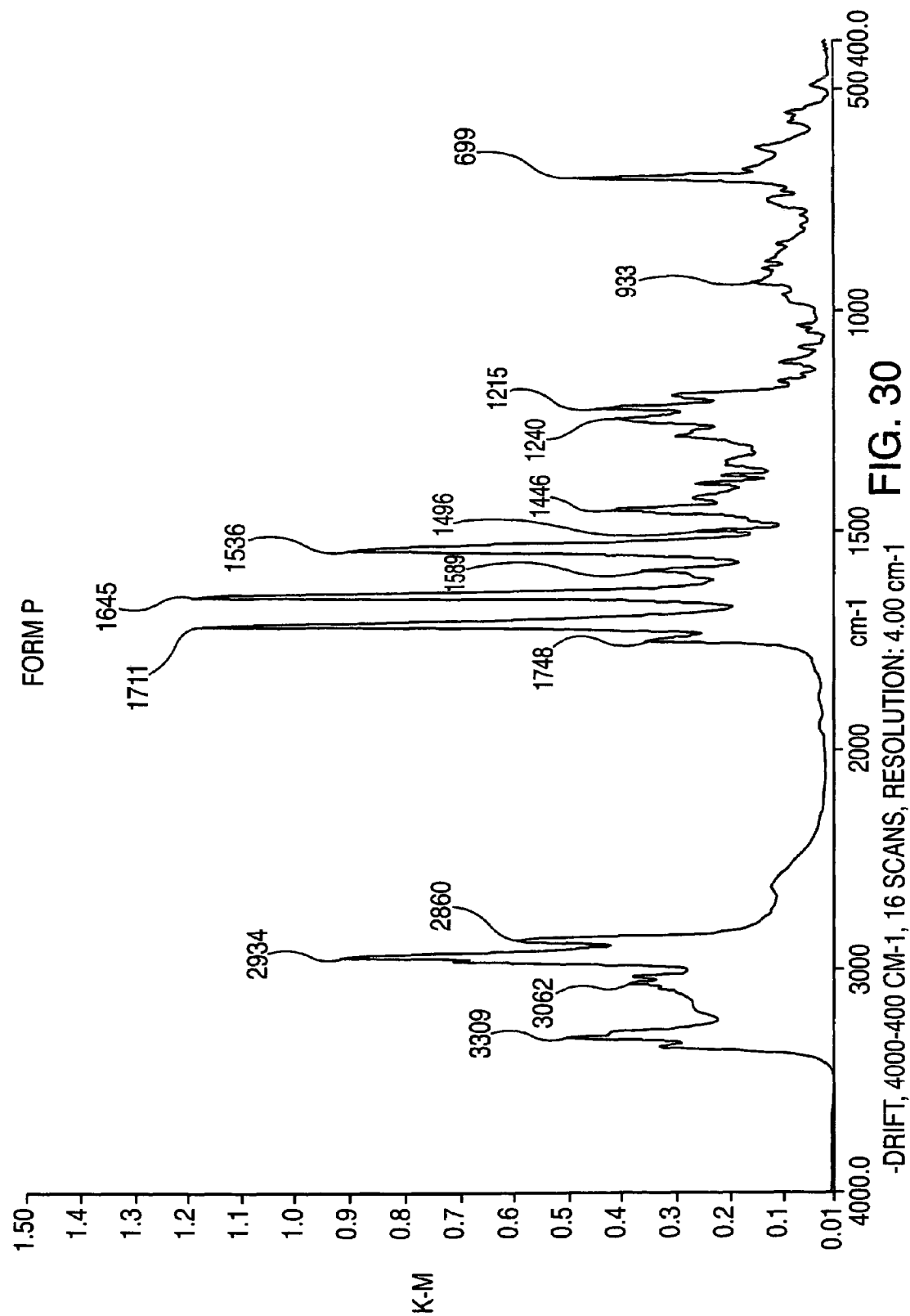
FIG. 30 is an FTIR spectrum of nateglinide Form P.
Figure 32:
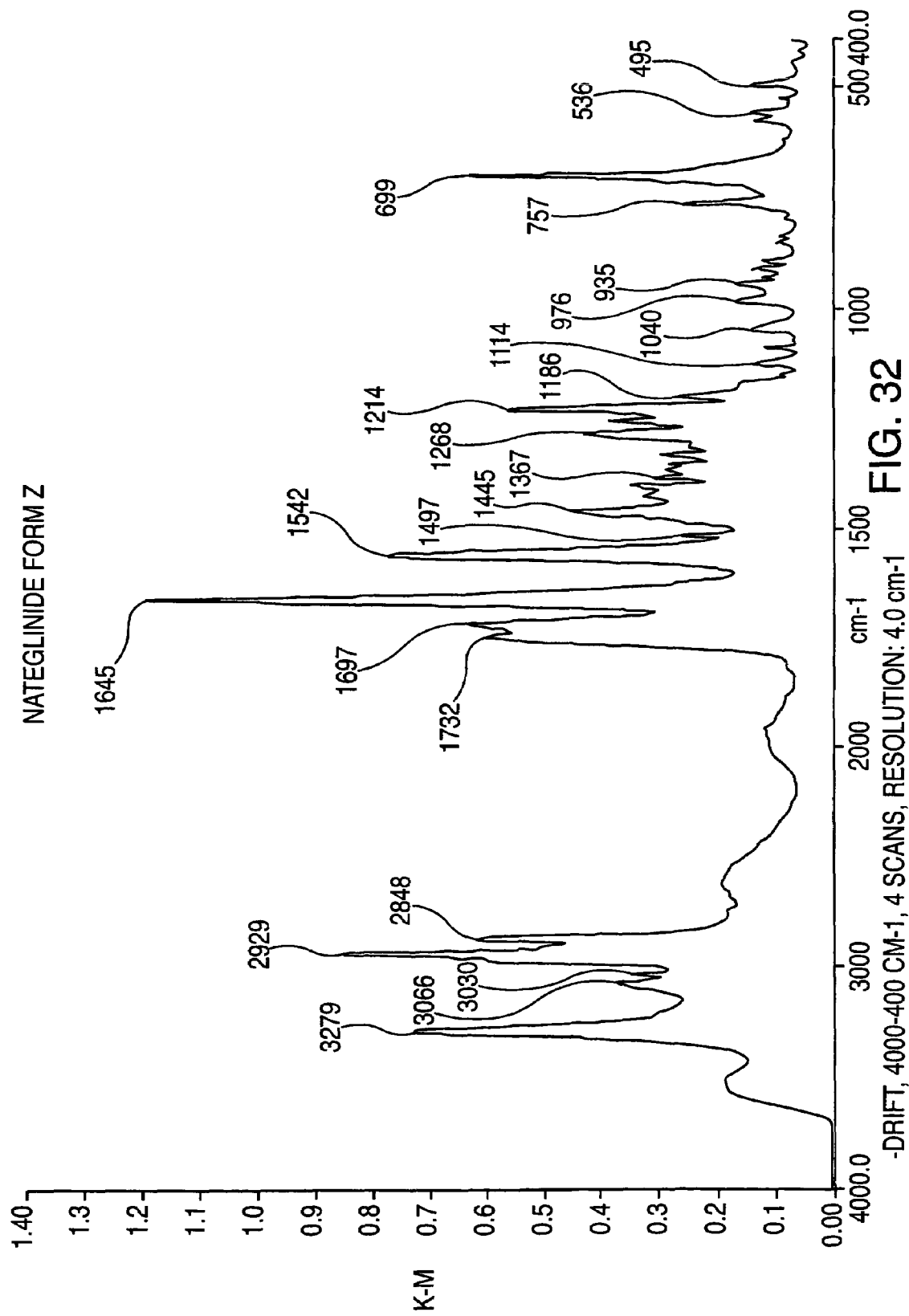
FIG. 32 is an FTIR spectrum of nateglinide Form Z.
Figure 33:
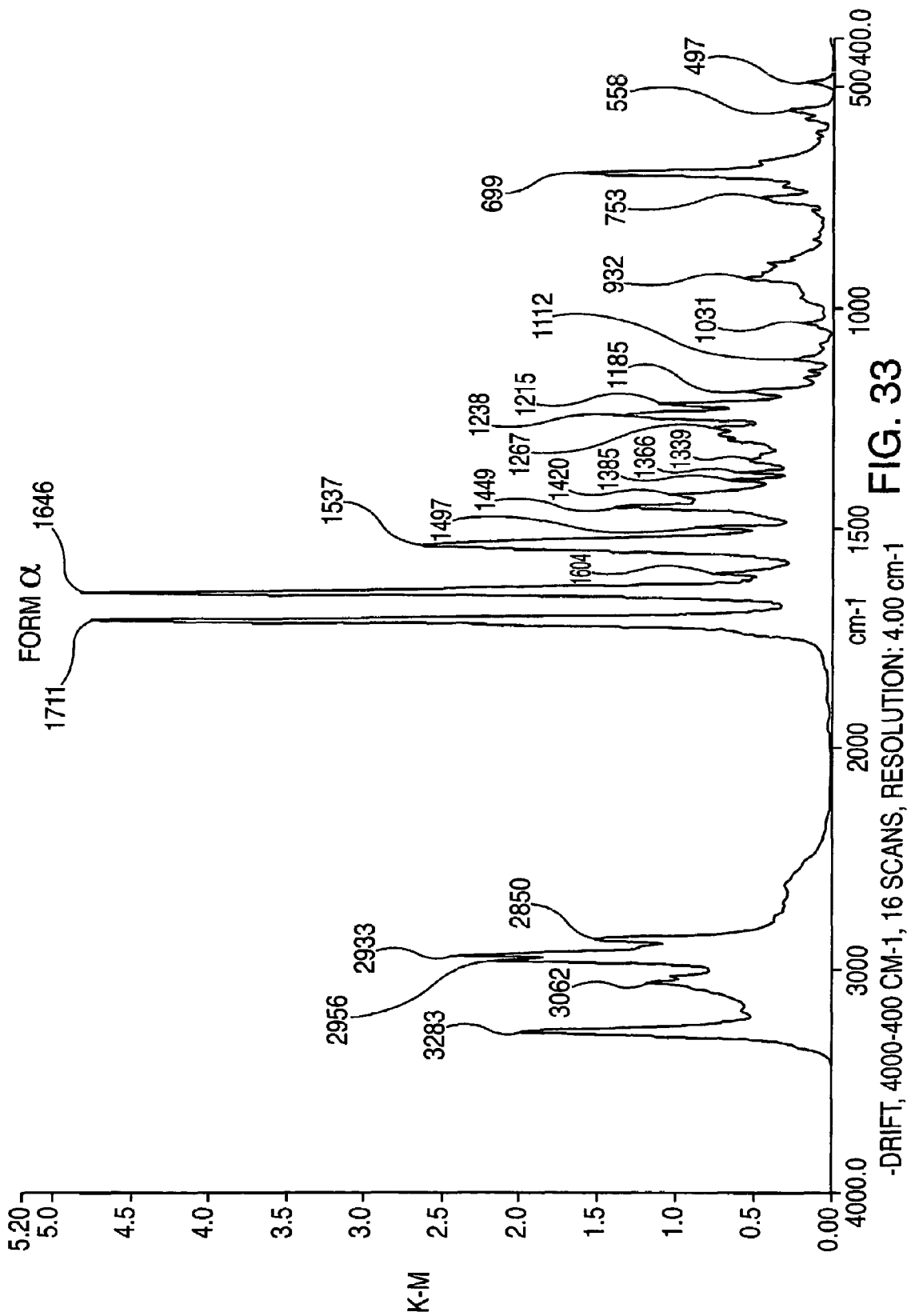
FIG. 33 is an FTIR spectrum of nateglinide Form α.
Figure 34:
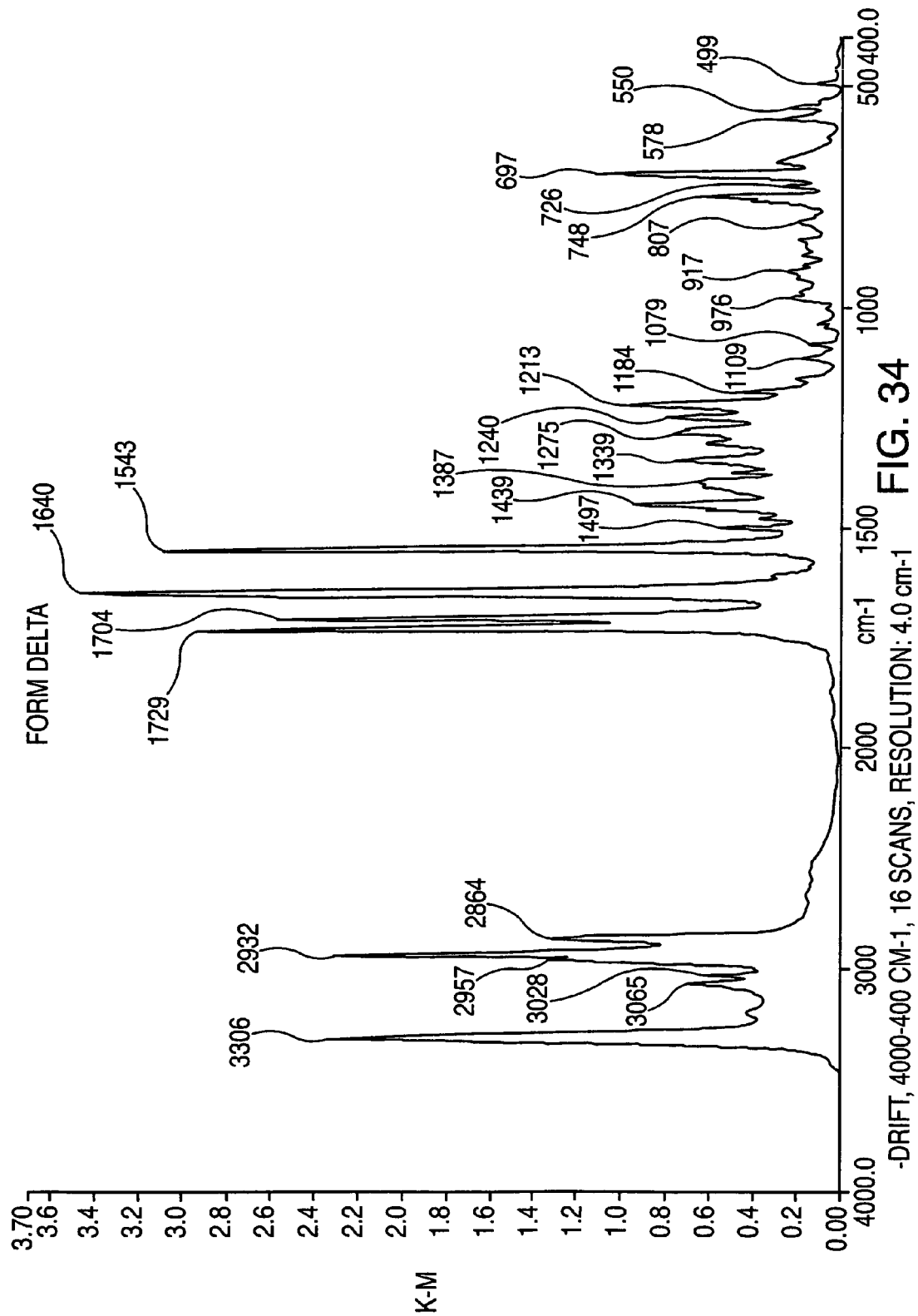
FIG. 34 is an FTIR spectrum of nateglinide Form δ.
Figure 35:
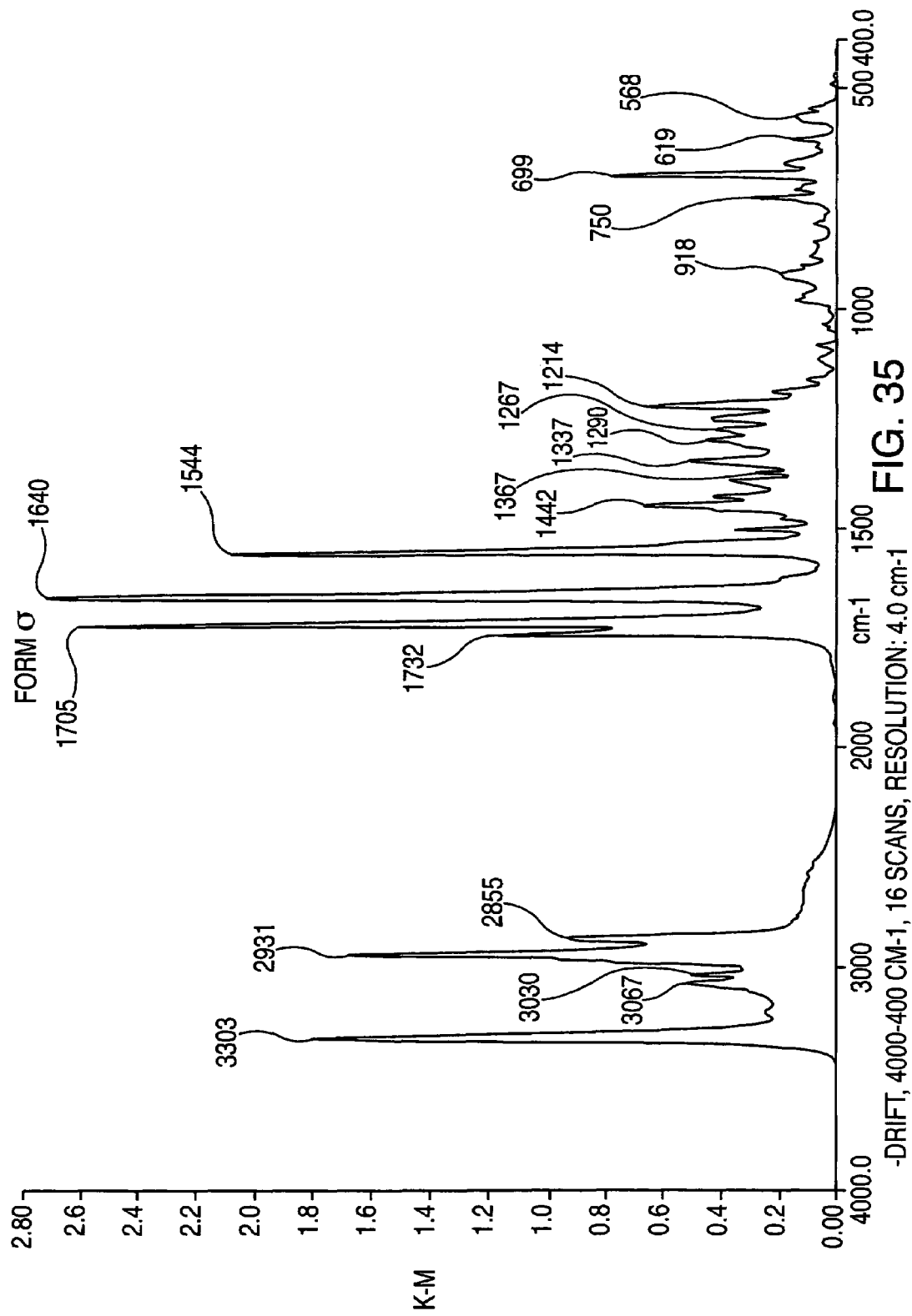
FIG. 35 is an FTIR spectrum of nateglinide Form σ.

| nateglinide form | Characteristic FTIR Peaks |
| --- | --- |
| Form Alfa: | 3283, 1711, 1646, 1420, 1238 cm$^{-1}$ (FIG. 32) |
| Form L: | 1741, 1726, 1621, 1600, 1538, 1211, 1191 cm$^{-1}$ (FIG. 28) |
| Form U: | 3350, 1701, 1646, 1291 cm$^{-1}$ (FIG. 30) |
| Form δ: | 3306, 1729, 1704, 1275 cm$^{-1}$ (FIG. 34) |
| Form σ | 3303, 1705, 1640 cm$^{-1}$ (FIG. 35) |
| Form P: | 3309, 1748, 1589 cm$^{-1}$ (FIG. 29) |

The various crystalline forms are related to each other in that drying of one form may result in a transformation to another form, namely nateglinide Forms A, B, D, E, F, G, H, I, J, K, L, M, N, Q, S, T, V, Z, α, β, δ,γ, ε, θ and Ω. The drying is carried out by heating a sample under ambient or reduced pressure. Generally, a preferred temperature is from about 40° C. to about 80° C., more preferably under reduced pressure. Of these forms, Forms B, H, L, U and sigma are thermally stable, and do not convert to another form upon heating. Many of the above forms convert to Form B upon drying, namely Forms A, C, D, E, F, G, J, K, P, Q, T, Z, α, β, δ, θ and Ω. Of these forms, Form α, δ, Y and O are somewhat stable, and usually retain their crystalline structure after heating, unless heated to a high temperature. For example, Form δ is stable when heated to 60° C. overnight (at least about 8 hours), but heating of Form δ at 120° C. and 1 atmosphere results in Form B. Thus, heating at a temperature above about 80° C. may cause a transformation in these forms. The term "stable" as used herein refers to a polymorphic change of less than about 5% by weight, more preferably less than about 2%, particularly for Form δ.

The conversion of some of the forms to Form B goes through another form. For example, the conversion of Form K and E to Form B may go through Form Z.

Form G may represent a link between Forms F, T on the one hand, and Form B on the other hand. Forms T and F, upon drying, convert to a mixture of Form B and G, which makes is probable that Forms F and T convert to Form B by going through Form G.

Of the forms that convert to Form B, some of them sometimes under drying convert to other forms. Form K may convert to Forms α or S, while Form C may convert to Form B or α. Form α may convert to Form S upon heating, but the presence of seeds of Form B in the sample of Form α results in Form B. Probably Forms C and K transform to Form α first, and that it is through Form α that they transform to Form B or S. Form J may convert to Form B or β, though its conversion to Form B may go through Form β. The Form J used in preparing Form β is preferably obtained by crystallization from N-methylpyrrolidone. When Form J contains some seeds of Form γ, heating results in Form γ.

The acetonitrile solvate of Form Epsilon, when dried, results in Form B. While the nitromethane solvates of Form Epsilon when dried result in Forms H or P. When Form P is dried, Form H is obtained, which makes it probable that conversion of Form Epsilon to Form H goes through Form P.

Another thermally stable Form of nateglinide is Form L. Form L may be obtained by heating Forms M, N and D. To obtain Form L, these various forms are preferably heated for about 3-10 hours at a preferred temperature range of from about 40° C. to about 80° C., more preferably about 50° C. under reduced pressure. Form γ may also be prepared by heating Form J containing seeds of Form γ under similar conditions.

Another thermally stable form of nateglinide is Form H which may be prepared by heating nateglinide Forms P, V and ε. Form S may be prepared by heating Forms α and K, though the transition of Form K to Form S may go through Form α.

Form U is another thermally stable Form of nateglinide, and does not undergo a transition after being heated at about 100° C. for at least about 8.5 hours.

Storage at room temperature and pressure may also cause a transition of one form to another. Form A partially converts to Form B during storage at room temperature for about a day. Form I converts to Form L under the same conditions. Also under the same conditions, Form Q converts to Form Y (containing chloroform), while Form T converts to Form E.

Form α is related to Forms F, G, I and ε in that it may be crystallized out of the same solvent as those forms, n-propanol, isopropyl alcohol, n-butanol and acetonitrile, respectively. Form a however is crystallized under different conditions, see e.g., Table IV. Form α is often obtained with prolonged crystallization step (at least about 2-3 days). Not being bound by any theory, this phenomenon may point to a possible conversion of another crystalline form, such as those obtained from the same solvent, to Form α overtime in the solvent.

Forms E and D are also related in that both of the forms may be crystallized out of ethanol; but these forms crystallize under different conditions, see e.g., Table IV. The crystallization of Form E in ethanol is prolonged, for at least about 5 days, more preferably at least about 1 month. Not being bound by any theory, it might be possible that initially Form D crystallizes out, followed by a conversion to Form E overtime in the solvent.

To prepare Form S, the wet sample obtained after crystallization has to be dried. Crystallization from a solution of nateglinide in n-butanol and DMF results in a solvate, which needs to be dried to obtain Form S. The wet samples are nateglinide Forms K, I and alpha.

Some of the forms may first appear as a gel, and then transform into crystals during the filtration step (e.g. form epsilon from nitromethane, and form A from xylene) or overtime (e.g. Form M from carbon tetrachloride and Form J from N-methylpyrrolidone). Generally, gels are unstable forms which crystallize over time.

Some of the crystalline forms may be obtained by trituration. As used herein, trituration refers to obtaining a solid from a mixture of nateglinide in a solvent without complete dissolution. A form of nateglinide is mixed in a particular solvent and agitated for a sufficient time to allow for transformation to another crystalline form. After agitation, a suspension or a paste forms. A solid may then be separated from the suspension by techniques well known in the art, such as filtration. The paste may be filtered, to name one technique, to remove excess solvent. The result of this trituration procedure is various forms of nateglinide.

The trituration of Form delta in water may result in Form Z after about 5 hours, and Form E after about 8 hours, which may also point to a transition of Form Z to Form E. All three forms may be heated to obtain Form B.

Some of the crystalline forms may be obtained by solvent removal. First a solution of nateglinide in a suitable solvent is prepared. The solvent may be heated to obtain a clear solution. The solvent may be heated from about 40° C. to about 70° C., with about 55° C. being preferred. The solvent is then removed to obtain a residue, preferably at elevated temperature within the said range. The solvent is preferably removed by evaporation, with evaporation under reduced pressure being particularly preferred. The resulting residue is then examined. Suitable solvents include esters, ketones, amines, amides, alcohols and nitriles. Removal of acetonitrile, acetone, ethyl acetate and iso-propyl alcohol as solvents results in nateglinide Form B.

Some of the crystalline forms are obtained by absorption of solvent vapors. Nateglinide is contacted with vapors of a particular solvent, resulting in absorption of the solvent. Absorption of ethanol results in Form D, methanol in Form O, and DCM in Form Y. Form H was stable in the presence of vapors of water and acetone.

Some of the crystalline forms may be obtained by crystallization from a suitable solvent. Form omega is obtained by crystallization of nateglinide out of a mixture of water and isopropanol. Preferably, the ratio of the water to isopropanol is from about ½ to about ⅕, more preferably ⅓ (vol/vol).

Nateglinide Form Z is generally prepared by acidification of a solution of an alkali metal or alkaline earth metal salt of nateglinide in an aqueous solvent. Preferred solvent is water free of a co-solvent. Preferred salts are sodium and potassium salts, with the sodium salt being most preferred. Before acidification, the solution preferably has a pH of above about 8, while after acidification, the pH is preferable from about 1 to about 5, most preferably from about 2 to about 5. Acidification results in precipitation of nateglinide, which may be recovered by techniques well known in the art, such as filtration.

Nateglinide Forms B and U may be prepared by crystallization from an organic solvent such as ethyl acetate or acetone. In the procedure for the preparation of form B, crystallization is preferably induced by concentration of the solvent, while for Form U, by seeding of the solution.

Nateglinide Forms B, H, U, Z, δ, θ and σ are related in that all of them may be prepared from a two solvent system. The two solvent system used is a mixture of a solvent and an anti-solvent. Example of suitable antisolvents are $C_5$ to $C_{12}$ aromatic hydrocarbons such as toluene and xylene, and $C_5$ to $C_{12}$ saturated hydrocarbons such as hexane and heptane. Examples of suitable solvents are $C_1$ to $C_5$ alcohols such as methanol, ethanol, isopropanol, n-butanol and n-propanol, lower ketones ($C_3$ to $C_6$) such as acetone and lower esters ($C_3$ to $C_6$) such as ethyl acetate. After crystallization, the crystals are recovered by techniques well known in the art, such as filtration and centrifugation, and may be dried. To dry, the temperature may be increased or the pressure reduced. In one embodiment, the crystals are dried at about 40° C. to 60° C., at a pressure of less than about 50 mmHg.

When nateglinide is crystallized out of a binary mixture, particularly in the absence of stirring, the crystalline product is often Form B, as illustrated in Table IX. The binary mixture is prepared by suspending nateglinide in the anti-solvent, and then adding the solvent to form a solution. Nateglinide Form B may be obtained at different crystallization temperatures, such as at room temperature and at about 0° C., particularly in the absence of stirring.

Crystallization from a binary mixture of the above solvents and anti-solvents may lead to other forms of nateglinide other than Form B. Crystallization out of a toluene/methanol mixture may result in nateglinide Form E, which may be converted to Form B by heating. Additionally, a heptane/ethyl acetate combination may sometimes lead to a mixture of Forms B and Z, especially with longer period of crystallization (over about 3 days), while a toluene/ethyl acetate mixture may result in a mixture of Form B and H. A mixture of Form B and Z may be converted to one containing substantially Form B through heating, since Form Z converts to Form B through heating.

In another embodiments, rather than preparing a solution by first suspending nateglinide in the anti-solvent, a solution is prepared in the solvent, followed by combining with the anti-solvent. The combining is carried out in this embodiment in such a way where upon additon a solution is formed, and any precipitated solids go back into solution. Preferably, the anti-solvent is heated so that upon mixing of the solution and the anti-solvent, immediate precipitation does not take place.

The different forms may be obtained depending on the solvent/anti-solvent ratio, crystallization conditions and the time of stirring. Generally, Form Z is crystallized from an ethyl acetate/heptane ratio of about 2 to 4, form H a ratio of about 4 to about 7, Form B a ratio of about 6 to about 8, Form U a ratio of about 1 to about 2, Form θ a ratio of about 1 and Form δ a ratio of about 1 to about 8, more preferably from about 1 to about 2 (vol/vol).

Of these, some forms may crystallize as other forms, and convert after being stirred for a sufficient time in the solvents. Stirring the resulting slurry from crystallization at a temperature of from about −15° C. to about 10° C., preferably about 5° C., may result in Form δ. Form δ seems to result from stirring of forms such as Form U, Form θ, Form H and even Form B. Preferably the stirring to obtain Form δ is carried out for at least about 2-3 hours, more preferably for at least about 10 hours.

Other than a solvent:antisolvent ratio of about 1, formation of Form θ seems to be favored at lower crystallization and filtering temperatures, from about −15° C. to about 10° C. preferably 5° C. As previously noted, stirring of Form θ, preferably at the specified temperature range, results in Form δ.

Form U may be obtained by stirring with Form B or H in an organic solvent. Stirring for about 1 hour is sufficient to obtain Form U. However, additional stirring, such as above about 5 hours, may result in a transition to Form δ. Form U may also be obtained by crystallization, preferably at the specified ratio, more preferably at a crystallization and filtering temperature of about −15° C. to about 10° C. Form U is generally favored when starting with a temperature of from about 25° C. to about 35° C., followed by cooling in less than about 1 hour to a temperature of from about 0° C. to about 10° C., with about 5° C. being preferred, followed by filtering in less than about 1 hour. Higher solvent to anti-solvent ratio may favor form U over θ.

Form H may be obtained under both low and high crystallization temperatures, preferably under the specified solvent/anti-solvent ratio. Form B, on the other hand, tends to crystallize at a temperature of at least about 15° C.

Forms Z generally crystallizes after about a day at a final crystallization temperature of at least about 15° C., more preferably from about 15° C. to about 30° C., and most preferably from about 20° C. to about 25° C. The initial crystallization temperature for these forms is preferably above 35° C., followed by cooling in a few hours, more preferably about 1 hour, to about 20° C. to about 25° C. These conditions may lead to Form Z, which converts to Form B by drying.

Form σ may also be obtained by stirring of crystals of Form B. Not being bound by any theory, it may be possible that Form σ is obtained through Form U, that is stirring results in a transition of Form B to Form U followed to Form σ. Prolonged crystallization and filtration is preferred for obtaining Form σ, i.e., preferably at least about 10 hours.

Table X does not show a transition of Form B to other forms despite prolonged stirring in the anti-solvent/solvent system due to use of a high ratio of ethyl acetate. Preferably about a 1:1 ratio of solvent to anti-solvent is used for obtaining other forms through stirring of Form B in a solvent/antisolvent mixture.

The results of the processes may vary when precipitating a solid after combining the solution and the anti-solvent. In this embodiment, the solution is combined with the anti-solvent in such a way to result in precipitation, in contrast with the other embodiments that result in a solution after the combining step. To cause substantial precipitation, preferably, the solution is combined with a cold anti-solvent. More preferably, the antisolvent is from about 20° C. to about 40° C. colder than the solution, particularly when an ethyl acetate/heptane system is used. Most preferably, the heptane has a temperature of from about 0° C. to about 10° C. and the ethyl acetate a temperature of from about 30° C. to about 40° C.

In this embodiment, Form U may be obtained within a wide range of solvent/anti-solvent ratios and crystallization temperatures. For example, table XI shows that Form U may be obtained from a solvent to anti-solvent ratio of from about 1 to about 6, and final crystallization temperatures from about 0° C. to about 30° C. Not being bound by any theory, the presence of other forms, particularly Form δ and σ, especially after long crystallization step, points to possible a transition of Form U to these forms. The presence of a mixture of Form B and U after 1 hour also points to the possibility that Form B might be immediately crystallized out of the solution, followed by a transition to Form U, which itself may change overtime to Forms δ or σ.

The following table provides guidance on obtaining Forms B, H, U, Z, δ, θ and σ from a solvent:anti-solvent system:

| V/V ratio (EA/Heptane) (about) | Filtration temp. (about) | | | Crystal form obtained |
|---|---|---|---|---|
| 1:1 | 15° C.-30° C. preferably 20-25° C. | No stirring | | B |
| 1:1 | 15° C.-30° C. preferably 20-25° C. | With stirring | Immediately after crystallization | B |
| | | | Stirring for at least about 21 h | σ |
| 1:1 | 15° C.-30° C. preferably 20-25° C. | Precipitation without going into solution after combining | Immediately after crystallization | B |
| | | | Stirring for at least about 1 h | U |
| 1:1 | −15° C.-10° C. preferably 5° C. | | Immediately after crystallization | Drying θ → B |
| | | | Stirring at about 5° C. | δ |
| 1.5:1 | −15° C.-10° C. preferably 5° C. | | Immediately after crystallization | U |
| | | | Stirring at about 5° C. | δ |
| 2:1-8:1 | −15° C.-10° C. preferably 5° C. | | Immediately after crystallization | H (95% yield) |
| | | | Stirring for about 1-5 h | U |
| | | | Stirring for at least about 5 h | δ |
| 2:1-8:1 | 15° C.-30° C. preferably 20-25° C. | Wet crude material | | Drying Z → B |
| 2:1-8:1 | 15° C.-30° C. preferably 20-25° C. | Dry crude material | | H |

In a refinement of the above processes for preparing Form U, nateglinide Form U may be prepared by dissolving nateglinide (any form, crystalline or amorphous) in a relatively small amount of ethyl acetate, in the ratio of about 3 to about 11 mL/g, more preferably about 4 to about 6 mL/g ratio. A clear solution is obtained by heating the mixture to a preferred temperature of about 25° C. to about 47° C. It is possible to use a larger quantity of solvent to dissolve nateglinide without heating, however the range of about 3 to about 11 mL/g is preferred since inducing crystallization is simply done by seeding and optionally cooling, while large volumes may involve more complicated ways of inducing crystallization. The solution is preferably filtered to remove insoluble matter. The solution is seeded with nateglinide crystals, preferably Form U crystals (in order to ensure that the final material is consistently crystallized in form U), preferably at a temperature of about 13 to about 35° C., more preferably a temperature of about 25° C. to about 35° C. Cooling to about −10° C. to about +10° C. may be used to increase the yield. Cooling may be done before or after seeding. The crystals are isolated by conventional methods such as filtration. The crystals obtained (form U) may be dried using conventional techniques, such as vacuum drying (stirred or static). Nateglinide crystals obtained from this process are chemically pure (More than 99% pure as area percentage HPLC). Table U-I summarizes the main parameters ranges used for the preparation of nateglinide Form U in ethyl acetate, and table U-II gives details of the parameters of the different experiments.

TABLE U-I

Range of process parameters for crystallization in ethyl acetate:

| Parameter | Range (about) |
|---|---|
| Volume of solvent/Unit weight of NTG | 3-11 |
| Dissolution temp. | 25-47° C. |
| Seeding temp. | 13-35° C. |
| Stirring time at seeding temp. | 0.5-8 hr |
| Cooling rate | 1.3-9.4° C./hr |
| Filtration temp. | (−10)-10° C. |
| Stirring time at filtration temp. | 2-14 hr |
| Drying temp. | 25-50° C. |

TABLE U-II

Details of the different experiments according to the above procedure

| Exp. | EA/NTG mL/g ratio | Dissolution Temp. (° C.) | Seeding Temp. (° C.) | Stirring Time (hr) | Cooling Rate (° C./hr) | Filt. Temp (° C.) | Stir. Time (hr) |
|---|---|---|---|---|---|---|---|
| #1 | 8/1 | 40 | 24.5 | 0.5 | 8.16/1 | 0 | 2 |
| #2 | 11/1 | 25 | 15 | 1 | 1.5/1 | 0 | 8 |
| #3 | 5/1 | 44.5 | 25.5 | 0.5 | 9.16/1 | −2 | 2 |
| #4 | 5/1 | 47 | 35.5 | 0.5 | 9.4/1 | −2 | 2 |
| #5 | 5/1 | 45 | 35 | 0.5 | 3.7/1 | −2 | 14 |
| #6 | 5/1 | 44 | 25 | 8 | 9/1 | −2 | 10 |
| #7 | 4/1 | 35 | 25 | 3 | 1.3/1 | 2 | 0 |
| #8 | 5/1 | 40 | 25 | 0.5 | 1.5/1 | 10 | 9 |
| #9 | 5/1 | 40 | 25 | 0.5 | 3.5/1 | −5 | 9 |
| #10 | 8/1 | 39 | 13 | 0.5 | 3.5/1 | −10 | 14 |

In another refinement of the above process for preparation of Form U, nateglinide (any form, crystalline or amorphous) is dissolved in ethyl acetate (about 4 volumes). The solution is heated, for instance to about 30° C. to about 50° C., more preferably about 45 to about 50° C., and a clear solution is obtained. The solution is preferably filtered to remove insoluble matter. A $C_5$ to $C_{12}$ saturated hydrocarbon, such as heptane (about 5 to about 10 volumes), is added to the solution, while keeping the solution clear, for instance by controlling the temperature or by controlling the addition rate. In this embodiment, the solution is preferably in a container (e.g. reactor, flask), and the heptane is added to the container. The solution is then cooled to about 25 to about 44° C. and seeded in this temperature range with nateglinide crystals, while stirring. Cooling may be done before or after seeding. It is recommended to seed with form U in order to ensure that the final material is consistently crystallized as Form U. The mixture may be cooled to about 5° C. to about 10° C. to increase the yield, and then the crystals are recovered. The crystals obtained (Form U) may be dried using conventional techniques, such as vacuum drying (stirred or static).

Addition of a small quantity of water (about 2 to about 10% mL/g based on solid NTG) helps to improve the chemical quality (NMT about 0.15% of any impurity, preferably NMT about 0.1% of any impurity). Nateglinide Form U from this process may be made by dissolving nateglinide (any form, crystalline or amorphous) in ethyl acetate (4 volumes) containing about 2 to about 10% water (based on solid nateglinide), preferably about 4 to about 5%. The solution is heated, for instance to about 30° C. about 50° C., more preferably about 45° C. to about 50° C., and a clear solution is obtained. The solution is preferably filtered to remove insoluble matter. Heptane (about 5 to about 10 volumes) is added, keeping the solution clear, for instance by controlling the temperature or controlling the addition rate. The solution is then preferably cooled to a temperature of about 25° C. to about 44° C., and seeded at this temperature range with nateglinide crystals, while stirring. Cooling may be done before or after seeding. It is recommended to seed with Form U in order to ensure that the final material is consistently crystallized in Form U. The mixture may be cooled to about 5 to about 10° C. to increase the yield, and then the crystals are isolated. The crystals obtained (Form U) may be dried using conventional techniques. By using this process nateglinide crystals obtained are chemically pure (NMT about 0.15% of any impurity, more preferably NMT about 0.1% of any impurity).

Table U-III summarizes the main parameters ranges used for the preparation of nateglinide Form U using ethyl acetate and heptane (and water if chemical purification is needed).

TABLE U-III

Range of process parameters for crystallization in ethyl acetate/heptane

| Parameter | Range (about) |
|---|---|
| Water percent/Unit weight of NTG mL($H_2O$)/g(NTG) × 100% | 2-10% |

TABLE U-III-continued

Range of process parameters for crystallization in ethyl acetate/heptane

| Parameter | Range (about) |
| --- | --- |
| Heptane volume/Unit weight of NTG (mL/g) | 5-10 |
| Seeding temp. | 25-44° C. |
| Cooling rate | 1.65-19.5° C./hr |

The following table summarizes the various experiments used for the preparation of nateglinide Form U by using ethyl acetate (EA) water and heptane as described above.

TABLE U-IV

Details of the different experiments according to the above procedure

| Exp. | % Water/Unit weight of NTG | Hep/NTG ratio | Seeding temp. (° C.) | Stirring time at seeding temp. (hr) | Cooling Rate (° C./hr) |
| --- | --- | --- | --- | --- | --- |
| #1 | 2 | 5 | 44 | 0.5 | 19.5 |
| #2 | 10 | 5 | 25 | 0.5 | 10 |
| #3 | 10 | 5 | 27 | 0.5 | 14.66 |
| #4 | 10 | 5 | 31 | 0.5 | 13 |
| #5 | 4 | 10 | 40 | 0.5 | 1.65 |

From all the crystallization procedures in tables U-I through U-IV, nateglinide Form U is obtained with a purity of at least 99.5% (wt/wt) with respect to other polymorphic forms, e.g., Form H. The polymorphic purity of Form H, for example, can be monitored by X-Ray powder diffraction, by monitoring the typical peak of Form H at about 5.4 deg 2-theta.

Moreover form U is polymorphically stable (NMT 0.5 conversion to other poylmorphic forms, for example Form H), even in the presence of considerable relative humidity (75%), in particular under the conditions dictated by the ICH international standard (Q1A, "Stability testing of new drug substances and new products, $1^{st}$ edition Oct. 27, 1997 and $2^{nd}$ edition Nov. 8, 2000), recognized for the evaluation of the stability of pharmaceutical substances. Form U is polymorphically stable when stored for a period of at least about 6 months at about 40° C./75% RH, or about 25° C./60% RH. In addition, Form U is polymorphically stable at least 6 months when stored at a temperature of about 55° C.

Figure 1:
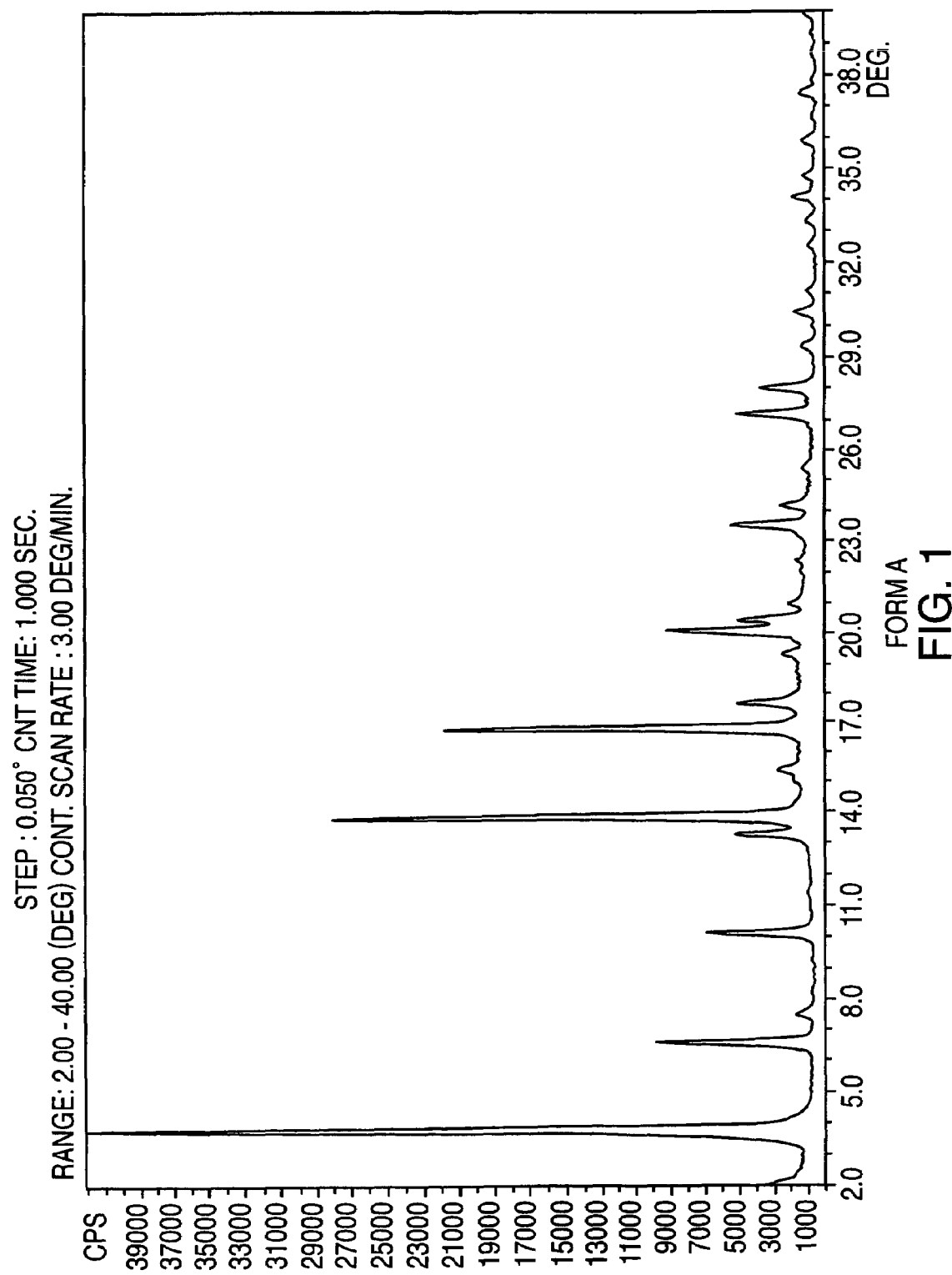
FIG. 1 is an XRPD pattern for nateglinide Form A.
Figure 2:
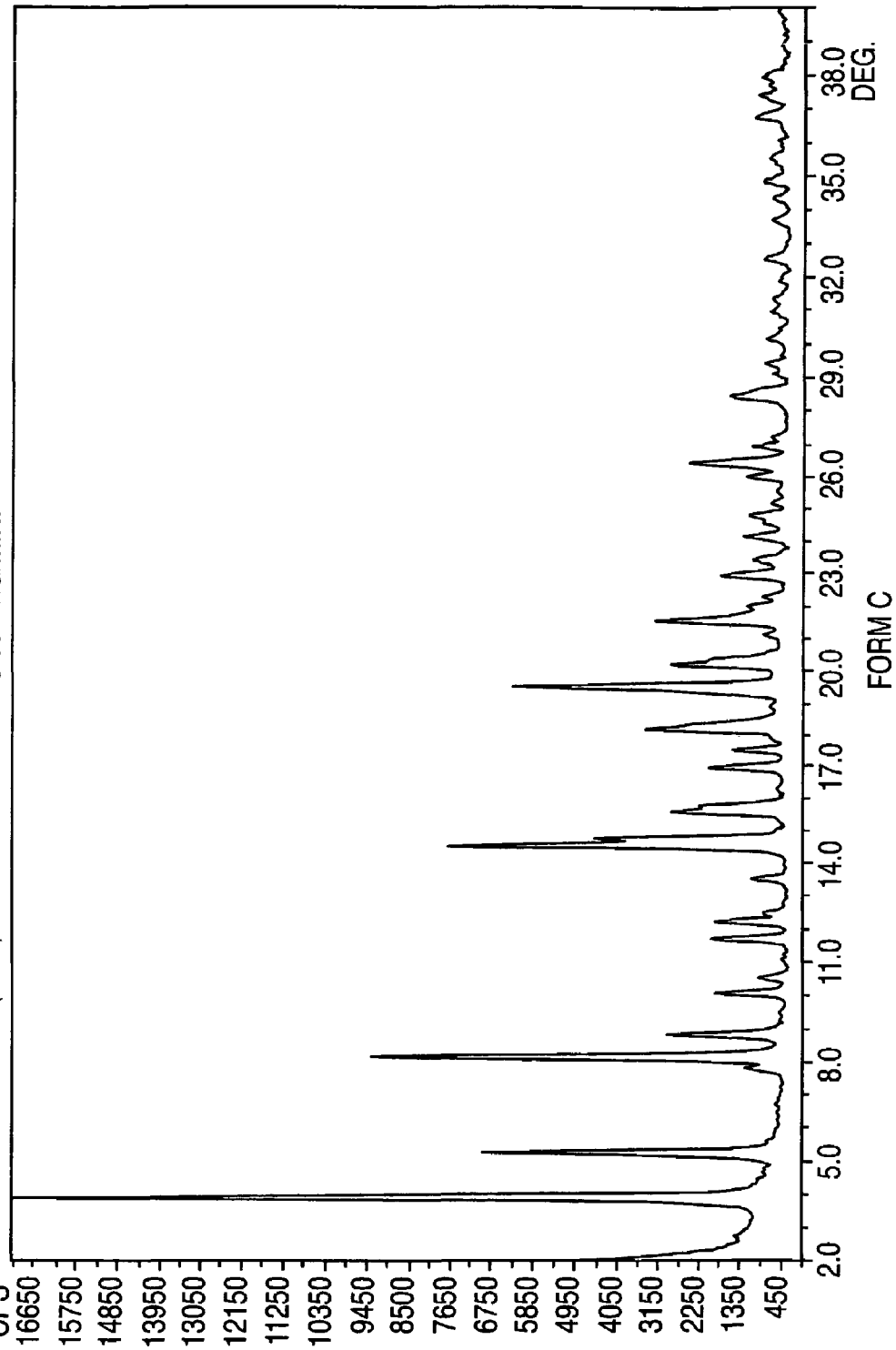
FIG. 2 is an XRPD pattern for nateglinide Form C.
Figure 3:
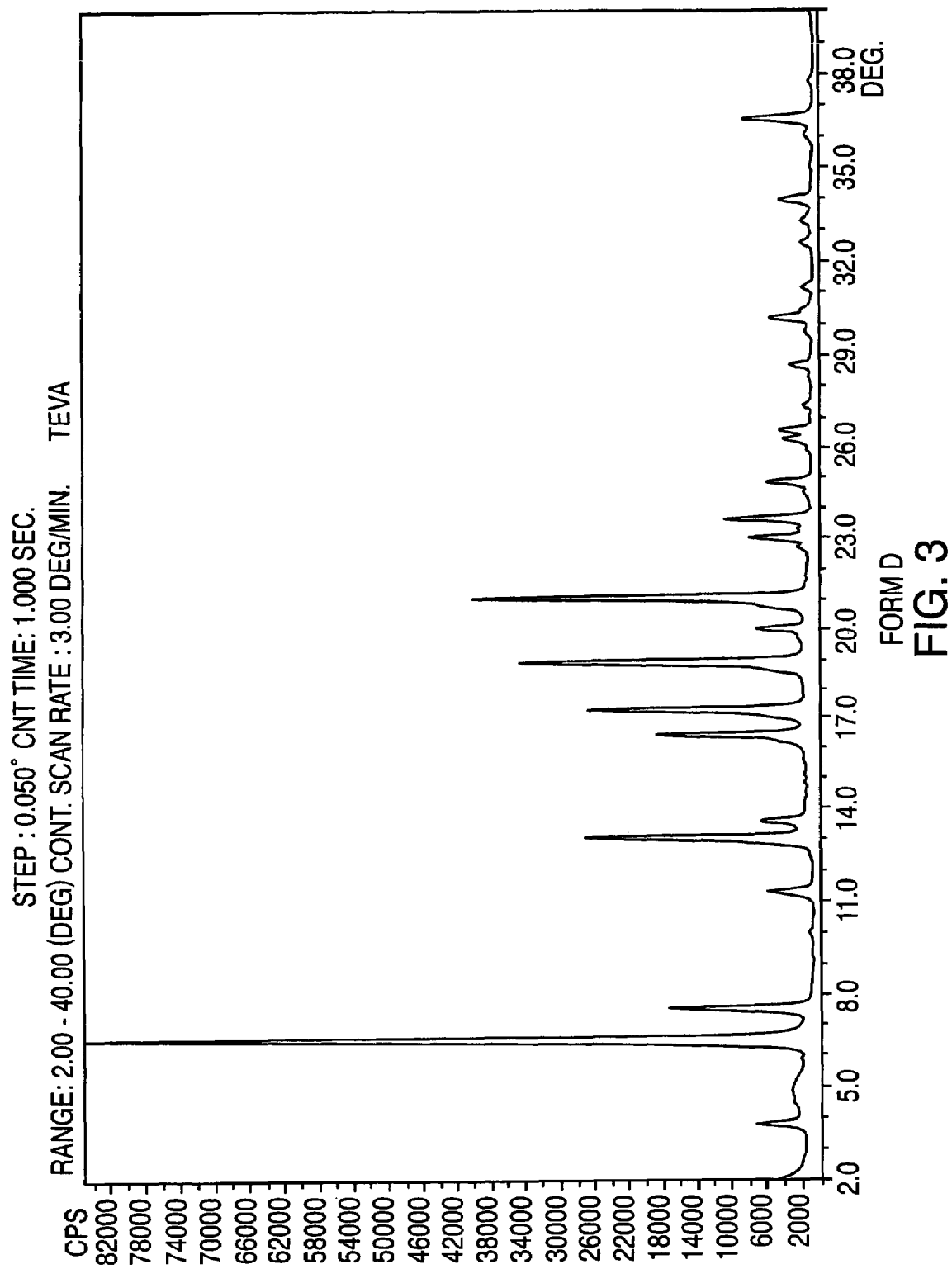
FIG. 3 is an XRPD pattern for nateglinide Form D.
Figure 4:
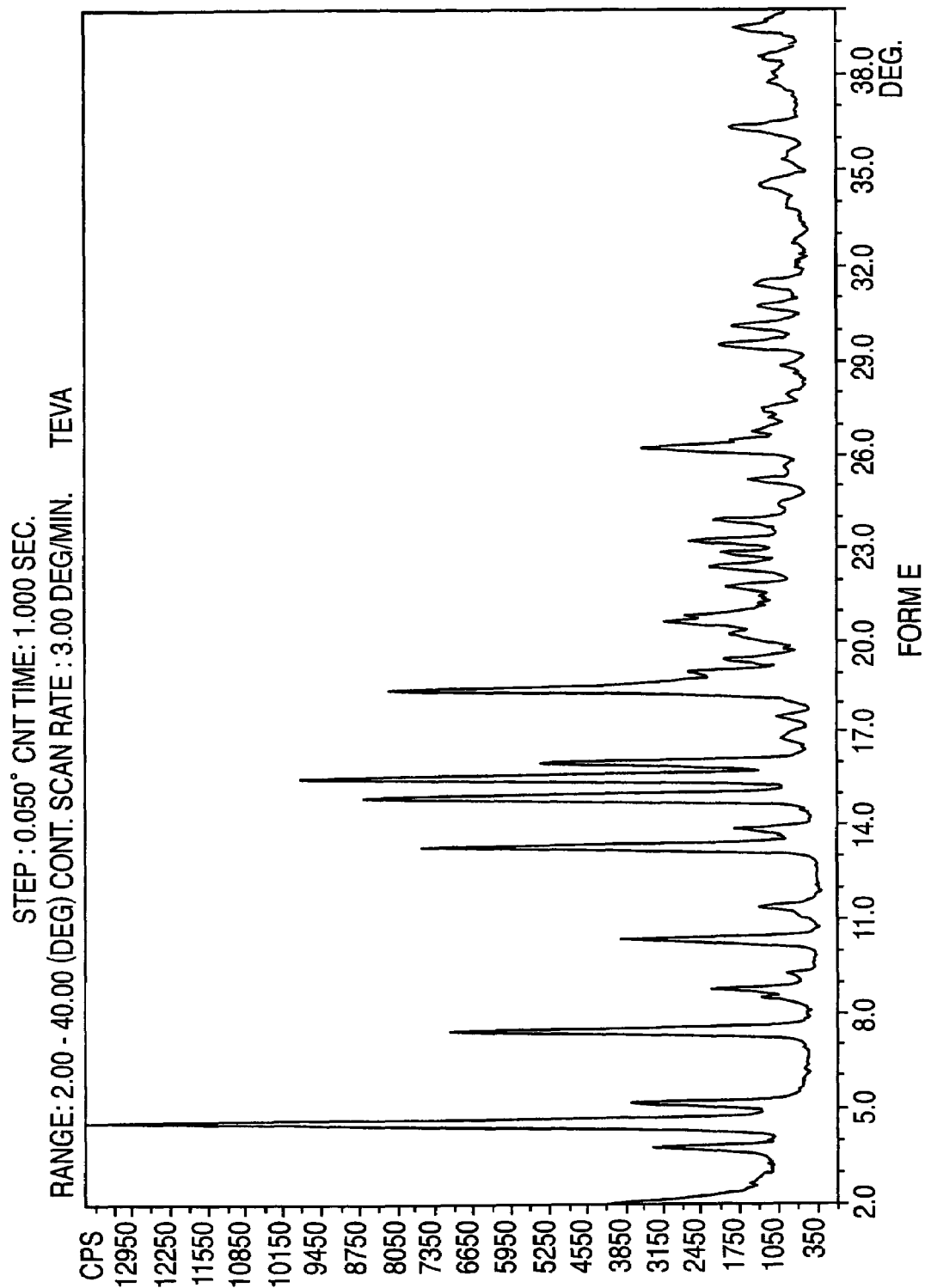
FIG. 4 is an XRPD pattern for nateglinide Form E.
Figure 5:
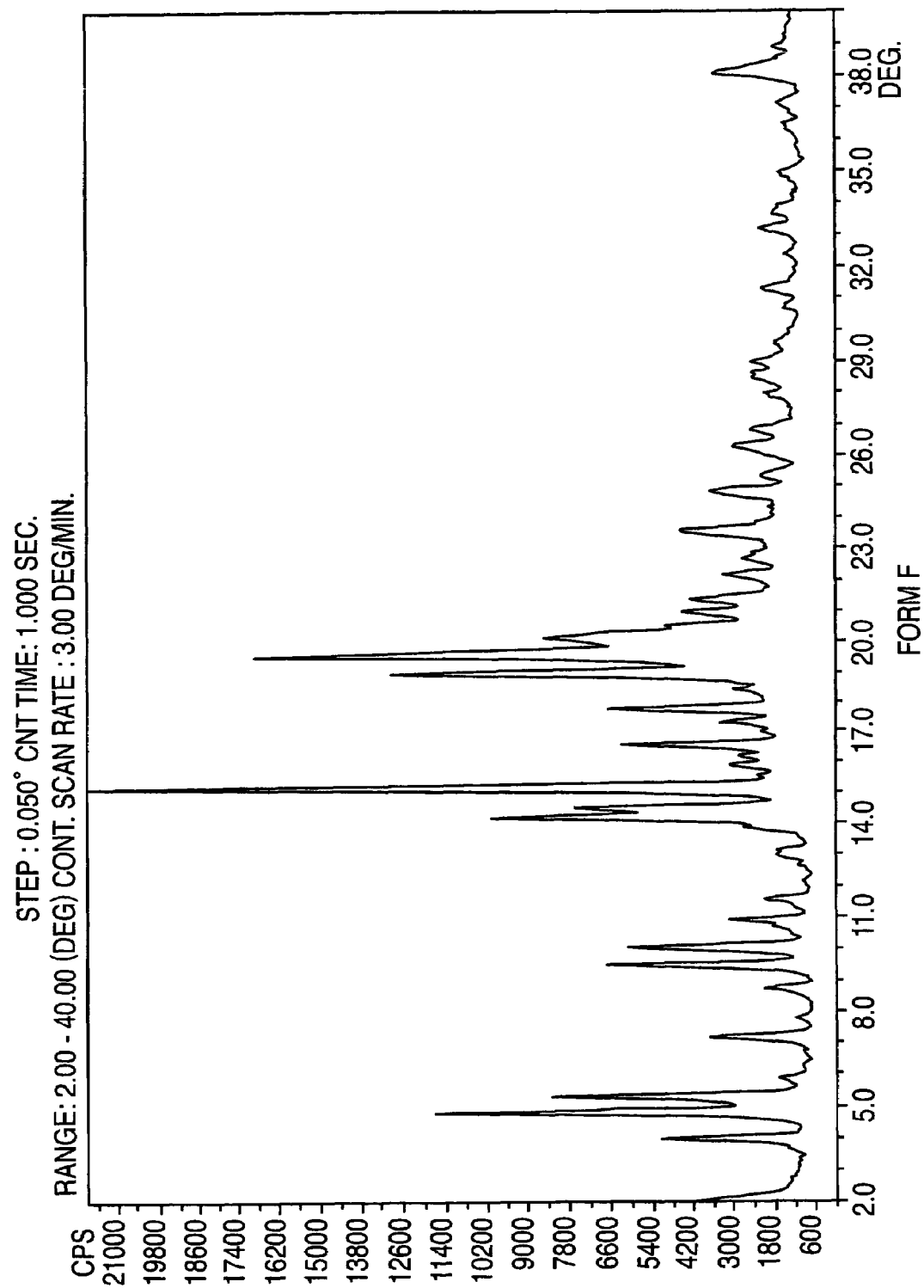
FIG. 5 is an XRPD pattern for nateglinide Form F.
Figure 6:
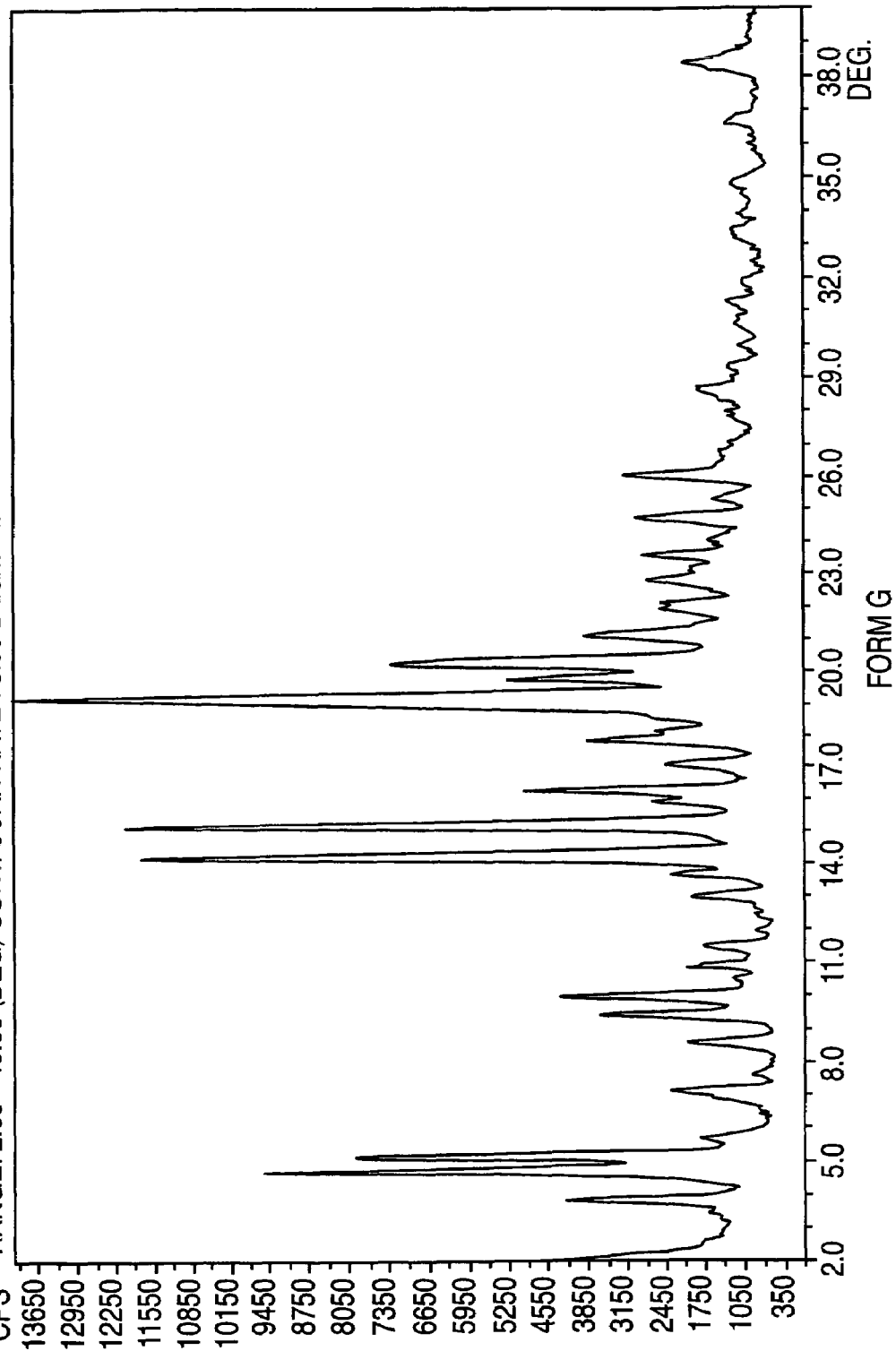
FIG. 6 is an XRPD pattern for nateglinide Form G.
Figure 7:
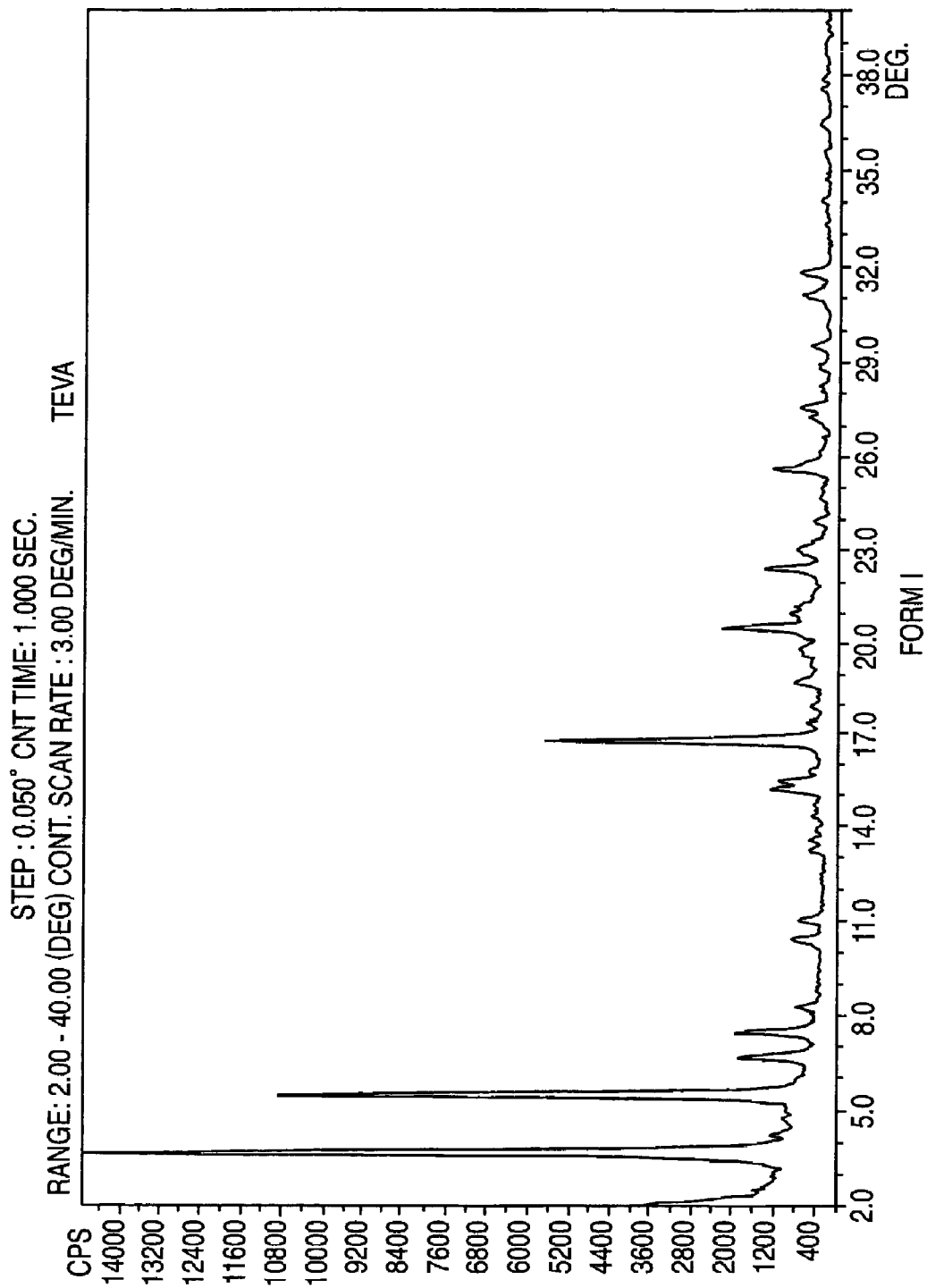
FIG. 7 is an XRPD pattern for nateglinide Form I.
Figure 8:
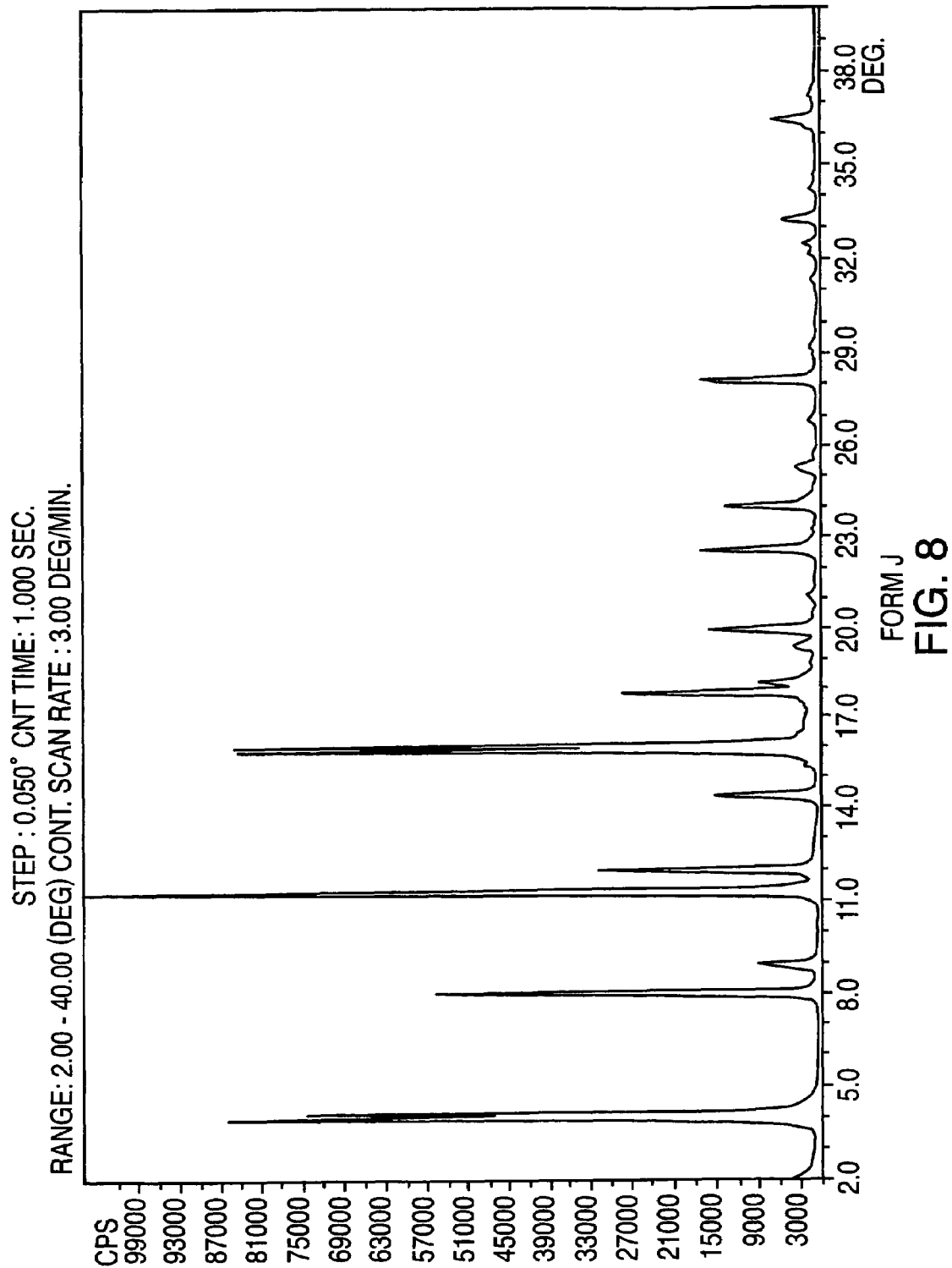
FIG. 8 is an XRPD pattern for nateglinide Form J.
Figure 9:
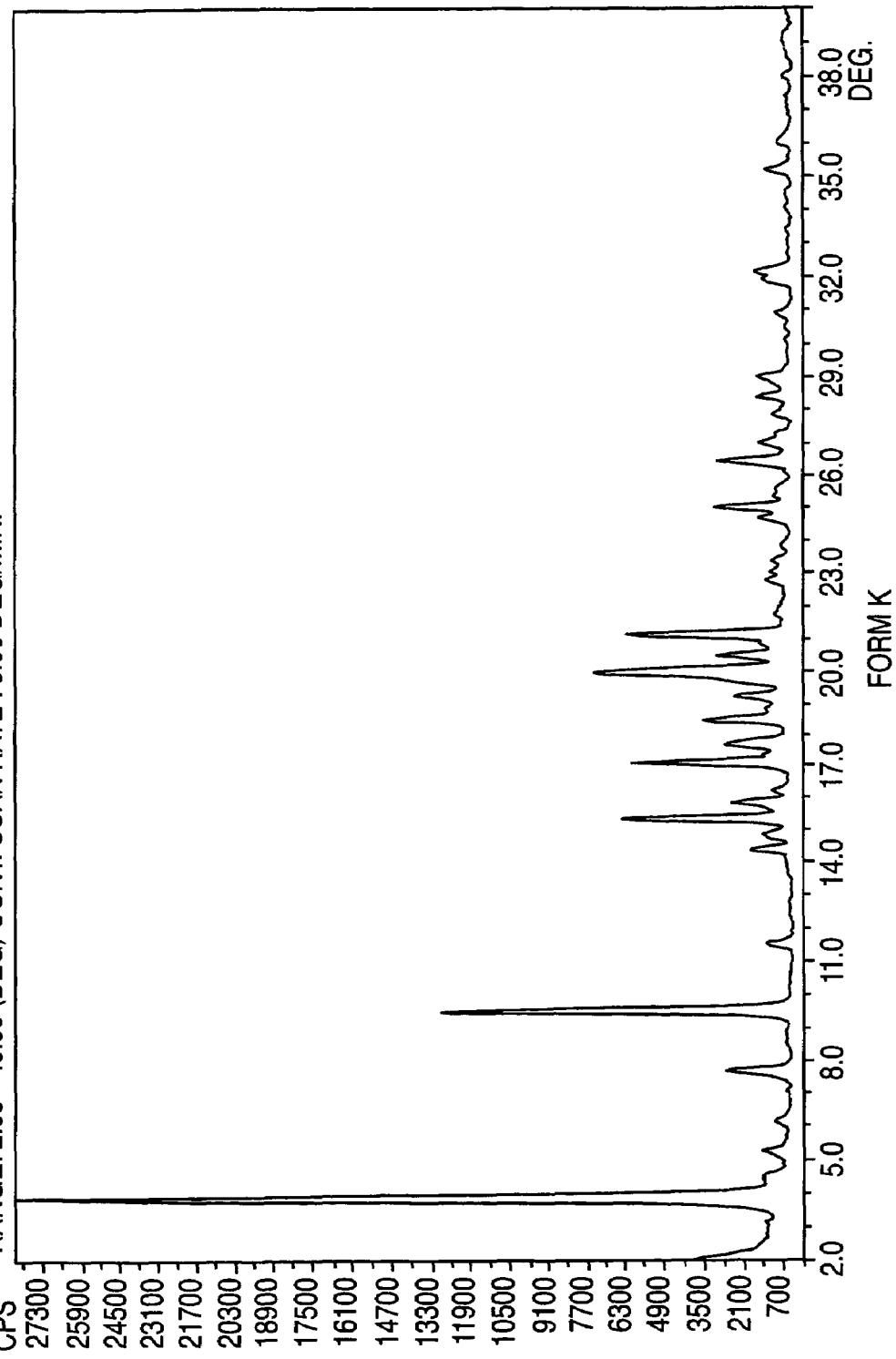
FIG. 9 is an XRPD pattern for nateglinide Form K.
Figure 10:
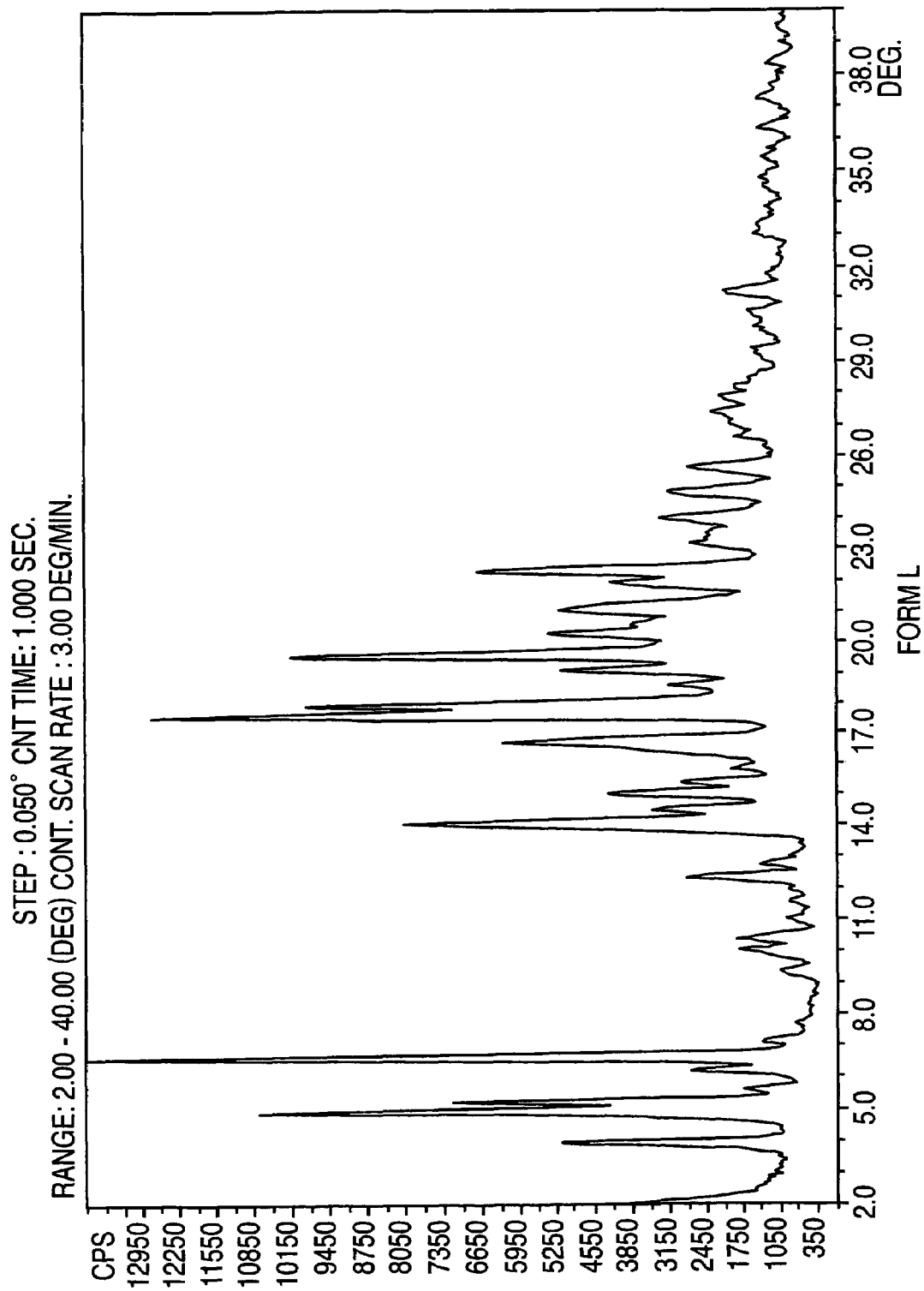
FIG. 10 is an XRPD pattern for nateglinide Form L.
Figure 11:
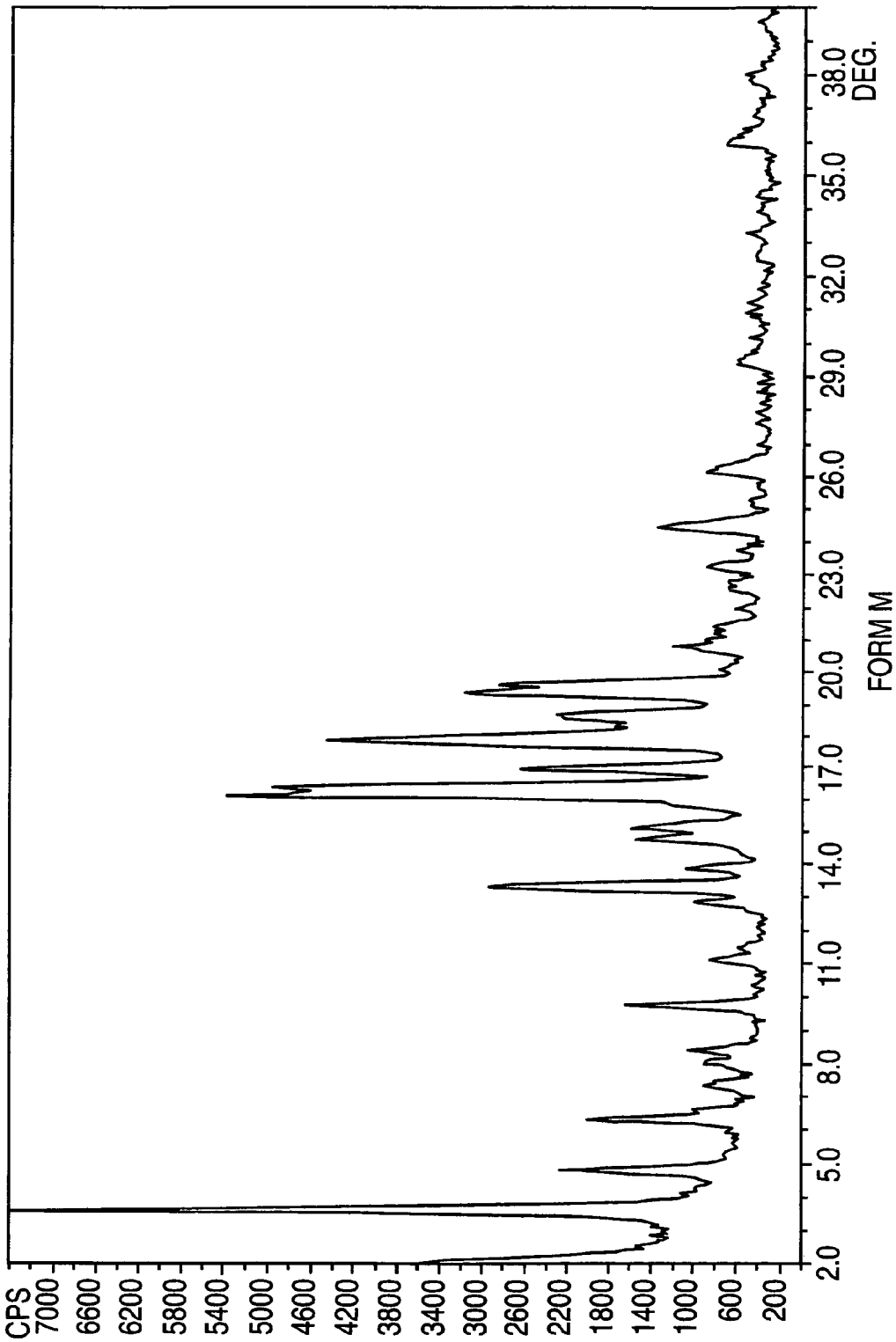
FIG. 11 is an XRPD pattern for nateglinide Form M.
Figure 12:
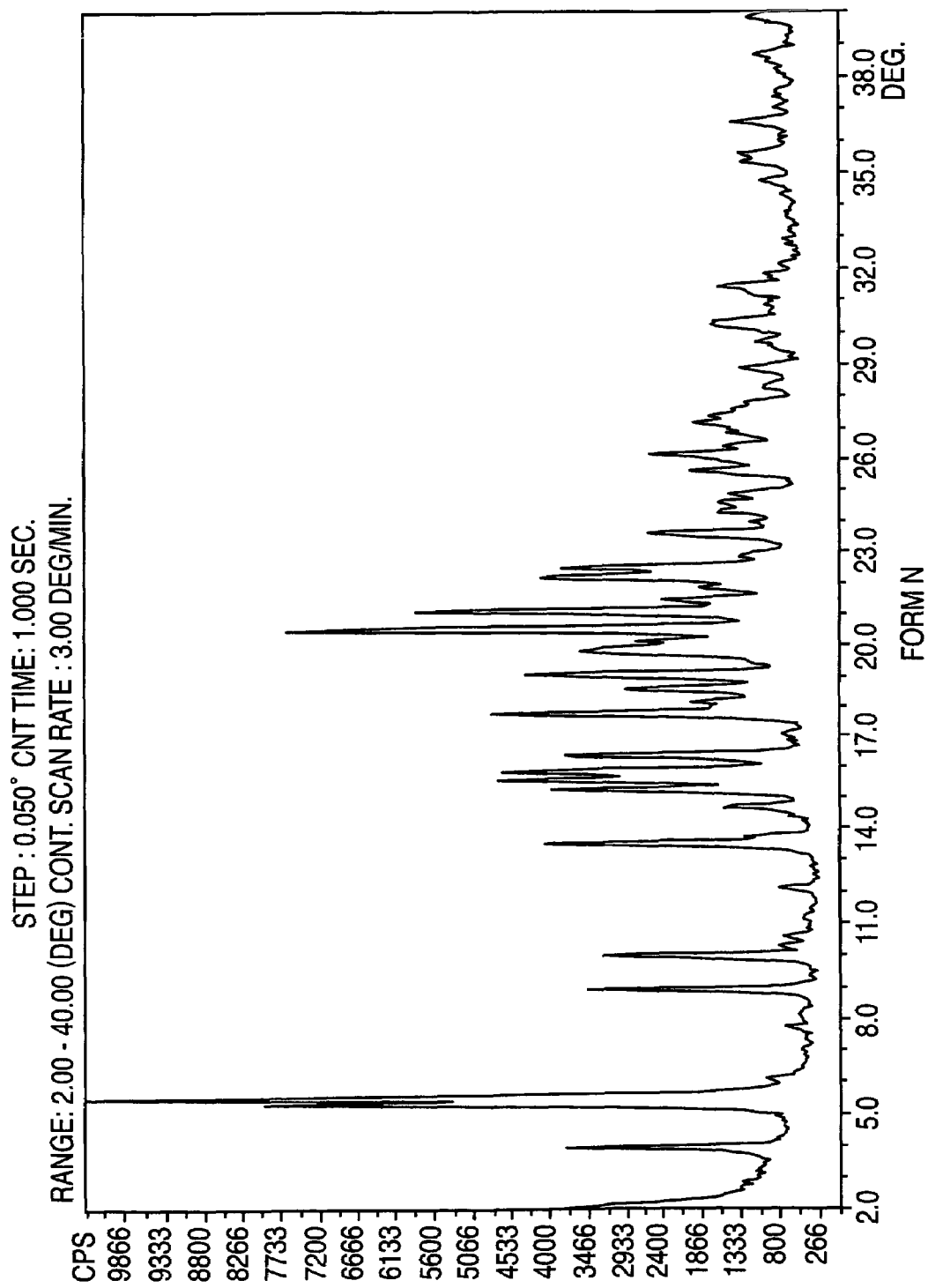
FIG. 12 is an XRPD pattern for nateglinide Form N.
Figure 13:
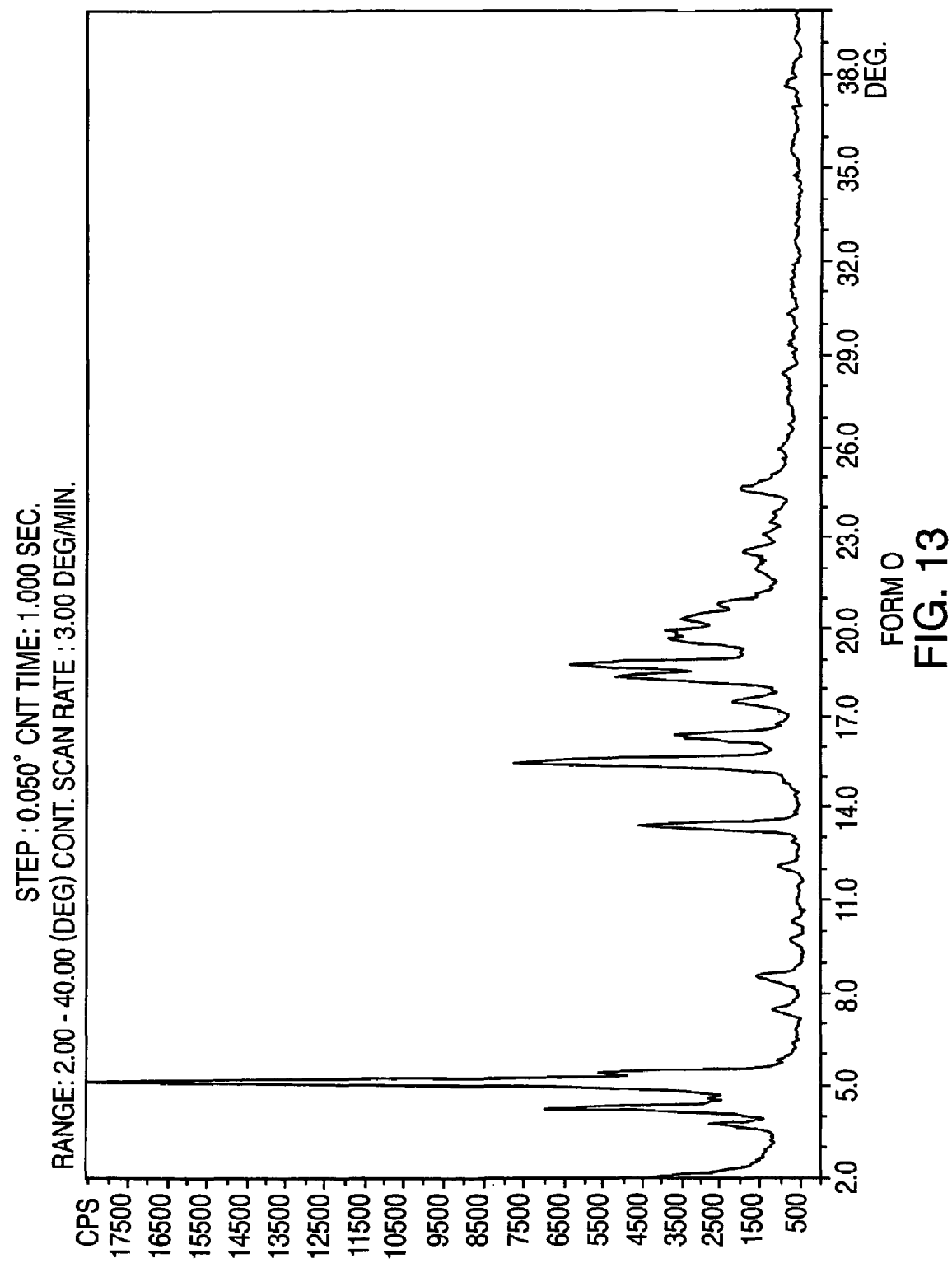
FIG. 13 is an XRPD pattern for nateglinide Form O.
Figure 14:
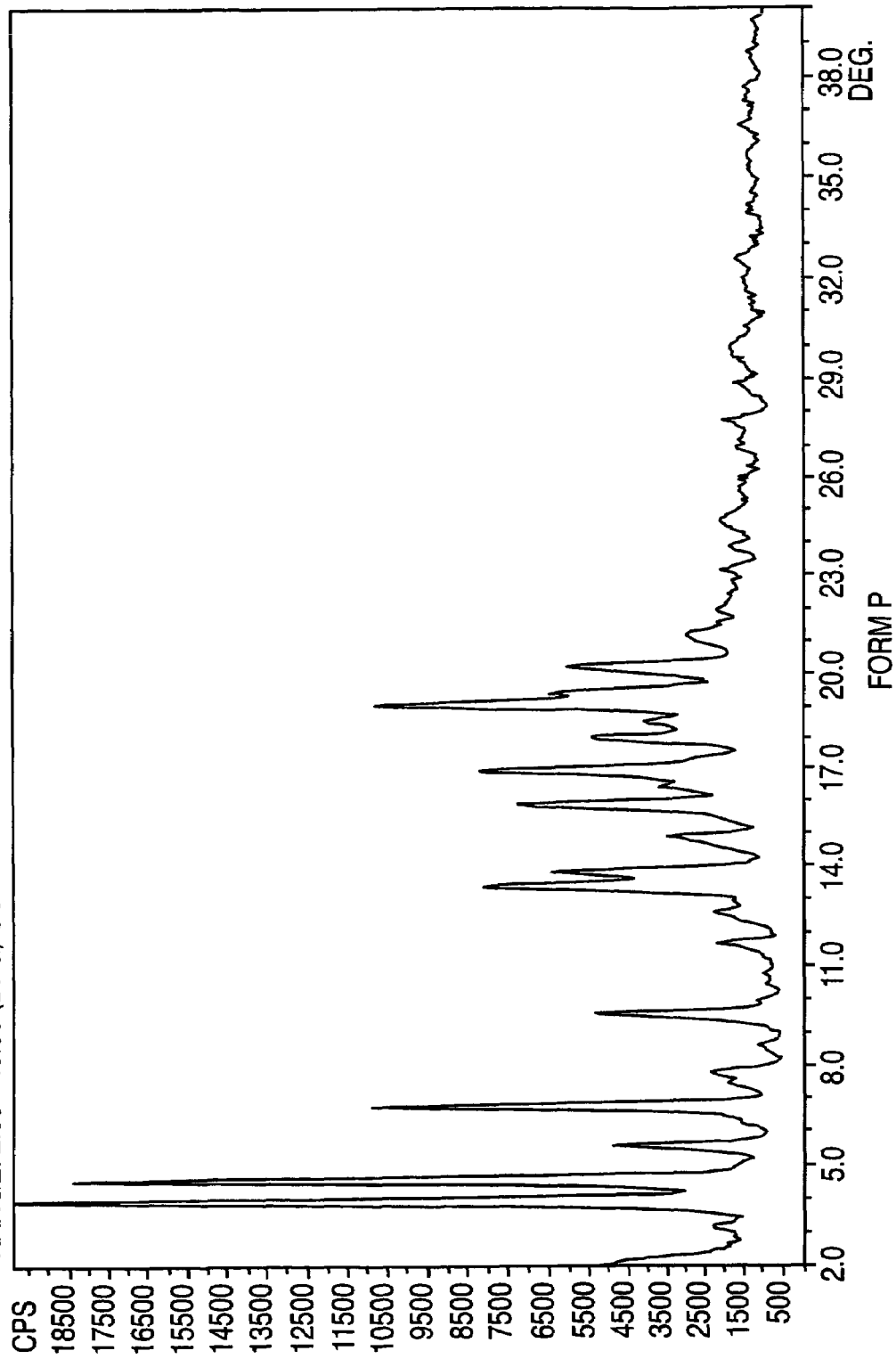
FIG. 14 is an XRPD pattern for nateglinide Form P.
Figure 15:
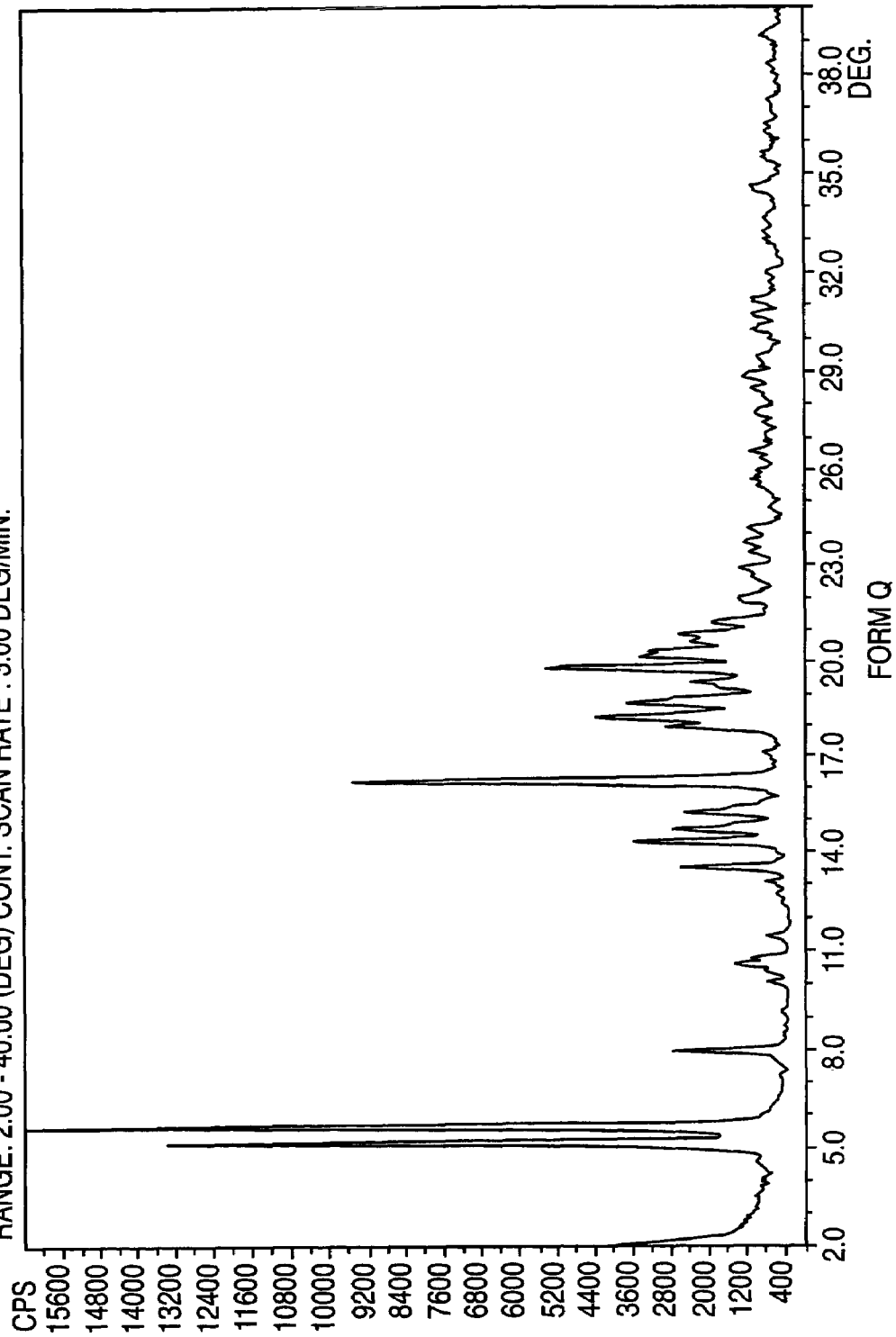
FIG. 15 is an XRPD pattern for nateglinide Form Q.
Figure 16:
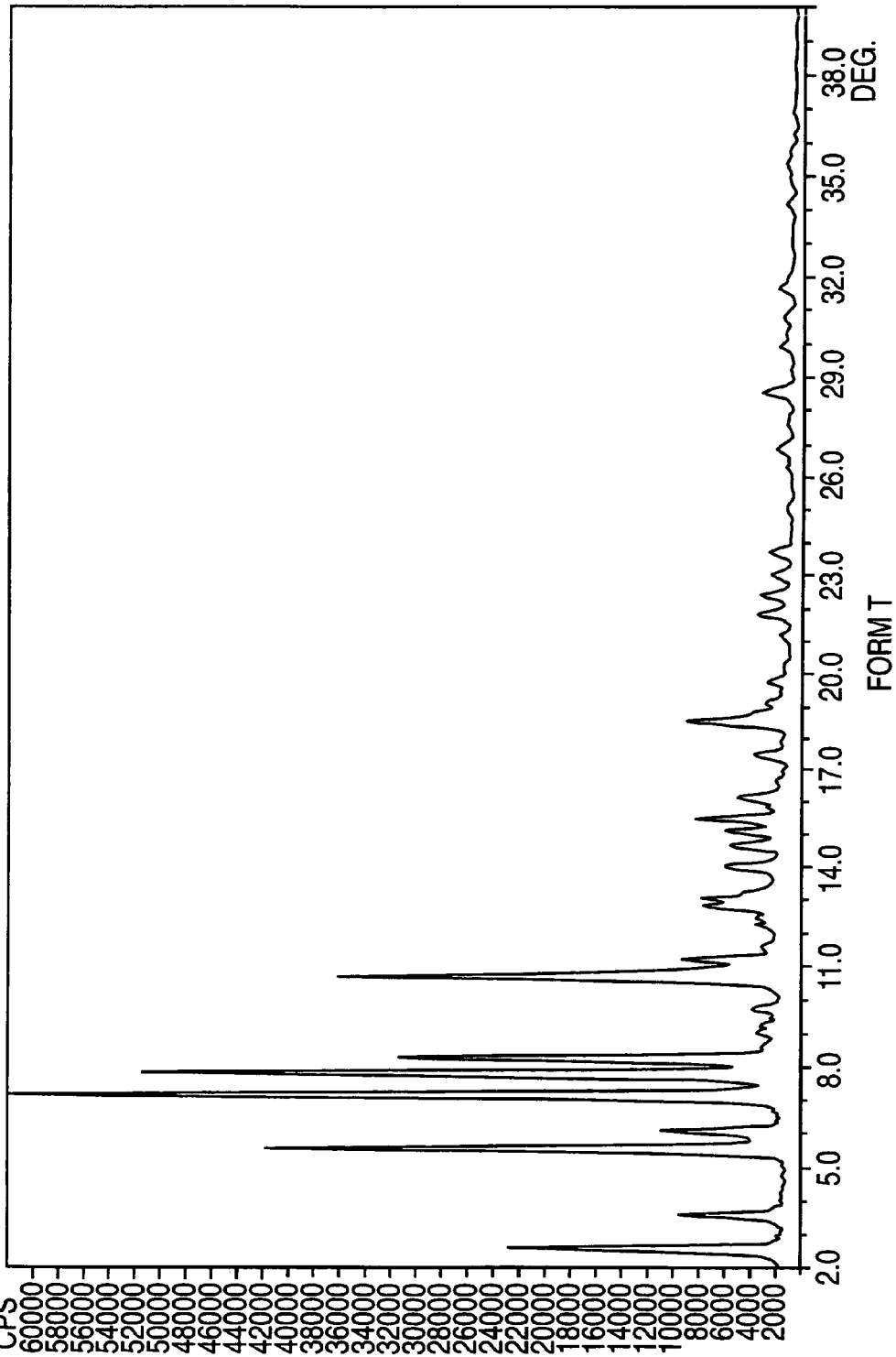
FIG. 16 is an XRPD pattern for nateglinide Form T.
Figure 17:
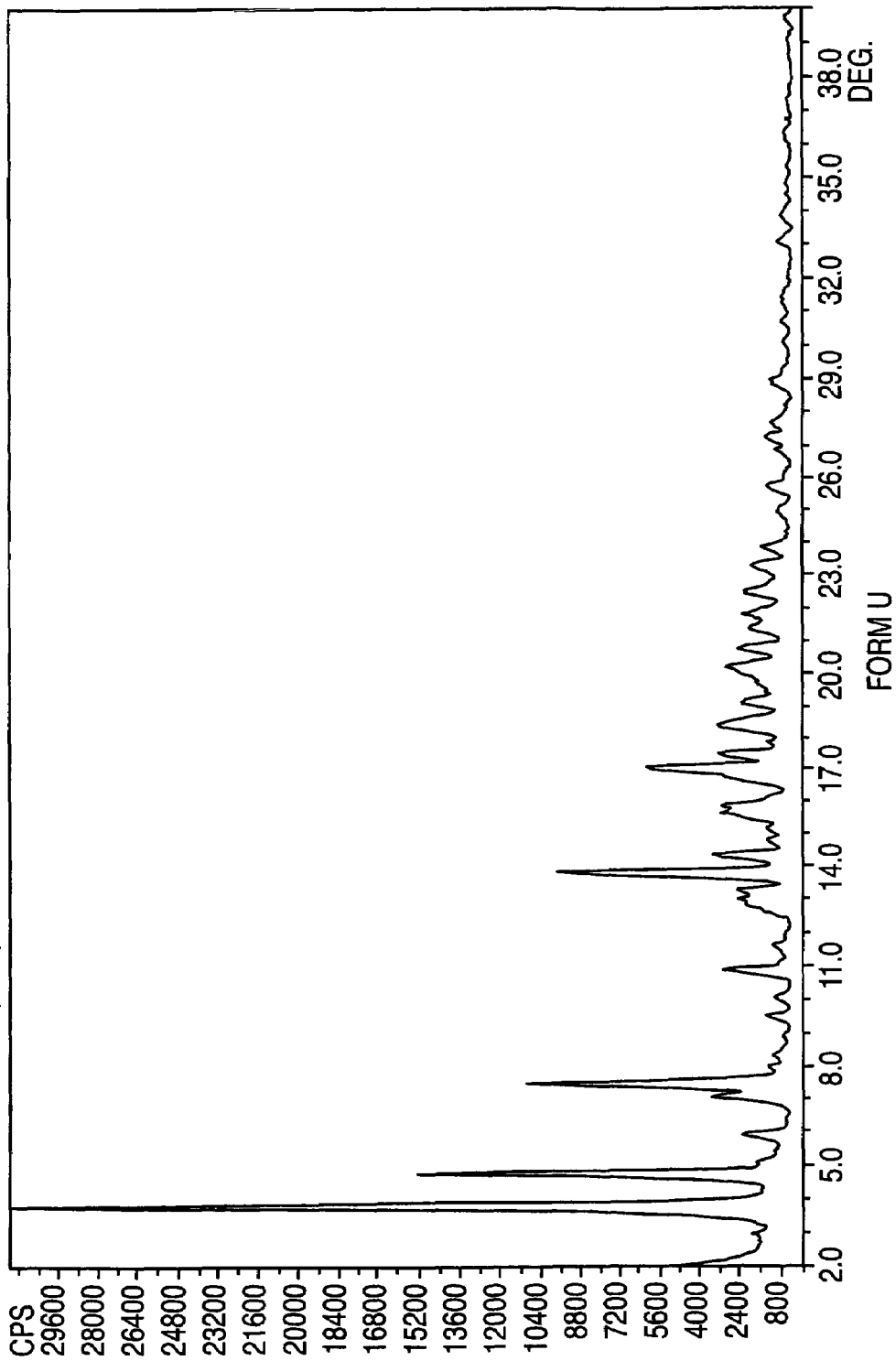
FIG. 17 is an XRPD pattern for nateglinide Form U in impure form.
Figure 18:
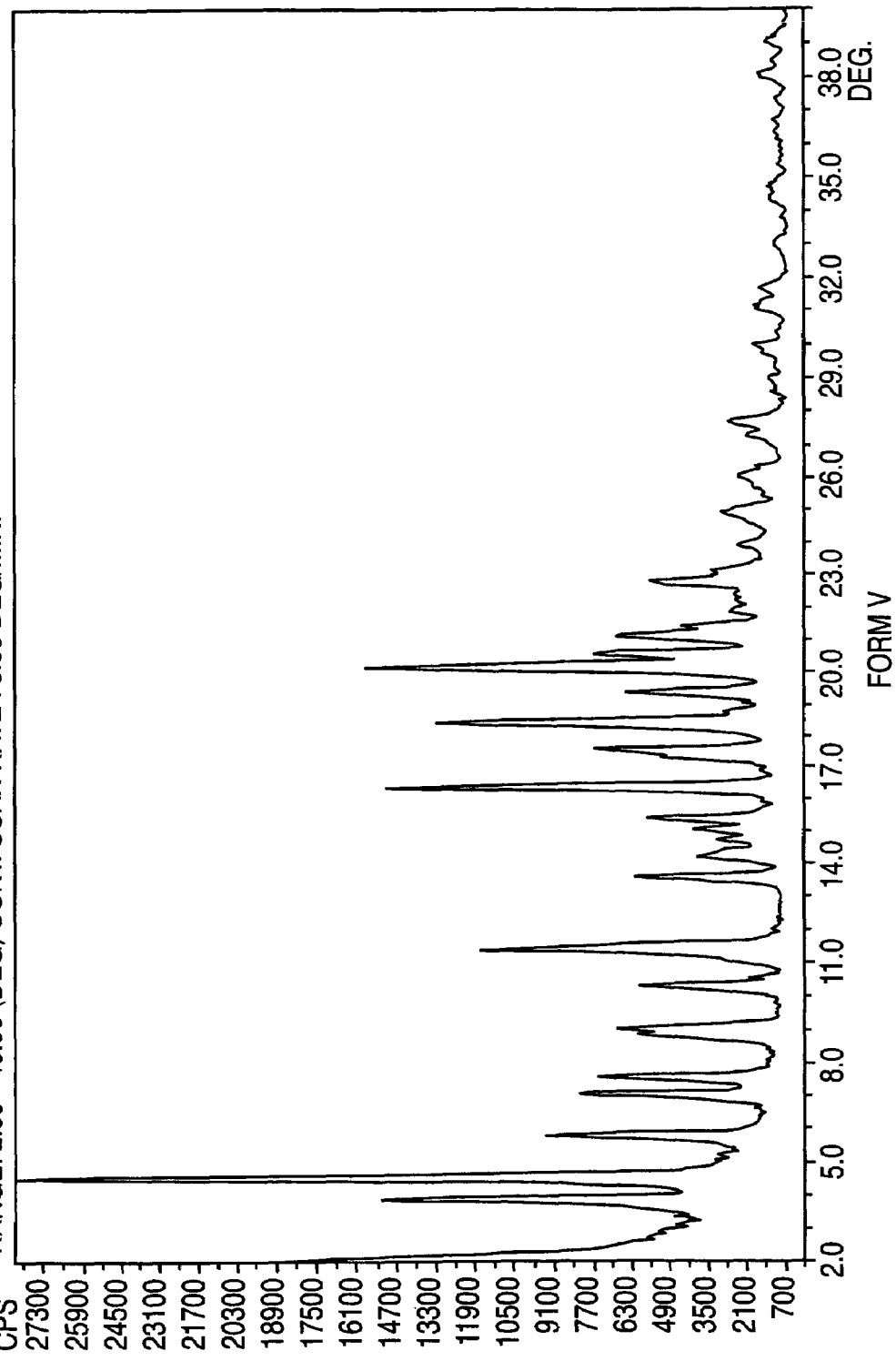
FIG. 18 is an XRPD pattern for nateglinide Form V.
Figure 19:
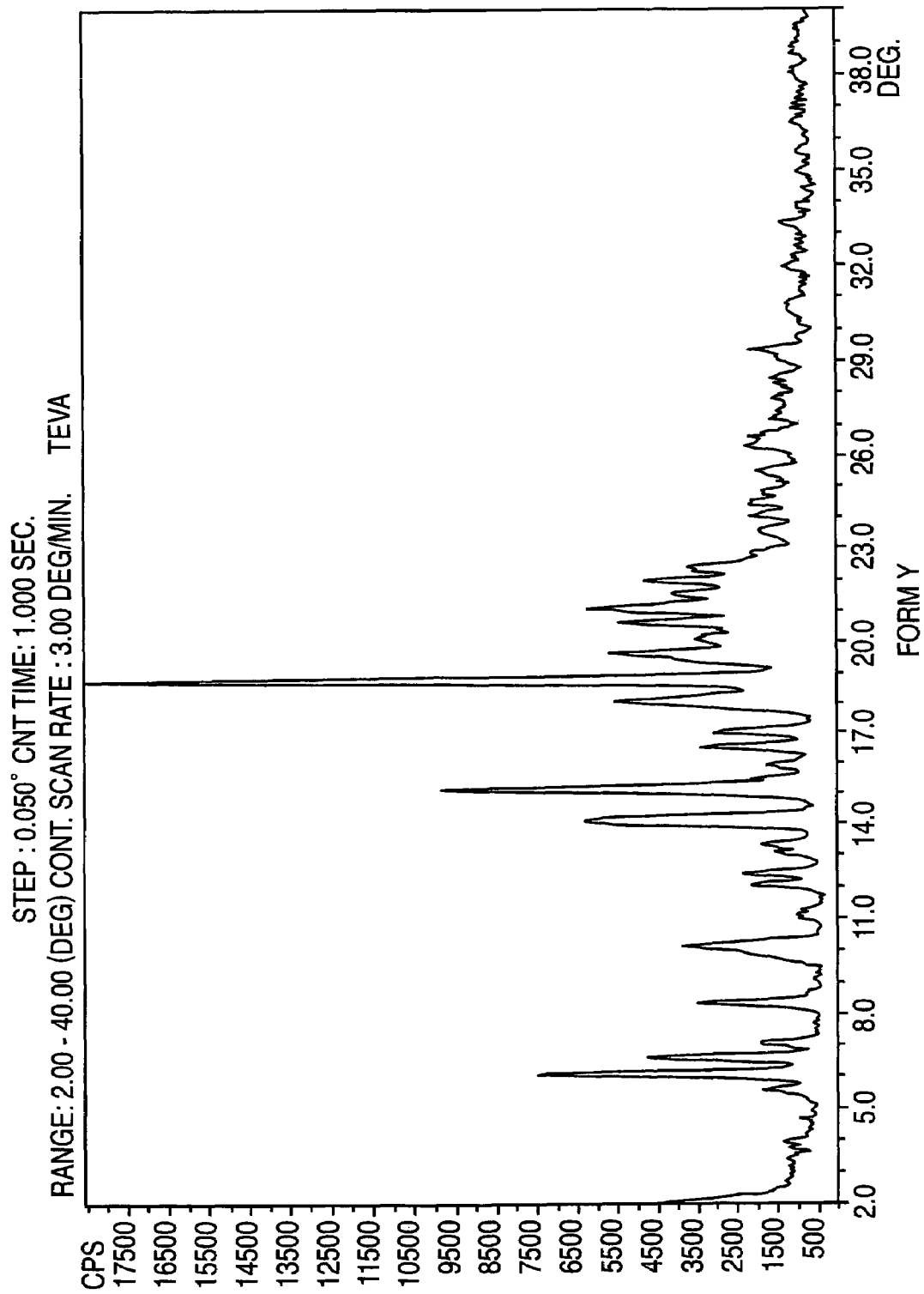
FIG. 19 is an XRPD pattern for nateglinide Form Y.
Figure 20:
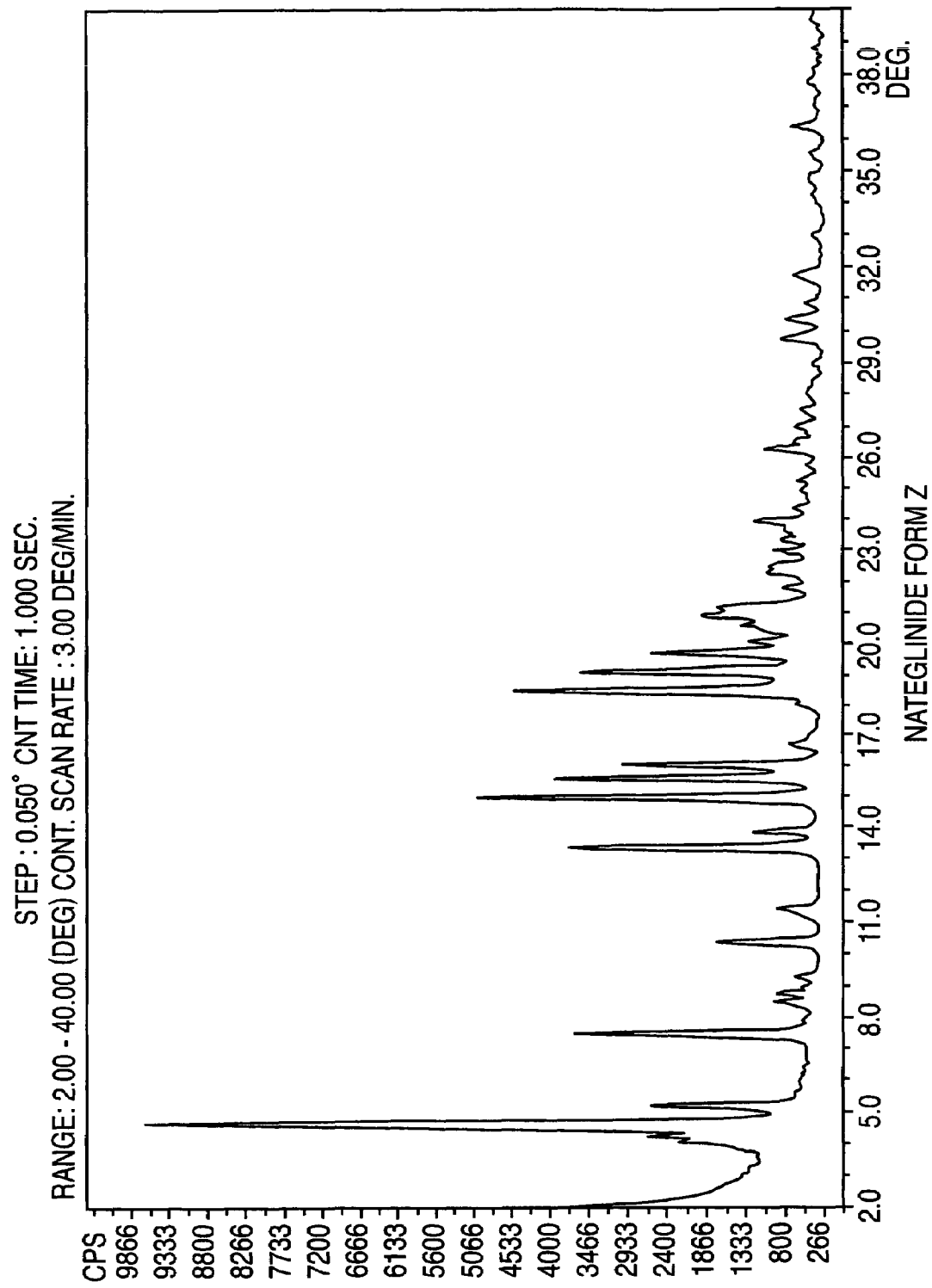
FIG. 20 is an XRPD pattern for nateglinide Form Z.
Figure 21:
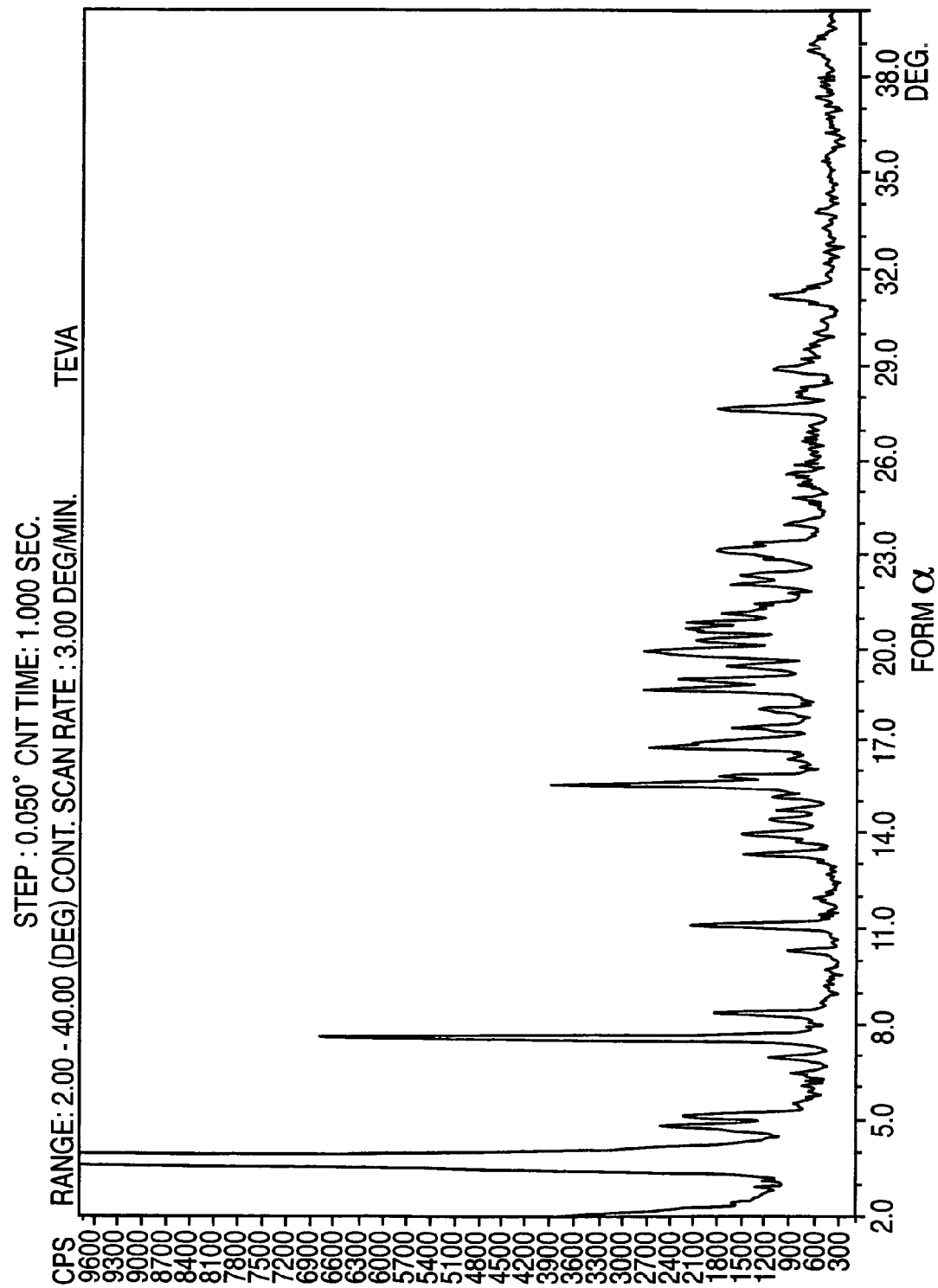
FIG. 21 is an XRPD pattern for nateglinide Form α.
Figure 22:
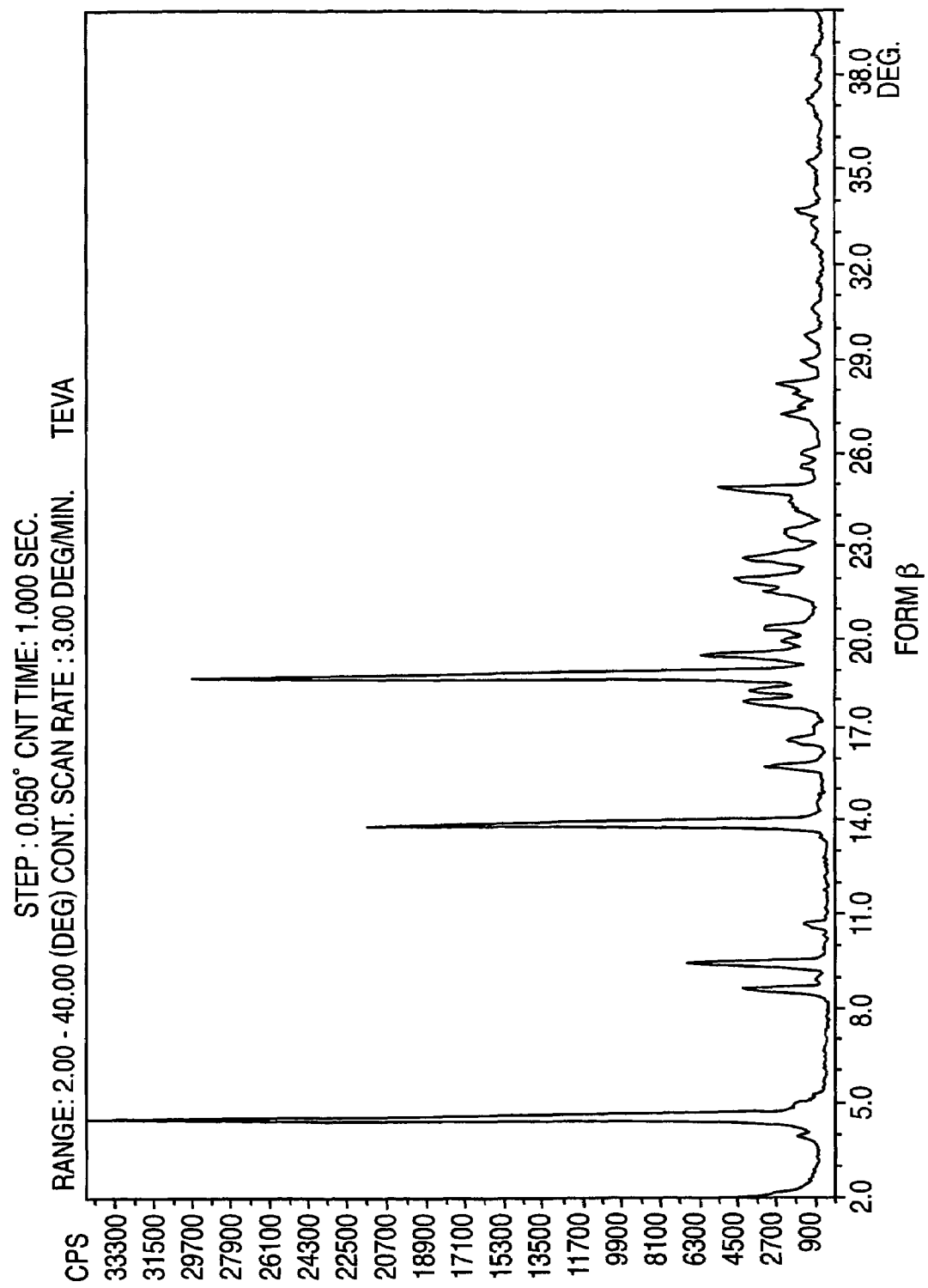
FIG. 22 is an XRPD pattern for nateglinide Form β.
Figure 23:
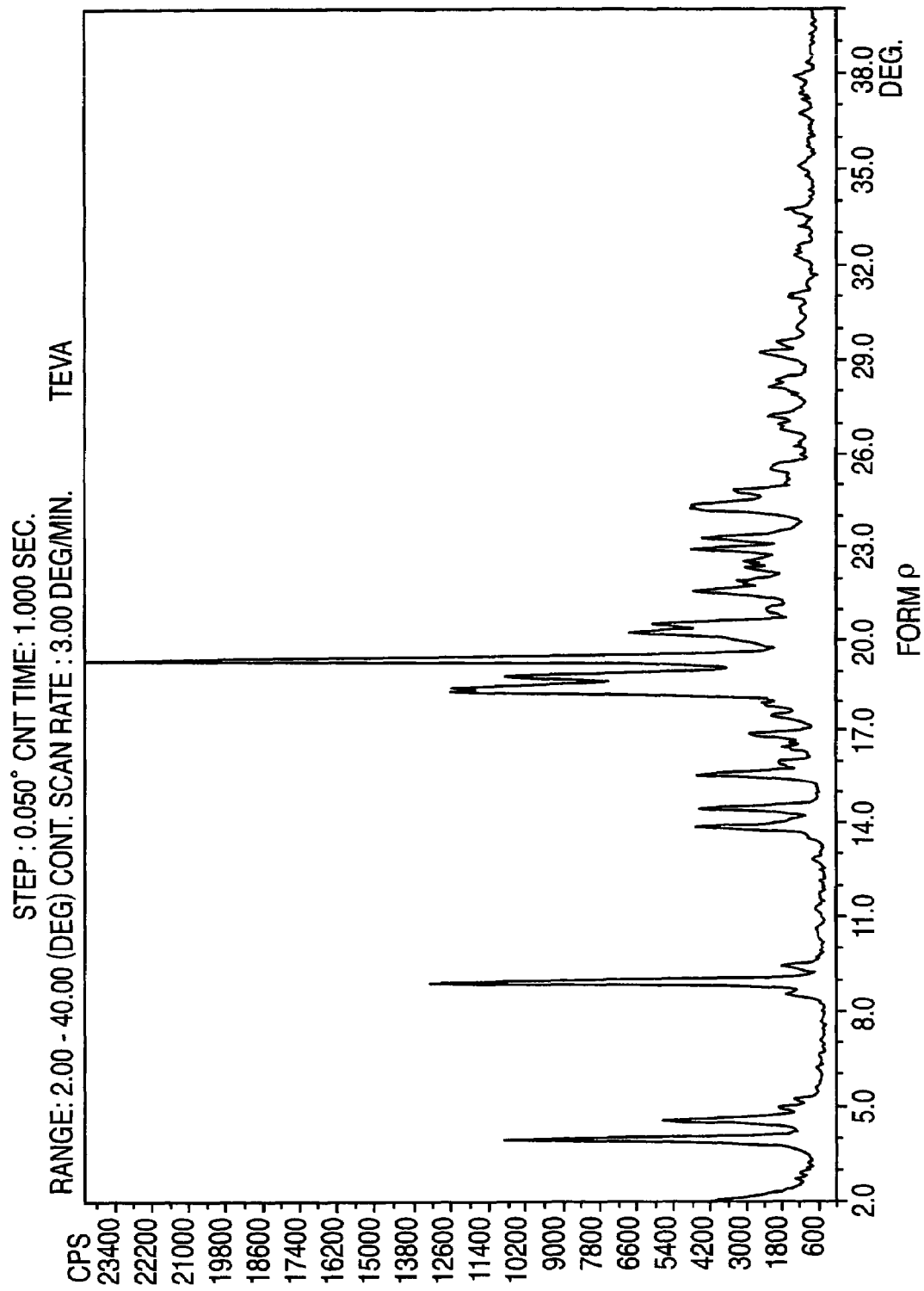
FIG. 23 is an XRPD pattern for nateglinide Form γ.
Figure 24:
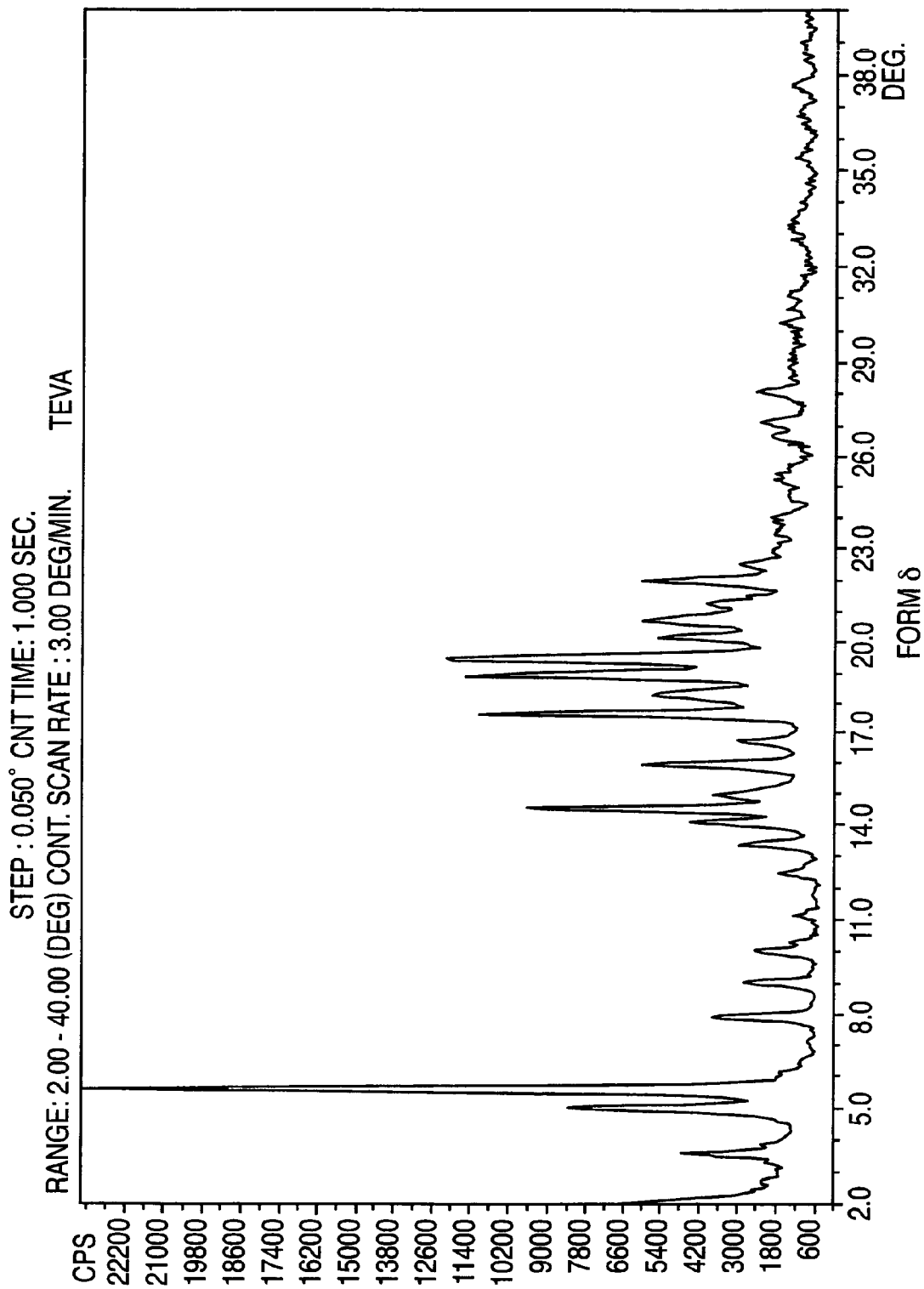
FIG. 24 is an XRPD pattern for nateglinide Form δ.
Figure 25:
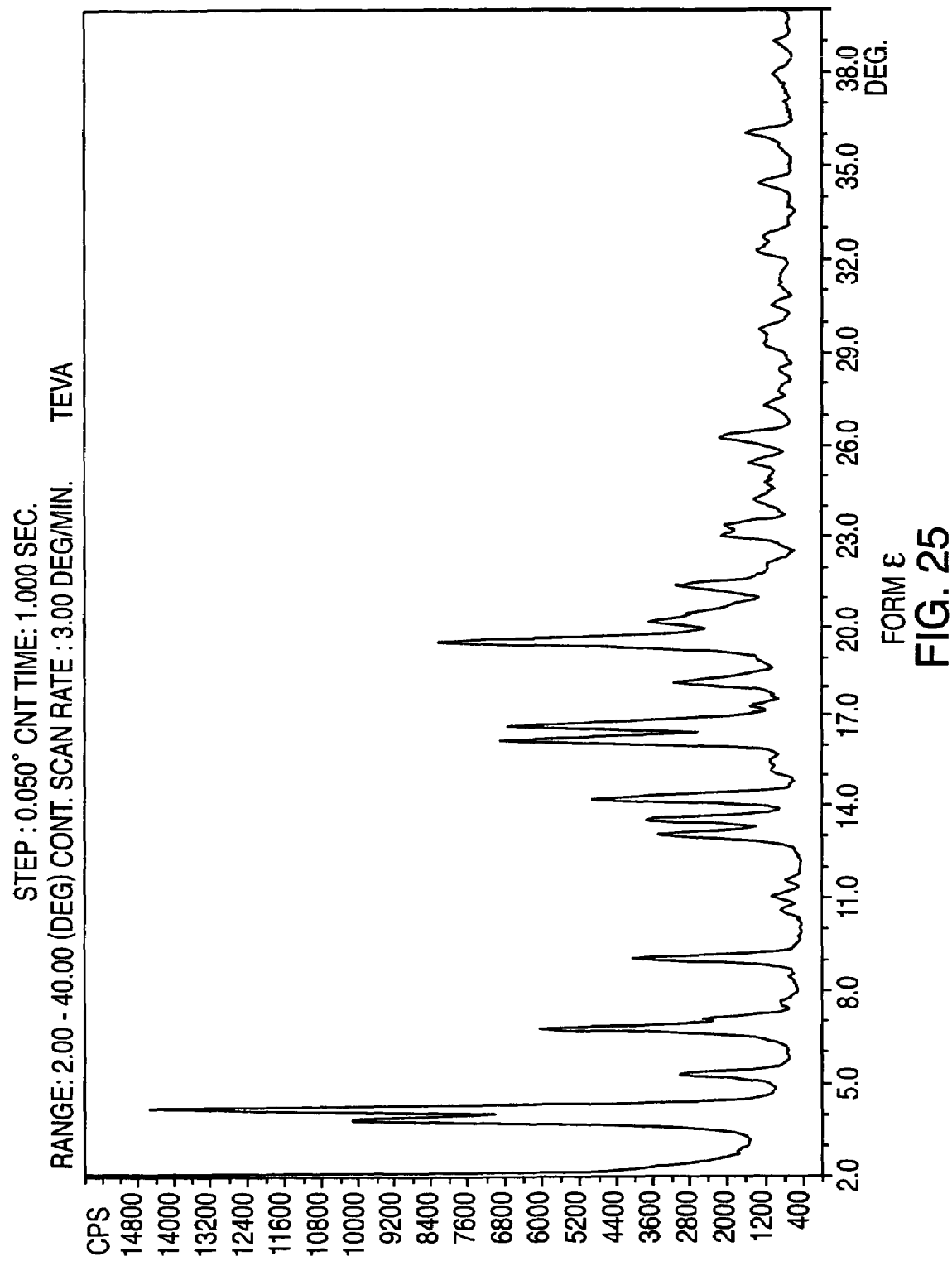
FIG. 25 is an XRPD pattern for nateglinide Form ε.
Figure 26:
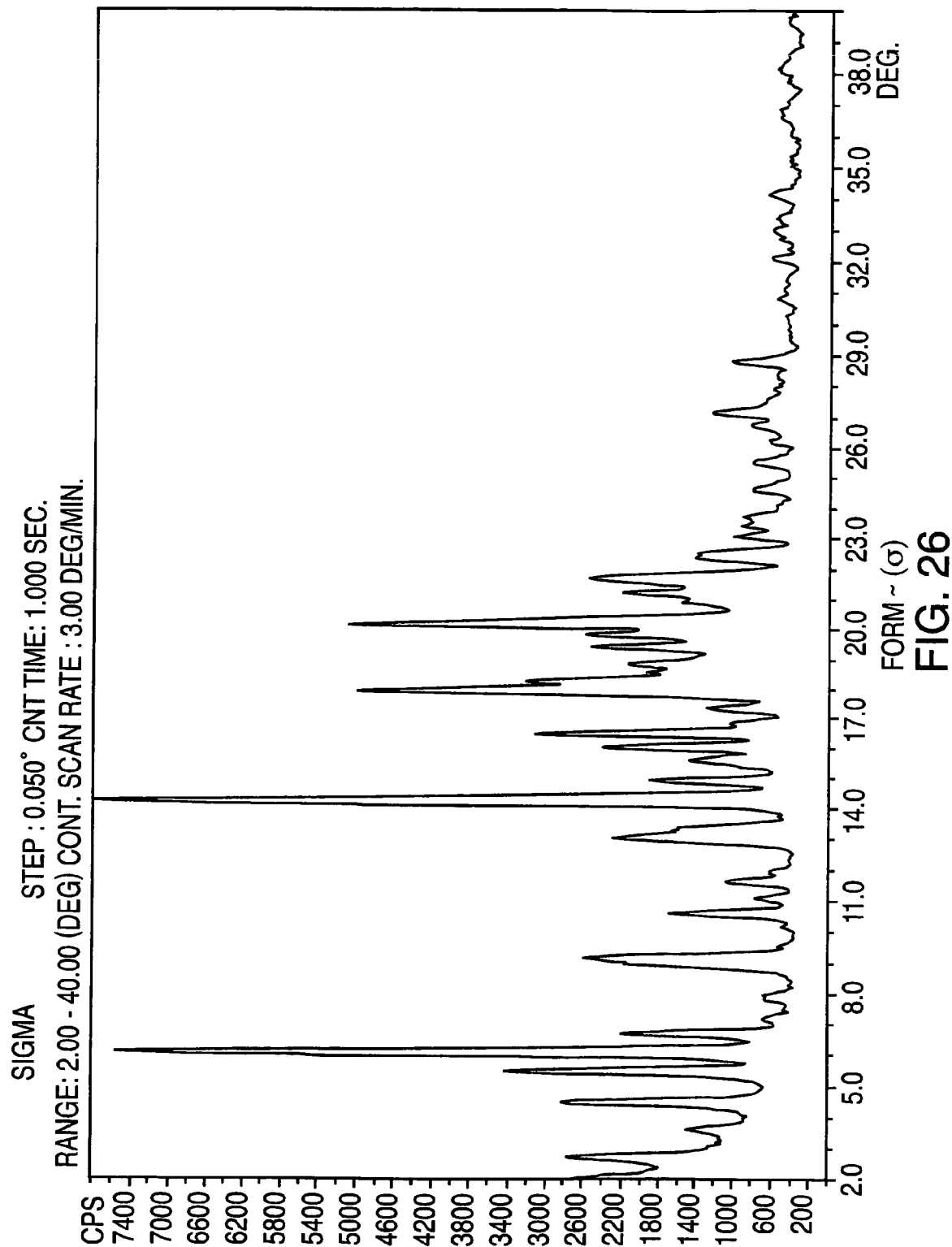
FIG. 26 is an XRPD pattern of nateglinide Form σ.
Figure 27:
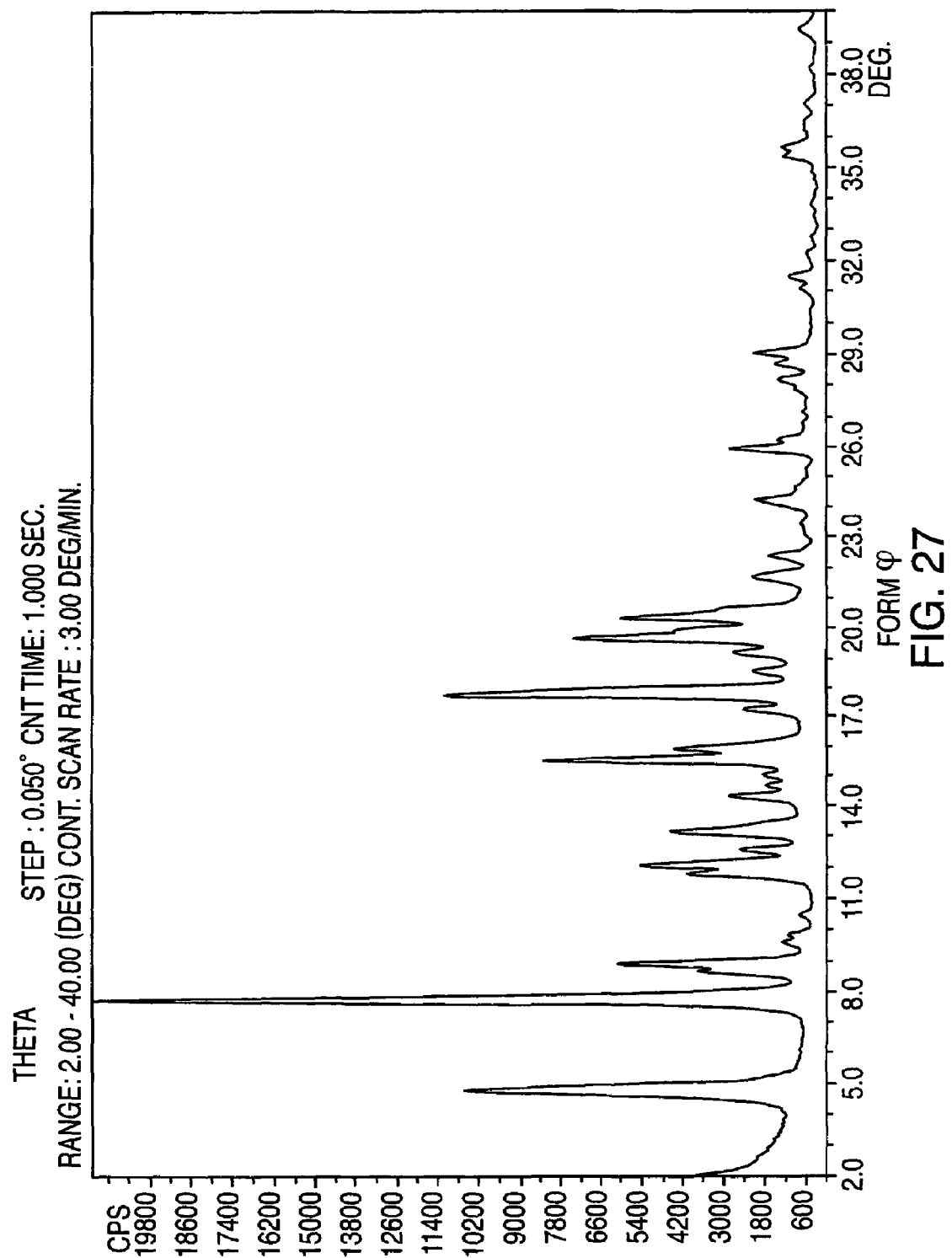
FIG. 27 is an XRPD pattern of nateglinide Form θ.

Nateglinide Form U is characterized by peaks at 4.7, 7.4, 13.8 and 17.0+/−0.2 theta are disclosed in Table 1. The additional peak at 3.8+/−0.2 disclosed in FIG. 17 in an impurity, and thus FIG. 17 is a mixture of Form U with another crystalline Form. Example 17 and refined processes for preparation of Form U do not produce the impurity at 3.8+/−0.2. Form U without such impurity is shown in FIGS. 65 through 69 and FIG. 31. It should be noted that non-crystallization methods produce the impurity at 3.8+/−0.2 for Form U.

Depending on the preparation procedure, nateglinide Form δ may contain from about 0.5% to about 3% of residual heptane by weight. The removal of heptane without changing the crystal form may be carried out in a fluidized bed drier, preferably at a temperature of from about 60 to about 70° C., more preferably for at least about 3 hours. The residual Heptane may be also removed under stirring, preferably at a temperature of at least about 40° C. under vacuum. The δ Form is preferably polymorphically pure and contains less than about 5% Form H (wt/wt), more preferably less than about 2% (wt/wt), and most preferably less than about 0.5% (wt/wt).

Crystalline Form δ is stable at a temperature of about 40° C and a relative humidity of about 75% for at least about 3 months.

Trituration of Form δ in ethyl acetate may result in other polymorphic forms of nateglinide. Triturating nateglinide Form δ at a temperature of from about 20 to about 30° C. in ethyl acetate results in Form U, while triturating at higher temperatures (above 40° C.), such as at about 50° C., results in Form B.

The processes of the present invention allow for obtaining Forms δ and B with a purity of at least about 95%, more preferably at least about 98% wt/wt compared to other polymorphic forms. These forms may be produced particularly free of the H Form.

The starting material used for the processes of the present invention may be any crystalline or amorphous form of nateglinide, including various solvates and hydrates. With crystallization processes, the crystalline form of the starting material does not usually affect the final result. With trituration, the final product may very depending on the starting material. One of skill in the art would appreciate the manipulation of the starting material within skill in the art to obtain a desirable form with trituration.

The processes of the present invention may also be practiced as the last step of prior art processes that synthesize nateglinide.

Many processes of the present invention involve crystallization out of a particular solvent, i.e., obtaining a solid material from a solution. One skilled in the art would appreciate that the conditions concerning crystallization may be modified without affecting the form of the polymorph obtained. For example, when mixing nateglinide in a solvent to form a solution, warming of the mixture may be necessary to completely dissolve the starting material. If warming does not clarify the mixture, the mixture may be diluted or filtered. To filter, the hot mixture may be passed through paper, glass fiber or other membrane material, or a clarifying agent such as celite. Depending upon the equipment used and the concentration and temperature of the solution, the filtration apparatus may need to be preheated to avoid premature crystallization.

The conditions may also be changed to induce precipitation. A preferred way of inducing precipitation is to reduce the solubility of the solvent. The solubility of the solvent may be reduced, for example, by cooling the solvent.

In one embodiment, an anti-solvent is added to a solution to decrease its solubility for a particular compound, thus resulting in precipitation. Another way of accelerating crystallization is by seeding with a crystal of the product or scratching the inner surface of the crystallization vessel with a glass rod. Other times, crystallization may occur spontaneously without any inducement. The present invention encompasses both embodiments where crystallization of a particular form of nateglinide occurs spontaneously or is induced/accelerated, unless if such inducement is critical for obtaining a particular form.

Nateglinide of defined particle size may be produced by known methods of particle size reduction starting with crystals, powder aggregates and course powder of the new crystalline forms of nateglinide. The principal operations of conventional size reduction are milling of a feedstock material and sorting of the milled material by size.

A fluid energy mill, or micronizer, is an especially preferred type of mill for its ability to produce particles of small size in a narrow size distribution. As those skilled in the art are aware, micronizers use the kinetic energy of collision between particles suspended in a rapidly moving fluid stream to cleave the particles. An air jet mill is a preferred fluid energy mill. The suspended particles are injected under pressure into a recirculating particle stream. Smaller particles are carried aloft inside the mill and swept into a vent connected to a particle size classifier such as a cyclone. The feedstock should first be milled to about 150 to 850 µm which may be done using a conventional ball, roller, or hammer mill. One of skill in the art would appreciate that some crystalline forms may undergo a transition to another form during particle size reduction.

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Pharmaceutical formulationss of the present invention contain a nateglinide Form selected from A, C, D, F, G, I, J, K, L, M, N, O, P, Q, T, U, V, Y, $\alpha$, $\beta$, $\gamma$, $\delta$, $\epsilon$, $\sigma$, $\theta$ and $\Omega$. The pharmaceutical composition may contain only a single form of nateglinide, or a mixture of various forms of nateglinide, with or without amorphous form. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidone®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, nateglinide and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The dosage and formulation of STARLIX may be used as a guidance. The dosage used is preferably from about 30 to about 240 mg of nateglinide, more preferably from about 60 to about 120 mg of nateglinide. The pharmaceutical compositions of the present invention, preferably in the form of a coated tablet, are administered from about 10 minutes to about 1 hours prior to a meal, more preferably about 15 minutes before each meal. The dose is not taken if the meal is skipped. The pharmaceutical compositions may also be used in combination with metaformin.

Instruments

X-Ray Powder Diffraction:

X-Ray diffraction was performed on X-Ray powder diffractometer, Scintag®, variable goniometer, Cu-tube, solid state detector. Sample holder: A round standard aluminum sample holder with round zero background quartz plate.

The sample was put on the sample holder and immediately analyzed as is. Scanning parameters: Range: 2-40 deg 2θ, Continuos Scan, Rate: 3 deg./min.

DSC:

DSC821$^e$ Mettler Toledo®, Sample weight: 3-5 mg, Heating rate: 10° C./min, Number of holes in the crucible: 3

TGA:

Mettler TG50®, Sample weight: 7-15 mg, Heating rate: 10° C./min

FTIR:

Perkin-Elmer®, Spectrum One FTIR spectrometer, Range: 4000-400 cm-1, no. of scans: 16, resolution: 4.0 cm-1, DRIFT technique.

EXAMPLES

Example 1

This Example Illustrates Preparation of Various Forms of Nateglinide from a Solution Nateglinide (5 g) was placed into an erlenmeyer flask and heated to the specified temperature. The solvent was added in 1-ml portions (in some cases, the solvent was added in 5-ml portions) until a clear solution was obtained. If a clear solution was not obtained after addition of 150 ml of the solvent, the hot mixture was filtered.

The clear solution was left to crystallize at room temperature. If crystallization did not happen or was poor, the solution was refrigerated at 3° C. The precipitate was filtered off (at RT or at 5° C. depending on the temperature of the crystallization), weighed and divided into 2 equal parts. One part was dried at 50° C. under reduced pressure (20-30 mmHg) to constant weight (±0.01 g) for about 3-10 hours. Details are presented in Table

TABLE IV

Data on crystallization of NTG from a single solvent

| Solvent | L/S, ml/g | T, ° C. | Time RT, h | Time 3° C., h | Form Wet | Form Dry |
|---|---|---|---|---|---|---|
| Xylene | 30 | 70 | 25 | — | A | A >> B |
| DMA | 1 | 55 | 25 | — | C | α |
| EtOH | 1 | 55 | 25 | — | D | L |
| EtOH | 2* | 54 | 6 | 42 | D | B |
| MeOH | 1 | 55 | 24 | — | E | B |
| EtOH | 3 | 55 | 1 m | 18 d | E | B |
| n-PrOH | 1 | 57 | 25 | 144 | F | G + B |
| n-PrOH | 2 | 55 | 10 d | — | α | α |
| n-PrOH | 2 | 55 | 3 | 5 d | α | α |
| IPA | 1.2 | 57 | 25 | 48 | G | B |
| IPA | 3 | 55 | 1 m | 20 | α | α |
| NMP | 1.4 | 57 | 73 | — | J | B + β |
| DMF | 1.6 | 56 | 24 | 52 | K | S |
| CTC | 30 | 65 | 25 | — | M | L |
| DCE | 2.2 | 55 | 23 | 47 | N | L |
| CHCl$_3$ | 1 | 54 | 73 | 193 | Q | Q |
| DME | 1.4 | 56 | 96 | — | V | H |
| n-BuOH | 4 | 55 | 1 m | 20 | α | S |
| n-BuOH | 1.4 | 57 | 25 | 144 | I | S |
| Acetone | 2 | 20 | 144 | 20 | ε | H |
| NM | 30 | 70 | 24 | — | ε | P |
| MeCN | 8 | 55 | 3 | 20 | ε | ε + B |
| MeCN | 19 | 55 | 8 d | — | α | α |
| MeCN | 19 | 55 | 7 d | 5 | α | α |
| DCM | 2* | 54 | 47 | — | Y | Y |
| EA | 9 | 55 | 22 | — | α | α |
| EA | 9 | 55 | 10 d | 5 d | α | α |
| EA | 15 | 55 | 9 d | — | α | α |
| EA | 15 | 55 | 8 d | 5 d | α | α |

Legend.
L/S—liquid/solid ratio:
*the solvent was added in 5-ml portions;
T—starting temperature;
Ww—weight of wet sample after filtration,
Wd—weight of the sample after drying at 80-90° C./20 mbar.
Solvent abbreviations:
MeOH—methanol,
EtOH—ethanol,
n-PrOH—n-propanol,
IPA—2-propanol,
n-BuOH—n-butanol,
EA—ethyl acetate,
NM—nitromethane,
DMF—N,N-dimethylformamide,
DMA—N,N-dimethylacetamide,
NMP—N-methylpyrrolidone,
MeCN—acetonitrile,
Ether—diethyl ether,
DME—dimethoxyethane,
DCM—dichloromethane,
DCE—1,2-dichloroethane and
CTC—carbon tetrachloride

Example 2

This Example Illustrates Trituration of Nateglinide Form H and U in Various Solvents Nateglinide (5 g) was placed into an Erlenmeyer flask. Solvent was added in 1-ml portions to prepare a stirrable mixture. The flask was stirred with a magnetic stirrer at room temperature. A solid was filtered off at room temperature, weighted, and divided into 2 equal parts. One part was dried at 55° C. under 20-30 mm/Hg pressure to constant weight (±0.01 g).

Details are presented in Tables V and VI.

TABLE V

Data on trituration of NTG with a single solvent

| Start Form | Solvent | L/S ml/g | Time, h | Form wet | Form dry |
|---|---|---|---|---|---|
| H | MeOH | 1.2 | 24 | T | G + B |
| H | EtOH | 1.2 | 24 | D | B |
| H | IPA | 1.2 | 24 | G | G + B |
| H | n-PrOH | 1.2 | 23 | F | B |
| H | n-BuOH | 1.4 | 24 | I | |
| H | MeCN | 4.8 | 25 | P | H + P |
| H | NM | 4 | 26 | ε | H + P |
| H | NMP | 0.8 | 24 | J | β |
| H | DMF | 1.2 | 25 | K | |
| H | DMA | 1.2 | 26 | C | B |
| H | DME | 1.4 | 24 | V | H |
| H | Dioxane | 2.2 | 24 | δ | δ |
| H | THF | 0.8 | 23 | δ | δ |
| H | DCM | 1.8 | 25 | Y | Y |
| H | CHCl$_3$ | 1 | 25 | Q | Q + B |
| H | DCE | 1.8 | 24 | Q + H | Q + H |

TABLE VI

Data on trituration of NTG with a single solvent

| Start Form | Solvent | L/S ml/g | Time, h | Form wet | Form dry |
|---|---|---|---|---|---|
| U | AcOH | 1.8 | 24 | H + S | H + S |
| U | MeOH | 1.2 | 24 | α | α |
| U | EtOH | 1.6 | 24 | B + α | B + α |
| U | IPA | 1.8 | 24 | G + S | G + S |
| U | n-PrOH | 1.4 | 25 | F | B |
| U | n-BuOH | 1.6 | 26 | α | α |
| U | NM | 5 | 24 | P | P |
| U | NMP | 1 | 25 | J + γ | γ |
| U | DMF | 1 | 23 | K | α |
| U | DMA | 1.2 | 24 | C | α |
| U | Acetone | 2 | 24 | P | P |
| U | MEK | 2.4 | 23 | H + α | H + S |
| U | MIPK | 3 | 24 | H + α | H |
| U | MIBK | 3.6 | 24 | H + α | H + S |
| U | DME | 1.8 | 24 | H + α | H + S |
| U | Dioxane | 2 | 23 | δ | B |
| U | THF | 0.8 | 23 | δ | δ + B |
| U | DCM | 1.6 | 24 | Y + S | Y + S |
| U | CHCl$_3$ | 1.2 | 25 | δ | δ |
| U | DCE | 3.8 | 26 | Q | Q |

Example 3

This Example Illustrates Absorption of Solvent Vapors by Nateglinide

Nateglinide (3.50 g) was added to a polypropylene can and weighed. The can was introduced into a bigger polypropylene container containing a solvent, and stored at room temperature. The can was removed from the container and weighed (W final). The can content was divided into 2 portions. One portion was dried at a temperature of 55° C. and a pressure of 20-30 mmHg to constant weight (±0.01 g). Details are presented in Table VII.

TABLE VII

Data on absorption of solvent vapors with NTG Form H

| NTG W, g | Brutto, g | Solvent | Time, d | Wfinal | Δ | Form wet | Form dry |
|---|---|---|---|---|---|---|---|
| 3.50 | 15.77 | EtOH | 4 | 16.29 | 0.52 | D | B |
| 3.50 | 15.94 | MeOH | 4 | 16.12 | 0.18 | O | O |
| 3.50 | 15.78 | Acetone | 4 | 15.86 | 0.08 | H | H |
| 3.49 | 51.86 | DCM | 4 | 51.90 | 0.04 | Y | — |
| 3.50 | 15.27 | Water | 4 | 15.29 | 0.02 | H | H |

Legend.
Brutto—starting weight of the can with NTG;
Wfinal—final weight of the can with NTG after the exposure;
Δ—overweight

Example 4

This Example Illustrates Preparation of Various Forms of Nateglinide by Solvent Removal Nateglinide (5 g) was dissolved in the following solvents at about 55 C in over about 15 minutes until a clear solution was obtained. The solvent was removed to dryness by evaporation at about 55 C/20-30 mmHg to give dry nateglinide.

TABLE VIII

Data on solvent removal

| Solvent | Form, dry |
|---|---|
| MeCN | B |
| Acetone | B |
| EA | B |

Example 5

This Example Illustrates Preparation of Form Z

D-Phenylalanine (PheOH, 7.73 g) was treated with 3.5% NaOH (185 ml, 3.5 equivalents), at room temperature to afford a clear solution of the corresponding Na-salt. A solution of neat trans-4-isopropylcyclohexanecarboxyl chloride (IPCHAC, 9.02 g, 1.01 equivalent) was added to the solution of Phe-OH obtained above, over 3 minutes, while stirring at room temperature. The rest of the IPCHAC in the funnel was washed with toluene (1 ml) and added. The resulting mixture was stirred for 1 hour, and was treated with 10% HCl (32 ml) to adjust the pH to 3, while stirring. The mixture was stirred for 1 hour, and filtered. The solid was washed with water (200 ml) and sucked well to afford 33.3 g of the moist product, which lost weight after drying at 78° C./2.2 mbar. Assay 98.4%, purity>99%, yield 86%.

Example 6

This Example Illustrates Preparation of Nateglinide by Cystallization from Binary Mixtures (Solvent/Anti-Solvent)

Nateglinide (5g) and an anti-solvent (20 ml) were placed into an Erlenmayer flask. The mixture was heated at about 55° C. over about 15 minutes, followed by addition of solvent in 0.25-1 ml portions until a clear solution was obtained. The clear solution was left to crystallize without stirring at room temperature.

If crystallization did not happen or was poor after 24 hours, the solution was refrigerated at 3-5° C. The precipitate was filtered off (at RT or at 5° C. depending on the temperature of crystallization) to give Form B. The wet material was dried at 50° C. under reduced pressure (20-30 mmHg) to give dry Form B.

TABLE IX

Data on crystallization of NTG from binary solvents

| Solvents | Ratio, v/v | L/S, ml/g | $T_{cryst}$, ° C.$^f$ | Time, h | Ww, g | Wd, g | Form wet | Form dry |
|---|---|---|---|---|---|---|---|---|
| Toluene-EtOH | 40:1 | 4.1 | RT→3 | 23/23 | 7.84 | 3.56 | B | B |
| Toluene-MeOH | 40:1 | 4.1 | 3 | 22/23 | 6.82 | 3.72 | E | B |
| Toluene-IPA | 27:1 | 4.15 | RT→3 | 22/24 | 7.83 | 3.28 | — | B |
| Toluene-EA | 4.2:1 | 4.95 | RT | 26 | 7.27 | 4.0 | — | B + H |
| Toluene-n-BuOH | 20:1 | 4.2 | 3 | 18/25 | 3.34 | 1.76 | B | B |
| Toluene-n-PrOH | 27:1 | 4.15 | 3 | 24/71 | 5.18 | 2.64 | B | B |
| Xylene-EA | 2:1 | 6 | 3 | 23/72 | 9.40 | 3.60 | B | B |
| Heptane-EA | 1:1.3 | 9.2 | RT | 94 | 3.62 | 2.26 | B + Z | B |
| Heptane-EA | 1:1.3 | 9.2 | RT | 25 | 4.36 | 2.24 | B | B |
| Hexane-EA | 1:1.2 | 8.8 | RT | 94 | 5.05 | 2.46 | B | B |
| Hexane-EA | 1:1.2 | 8.8 | RT | 25 | 2.72 | 2.32 | B | B |
| Toluene-acetone | 5.7:1 | 4.7 | 3 | 22/72 | 5.56 | 2.88 | B | B |

Legend:
L/S—liquid/solid ratio (liquid = solvent + anti-solvent);
$^f$symbol RT→3 means that crystallization was started at room temperature then the mixture was cooled to 3° C. to complete precipitation.

Example 7

Preparation of Form Delta (A) This Example Illustrates Preparation of Nateglinide Form Delta by Crystallization from an Ethyl Acetate-Heptane Solvents System Preparation of Nateglinide Form δ

D-Phenylalanine (15.44 g) was added all at once to a 3.5% NaOH solution (370 ml, 3.5 equivalents), at 20° C., under stirring, 230 min$^{-1}$. A clear solution was immediately formed. A neat trans-4-isopropylcyclohexylcarboxychloride (18.03 g) was added for 5 minutes to the reaction solution. A solid was formed and the temperature rose to 32° C. The mixture was stirred for 1 hour at 20° C., under stirring. A 15% H$_2$SO$_4$ (56.1 g) was added all at once to the reaction mixture to adjust the pH to 1-2. The mixture was stirred for 1 h at 20° C. and the solid product was filtered off to afford cake-76 g of a wet product (moisture 65%). The product was dissolved in EA (200 ml), and the aqueous phase was removed. The organic phase was concentrated at 50° C. under reduced pressure to afford 104 g of a turbid solution, containing 95 ml of EA. The solution was filtered and added for 30 minutes to hot heptane (54° C., 250 ml). The initially formed solid completely dissolved after addition of ⅔ of the EA solution. The clear solution was allowed to cool to 25°, seeded with B-form, and left for crystallization overnight, under stirring at 215 revolutions min$^{-1}$. The solid was filtered off and washed with heptane (30 ml). The cake was dried at 60° C./20 mbar to afford 6.84 g of the δ-form. Yield 33%.

Preparation of Nateglinide Form δ

D-Phenylalanine (20.00 g) was added all at once to a 3.5% NaOH solution (370.12 g, 2.7 equivalents), heated to 35° C., under stirring, 200 min$^{-1}$. A clear solution was immediately formed. A neat trans-4-isopropylcyclohexylcarboxychloride (23.3 g) was added all at once to the hot reaction mixture for 1 minute. A turbid solution was formed and the temperature rose to 40° C. The mixture was stirred for 20 minutes at 40-43° C. under stirring. An 85% solution of H$_2$SO$_4$ (11.94 g) was added all at once to the RM to adjust pH 1-2. The solid product was extracted with EA (140 ml). The hot organic extract was washed with warm water (100 ml), followed by brine (25 ml, 30.0 g) at 40° C., and dried with anhydrous magnesium sulfate (3.05 g) over 1.5 hours. The organic solution was filtered through a PTFE 0.45 μm filter, heated to 38° C. and to which was added hot heptane (40° C., 125 ml). The resulting clear solution was gradually cooled for 45 minutes to 13° C. and seeded with NTG in B-form. The crystallization started. The mixture was then cooled for 17 min to 5° C. and stirred for 16 h. The solid was filtered off and washed with a cold (5° C.) mixture of heptane-EA mixture (5:1, total 180 ml) to afford 36.49 g of a wet product (wetness 42.5%). The wet product was dried at 60° C./13 mbar to afford 20.38 g of the product, Form δ, with a purity>99.8%. Yield 55%.

Preparation of Nateglinide Form δ

D-Phenylalanine (20.02 g) was added all at once to a 3.5% NaOH solution (total 410.5 g, 2.99 equivalents), heated to 39° C., under stirring 150 min$^{-1}$. A clear solution was immediately formed. A neat trans-4-isopropylcyclohexylcarboxychloride (24.73 g) was added all at once to the hot reaction mixture. The mixture (clear solution) was stirred for 25 minutes at 44-45° C., under stirring. Ethyl acetate (140 ml), followed by an 85% solution of H$_2$SO$_4$ (14.08 g) were added all at once to the reaction mixture to adjust the pH to 1-2. The hot organic layer was separated, washed twice with water (100 ml) at 30° C., and filtered through a PTFE 0.45 μm filter. The clear solution (141 g) was heated to 46° C. and to which was added hot heptane (46° C., 153 ml), under stirring at 150 min$^{-1}$. The clear solution was gradually cooled to 28° C. and seeded with Form delta. The crystallization occurred at 24° C. The mixture was stirred for 30 minutes at 24° C., gradually cooled to 5° C. and stirred overnight at 5° C. The solid was filtered off and washed with a cold (5° C.) heptane-EA mixture (6:1, total 30 ml) to afford 49.1 g of a wet product in form delta (wetness 50%). The wet product was dried for 24 h at 23° C./20 mbar to afford 24.65 g of the product in a form delta with a purity>99.8%. Yield 65%.

(B) This Example Illustrates the Preparation of Form δ Crystallization

Crude nateglinide (50 grams) was dissolved in ethyl acetate (200 ml) and water (2.5 ml) at 45° C. Hot heptane (260 ml) at 50° C. was added. The mixture was still fully dissolved. The mixture was cooled to 30° C. and seeded with nateglinide Form δ (0.1 grams). The mixture was stirred for 30 minutes and then cooled to less than 10° C. in 2 hours. The mixture was stirred at 5-10° C. overnight and then filtered with vacuum. The wet product was washed with ethyl acetate (100 ml) heptane mixture (ratio 1:3 v/v). The wet product was dried in a vacuum oven at 50° C. overnight. Both the wet and dry samples were Form δ.

Starting material: Wet nateglinide (40% total wetness. 2 ml water, 10 ml ethyl acetate, 21 ml of heptane). Wet crude nateglinide (83 grams) and dry nateglinide (50 grams) were dissolved in ethyl acetate (190 ml) at 45° C. Hot heptane (239 ml) at 50° C. was added. The solution was cooled to 30° C. and a seeded with nateglinide (0.1 grams) Form δ. The mixture was stirred for 30 minutes and then cooled to less than 10° C. in 2 hours. The mixture was stirred at 5-10° C. overnight and then filtered with vacuum. The wet product was washed with ethyl acetate-heptane mixture (100 ml) (ratio 1:3 v/v). The wet product was dried in a vacuum oven at 50° C. overnight. Both the wet and dry samples were Form δ.

(C) This Example Illustrates the Drying of Form δ by Fluidized Bed Dryer

Nateglinide Form delta (10 grams), with about 3% heptane (wt/wt), was dried in a fluidized bed drier for 4 hours at 60° C. Residual heptane was 1578 ppm af. Ethyl acetate is under detection limit. Polymorphic form of the dry product is delta.

According to these procedures, a series of experiments were carried out under various heptane/ethyl ratios, liquid/solid ratios, temperature and seeding. The results are summarized in Table X:

TABLE X

Data on crystallization of NTG in EA-Heptane solvents system

| Seed | Anti-solvent | Ratio v/v | L/S, ml/g | Temperature profile | Yield, % | Form wet | Form dry |
|---|---|---|---|---|---|---|---|
| None | Hexane | 2.7:1 | 11 | 40(1)→20(16) | 58 | Z | B + Z |
| None | Heptane | 4:1 | 16 | 40(1)→20(16) | 64 | Z | B |
| None | Heptane | 5:1 | 11 | 40(1)→20(16) | 74 | H | H |
| None | Heptane | 4.7:1 | 11 | 40(1)→20(16) | 68 | H | H |
| None | Heptane | 7.5: | 11 | 40(1)→20(16) | 48 | B | B |
| None | Heptane | 5:1 | 8 | 40(1)→20(16) | 72 | — | H |
| None | Heptane | 6:1 | 10 | 60(0.1)→20(16) | 76 | B | B |
| None | Heptane | 7.1:1 | 11 | 20(16) | 78 | H | H |
| B | Heptane | 5.1:1 | 14 | 5(1.5)→5(1) | 77 | H | H |
| B | Heptane | 2.5:1 | 16 | 5(2)→5(1) | 74 | H | H |
| B | Heptane | 1:1 | 7.5 | 16→5(16) | 51 | δ | δ |
| B | Heptane | 1:1 | 7 | 30(1)→5(16) | 58 | δ | δ |
| B | Heptane | 1:1 | 7.6 | 13(1)→5(16) | 59 | δ | δ |
| B | Heptane | 1:1 | 7.4 | 13(1)→5(16) | 55 | δ | δ |
| B | Heptane | 2:1 | 9 | 30(0.5)→5(1) | 76 | H + U | — |
|  |  |  |  | 5(1)→5(16) |  | δ | δ |
| B | Heptane | 1.5:1 | 7.5 | 32(0.5)→5 | 71 | U | — |
|  |  |  |  | 5(1) |  | U | — |
|  |  |  |  | 5(1)→5(16) |  | δ | δ |
| None | Heptane | 2:1 | 10 | 31(0.5)→5(4.5) | 67 | δ | δ |
| None | Heptane | 1:1 | — | 9(0.5)→5(1) | — | θ | B |
|  |  |  |  | 5(1)→5(16) |  | δ | δ |
| δ | Heptane | 1:1 | 7.8 | 9(0.5)→5(16) | 46 | δ | δ |
| B | Heptane | 1.1:1 | 6.1 | 25(0.5)→5(16) | 63 | δ | δ |
| δ | Heptane | 1:1 | 7 | 19(0.5)→5(16) | 54 | δ | δ |
| B | Heptane | 1:1 | 7.6 | 13(0.5)→5(16) | 52 | δ | δ |
| δ | Heptane | 1:1 | 6.1 | 30(0.5)→5(16) | 55 | δ | δ |

Temperature profile: crystallization temperature (h)→final temperature (h);
L, t—amount of L, trans-isomer.

Example 8

This Example Illustrates Preparation of Forms of Nateglinide by Precipitation without going to Solution after Combining Preparation of Nateglinide Form U D-Phenylalanine (20.02 g) was added all at once to a 3.5% NaOH solution (369.73 g, 2.7 equivalents), at 20° C., under stirring, 200 revolutions min$^{-1}$. A clear solution was immediately formed. A neat trans-4-isopropylcyclohexylcarboxychloride (23.9 g) was added all at once to the hot reaction solution for 1 minute. A solid was formed and the temperature rose to 32° C. The mixture was stirred for 40 minutes at 20° C., under stirring. An 85% solution of H$_2$SO$_4$ (11.55 g) was added all at once to the reaction mixture to adjust the pH to 1-2. The solid product was extracted with EA (150 ml) at 55° C. for 55 minutes. The hot organic extract was washed with warm water (100 ml), followed by brine (40° C., 50 ml), dried with anhydrous sodium sulfate (10 g) over 1.5 h, and filtered. The excess of EA was removed under reduced pressure to afford 86 g of the solution, containing ~54 g (60 ml) of EA. The EA solution was finally filtered through a PTFE 0.45 μm filter into a clean dropping funnel heated to 35° C. Heptane (320 ml) was placed into the reactor, cooled to 5° C., and seeded with B-form. The clear hot EA-solution was added for 5 minutes to the cold heptane, under stirring. Precipitation immediately happened to afford a solid. The mixture was stirred for 2.5 hours at 5° C. The solid was filtered off and washed with a cold (5° C.) mixture of heptane-EA mixture (4.5:1, total ~120 ml) to afford 63.62 g of a wet product (wetness 54%). The cake (62.4 g) was dried at 60° C./10 mbar to afford 28.6 g of the product, containing ~0.6% of L,trans-isomer (other impurities<0.1%) in the U-form. Yield 77%.

TABLE XI

Data on crystallization of NTG during the crystallization process (precipitation without going into solution after combining)

| Seed | Anti-solvent | Ratio v/v | L/S, ml/g | T$_{EA}$, °C. | T$_{AS}$(time), °C. (h) | Yield, % | L, t, % | Form wet | Form dry |
|---|---|---|---|---|---|---|---|---|---|
| B | Heptane | 3.7:1 | 17 | 25 | 55(25) | 33 | 0.05 | δ | δ |
| None | Heptane | 5.4:1 | 12 | 40 | 5(2.5) | 77 | 0.7 | U | U |
| None | Heptane | 0.77:1 | 9.7 | 45 | 45→25(1) | 71 | 0.01 | B + U |  |
|  |  |  |  |  | 25(1)→25(22) |  | 2 | U | U |
| None | Heptane | 0.8:1 | 9.7 | 45 | 45→25(21) | 72 | 0.03 | σ | σ |

T$_{EA}$—temperature of the EA solution;
T$_{AS}$(time)—temperature of anti-solvent (exposure time)→final temperature (exposure time);
L, t—amount of L, trans-isomer.

Example 9

Heating of Nateglinide Form U

Sample of nateglinide form U (~1 g) was introduced into a 6-gram vial and heated over 8.5 h in a 100° C. oil bath. The vial were extracted from the bath. The resulted sample showed Form U by XRPD.

Sample of nateglinide form U (~0.5 g) was heated to 120° C. for 1 h in an atmospheric pressure. The resulted sample showed Form U by XRPD.

Example 10

Heating of Nateglinide Form δ

Sample of nateglinide form δ (~0.5 g) was heated to 120° C. for 1 h in an atmospheric pressure. The resulted sample showed Form B by XRPD.

Example 11

Preparation of Form Omega

Nateglinide Form delta (5 grams) was dissolved in isopropanol (15 ml) at room temperature. The solution was cooled to ~0° C. Water (6 ml) was added. A white solid precipitated suddenly. The solid was heated to 35° C., resulting in complete dissolution. The solution was cooled to ~7° C. and the product precipitated. The product was filtered with vacuum. XRPD confirmed the presence of Form omega.

Example 12

Drying of a Wet Sample of Form Omega

The product of example 11 was dried at 50° C. in a vacuum oven overnight, and analyzed by XRD. A mixture of Form omega and Form Z was obtained.

Example 13

This Example Illustrates the Preparation of Form U by Triturating Form δ in Ethyl-Acetate Nateglinide Form δ (5 grams) was triturated in ethyl acetate (10 ml) at 25° C. for 2 hours. The wet material was filtered with vacuum and washed with ethyl acetate (10 ml). The wet product was dried at 50° C. in a vacuum oven overnight. The wet and dry products were Form U.

Example 14

This Example Illustrates the Preparation of Form B by Triturating Form δ in Ethyl-Acetate Nateglinide Form δ (5 grams) was triturated in ethyl acetate (10 ml) at 50° C. for 1 hour. The mixture was cooled to 20° C. and triturated for 1 hour. The wet material was filtered with vacuum and washed with ethyl acetate (10 ml). The wet product was dried at 50° C. in a vacuum oven overnight. The wet and dry products were obtained as Form B.

Example 15

Process for the Preparation of Nateglinide Form B

Nateglinide Form B may also be obtained by precipitation of nateglinide Form G, from isopropanol followed by conversion of Form G to Form B. In this embodiment, a form of nateglinide, such as nateglinide Form δ (about 3% LOD) is dissolved in a mixture of IPA/H$_2$O at a preferred temperature range of about 40 to about 50° C. Preferably, the IPA concentration in the solvent mixture is in the range of about 50% to about 70% (v/v), and the volume of the solvent mixture is about 5 to about 20 volumes/unit weight of nateglinide.

The solution obtained after dissolution is preferably cooled to a temperature of about 30° C. for seeding with crystals of Form B. The seeded solution is preferably stirred at the seeding temperature for about 30 minutes to about 3 hours. The solution is preferably then cooled to about 0° C. plus/minus 5° C. for at preferably least about 5 hours, and preferably stirred at 5° C. for at least about 30 minutes. The precipitated nateglinide crystals may be recovered and dried under reduced pressure at a preferred temperature of about 70 to about 90° C. to obtain nateglinide Form B.

In this embodiment, before crystallization, the starting material may optionally be dissolved in IPA or in a IPA/H$_2$O mixture (in the same solvent ratio as the crystallization mixture), followed by evaporation under reduced pressure. After the evaporation, IPA/H$_2$O mixture is fed into the reactor to obtain a solution. Nateglinide Form B is obtained after the evaporation.

The use of EPA allows for the elimination of methyl esters as impurities in the final product as illustrated in FIG. 64.

Example 15 (A)

Nateglinide (40 grams) was dissolved in IPA (240 ml) at 25° C. The solution was filtered to remove insoluble materials. The clear solution was heated to 50° C. and stirred for 5 hours. After stirring, the solvent was evaporated under reduced pressure. The residue was tested by XRD and found to be B type.

Example 15 (B)

Nateglinide (30 grams) was dissolved in IPA (150 ml) in a reactor. The solvent was evaporated under reduced pressure at a jacket temperature Tj=50° C. A solution was obtained by feeding the reactor with IPA (150 ml) and water (150 ml) were fed at Tj=50° C. The clear solution obtained, was cooled to TR=29.4° C., and seeded by B type crystals. The seeded solution was stirred at TR=29.4° C. for additional 3 hours, and afterwards cooled to TR=0° C. for 10 hours. At 0° C., the resulting slurry was stirred for additional 5 hours (overnight). The crystals were isolated and dried under reduced pressure at 90° C. The wet crystals were tested by XRD and found to be G type. The dried crystals were tested by XRD and found to be B type.

Example 15 (C)

Nateglinide (20 grams) was dissolved in EPA (200 ml) in a round bottom flask and the solvent was evaporated under reduced pressure at a temperature of 50° C. IPA (200 ml) and water (200 ml) were fed into the round bottom flask to obtain a clear solution. The solution was transferred to a reactor and cooled to a temperature of TR=28° C. At 28° C., the solution was seeded with type B crystals.

The seeded solution was stirred at 28° C. for an additional 2 hours, and afterwards cooled to 5° C. for 10 hours. At 5° C., the solution was stirred for an additional 4 hours (over-night). The product was isolated and dried under reduced pressure at 90° C. The wet crystals were tested by XRD and found to be G type. The dried crystals were tested by XRD and found to be B type.

Example 16

Process for the Preparation of Nateglinide Form B by Trituration in Water

Nateglinide Form δ was triturated in 5 volumes water at about 25° C. for about 7 hours. The crystals were isolated and dried under reduced pressure at 90° C.

Example (A)

Trituration of Wet Starting Material 50 gr Nateglinide form δ wet (about 37% LOD) was triturated in 250 ml water at 25° C. After 4 hrs trituration, the slurry was sampled and dried under reduced pressure at 90° C. The wet crystals were tested by XRD and found to be δ type. The dry crystals were tested by XRD and found to be B type. After 7 hours of trituration, the product was isolated and dried under reduced pressure at 90° C. The wet crystals were tested by XRD and found to be δ type. The dry crystals were tested by XRD and found to be B type.

Example (B)

Trituration of Dry Starting Material 50 gr Nateglinide form δ dry was triturated in 250 ml water at 25° C. After 4.5 hrs trituration, the slurry was sampled and dried under reduced pressure at 90° C. The wet crystals were tested by XRD and found to be Z type. The dry crystals were tested by XRD and found to be B type. After 7.5 hours of trituration, the product was isolated and dried under reduced pressure at 90° C. The wet crystals were tested by XRD and found to be E type. The dry crystals were tested by XRD and found to be B type.

Example 17

Preparation of Nateglinide Form U

Example (A)

Crystallization from Acetone

Nateglinide (50 grams) Form δ was dissolved in acetone (175 ml) at 42° C. The clear solution was cooled to 10° C. for seeding. After seeding with type B crystals, the seeded solution was stirred for an additional 3 hours at a temperature of 10° C. and cooled to −10° C. for 10 hours, and stirred at −10° C. over night. The crystals were isolated and dried at 90° C. The wet crystals were tested by XRD and found to be U type. The dry crystals were tested and found to be U type.

Example (B)

Crystallization from Ethyl Acetate

Nateglinide (20 grams) were dissolved in ethyl acetate (560 ml) at 40° C. The solution was filtered to remove insoluble matter. The clear solution was evaporated under reduced pressure, and Ethyl Acetate (460 ml) was evaporated (the solvent volume in the reactor was 5 volumes/unit weight Nateglinide). The solution was cooled to 20° C. and seeded with type B crystals. The seeded solution was stirred at 20° C. for an additional 30 minutes, cooled to 0° C. for 1.5 hours, and stirred at 0° C. for an additional 30 minutes. The crystals were isolated and dried under reduced pressure at 30° C., 50° C., 90° C. The wet crystals were tested by XRD and found to be U type. The dry crystals were tested by XRD and found to be U type.

Example 18

Removal of Residual Solvent from Form Delta

Nateglinide (40 grams) Form delta (1.5% heptane) was dried in a stirred reactor (7-10 rpm) under 60 mmHg vacuum and at 60° C. After 6 hours of drying, the residual solvent of the material was 613 ppm of heptane. The polymorph of the dried material remained delta form, as the starting material.

Example 19

Preparation of Nateglinide Form B from Ethyl Acetate

Nateglinide form δ is dissolved in ethyl acetate at 25° C. The solvent is evaporated under reduced pressure, until turbidity appears. The turbid solution is cooled to 0° C. plus/minus 5° C. for 1 hour and stirred for 1 hour. The product was isolated and dried under reduced pressure at 50° C.

Example (A)

Nateglinide (12 grams) Form δ was dissolved in 165 ml of ethyl acetate at 25° C. The solvent was evaporated under reduced pressure at 25° C., until turbidity appeared. At the end of evaporation, the volume in the reactor was 90-95 ml. The mixture was cooled from 25° C. to 5° C. for 1 hour and stirred at 5° C. for 1 hour. The product was isolated and dried under reduced pressure at 50° C. Both the wet and the dry crystals were tested by XRD and DSC and found to be B type.

Having thus described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 may be used as a guidance. All references mentioned herein are incorporated in their entirety.

What is claimed is:

1. A process for preparing crystalline form of nateglinide having an XRPD pattern with peaks at 4.7, 7.4, 13.8 and 17.0+/−0.2 theta comprising the steps of:
   a) preparing a solution of nateglinide in ethylacetate;
   b) seeding the solution with nateglinide crystals; and
   c) recovering the crystalline form as a precipitate.
2. The process of claim 1, where the volume of ethyl acetate compared to weight of nateglinide is about 3 to about 11 mL/g.
3. The process of claim 2, where the volume of ethyl acetate compared to weight of nateglinide is about 4 to about 6 mL/g.
4. The process of claim 1, wherein the solution is seeded with the same crystalline form.
5. The process of claim 4, further comprising the step of cooling before or after seeding.

6. The process of claim 1, wherein the nateglinide obtained is more than about 99% pure as area percentage HPLC.

7. The process of claim 1, wherein nateglinide obtained is 99% free of other crystalline forms by weight.

8. A process for preparing crystalline form of nateglinide having an XRPD pattern with peaks at 4.7, 7.4, 13.8 and 17.0+/−0.2 theta comprising the steps of:
a) preparing a container holding a solution of nateglinide in ethyl acetate;
b) adding a $C_5$ to $C_{12}$ hydrocarbon to the container holding the solution;
c) recovering the crystalline form as a precipitate.

9. The process of claim 8, wherein the hydrocarbon is a $C_5$ to $C_8$ hydrocarbon.

10. The process of claim 9, wherein the hydrocarbon is heptane.

11. The process of claim 8, wherein precipitation is carried out in the presence of water.

12. The process of claim 8, further comprising seeding before precipitation.

13. The process of claim 12, wherein the same crystalline form is used for seeding.

14. The process of claim 8, wherein the hydrocarbon is added in such manner to avoid precipitation upon addition.

15. A process for preparing crystalline form of nateglinide having an XRPD pattern with peaks at 4.7, 7.4, 13.8 and 17.0+/−0.2 theta comprising the steps of:
a) preparing a container holding a solution of nateglinide in ethyl acetate;
b) adding heptane to the container holding the solution in such manner to avoid precipitation upon addition;
c) cooling the solution and seeding the solution with the same crystalline form of nateglinide, in any order; and
d) filtering the crystalline nateglinide as a precipitate.

16. The process of claim 15, wherein the ethyl acetate is mixed with water at about 2% to about 10% water as percentage of milliliters of water to grams of nateglinide.

17. A process for preparing crystalline form of nateglinide having an XRPD pattern with peaks at 4.7, 7.4, 13.8 and 17.0+/−0.2 theta comprising the steps of:
a) preparing a solution of nateglinide in a mixture of water and ethyl acetate;
b) combining the solution with an anti-solvent; and
c) recovering the crystalline nateglinide as a precipitate.

18. The process of claim 17, wherein the anti-solvent is a $C_5$ to $C_{12}$ hydrocarbon.

19. The process of claim 18, wherein the hydrocarbon is heptane.

20. The process of claim 17, further comprising seeding before precipitation.

21. The process of claim 20, wherein the same crystalline form is used for seeding.

22. The process of claim 17, wherein the anti-solvent is added in such manner to avoid precipitation upon addition.

23. A process for purifying crystalline form of nateglinide having an XRPD pattern with peaks at 4.7, 7.4, 13.8 and 17.0+/−0.2 theta comprising the step of crystallizing the crystalline nateglinide from a solution in the presence of water, thereby resulting in the crystalline form being 99% pure as area percentage HPLC.

24. The process of claim 23, wherein ratio of water to nateglinide is about 2% to about 10% as percentage of milliliters of water to grams of nateglinide.

25. The process of claim 23, wherein the rest of the solution is comprised of ethyl acetate.

26. A process for preparing crystalline form of nateglinide having an XRPD pattern with peaks at 4.7, 7.4, 13.8 and 17.0+/−0.2 theta comprising the steps of:
a) preparing a solution of nateglinide in ethyl acetate at a temperature of about 25° C. to about 50° C. at an ethyl acetate/nateglinide ratio of about 3 to about 11 ml/g;
b) seeding the solution with the same crystalline nateglinide at a temperature of about 10° C. to about 35° C.;
c) stirring the seeded solution;
d) cooling the seeded solution at a rate of about 1° C. to 10° C. per hour to a temperature of about negative 10° C. to about 10° C.; and
e) filtering the crystalline nateglinide as a precipitate; and
f) drying the precipitate.

27. A crystalline form of nateglinide characterized by an XRPD pattern with peaks at 4.7, 7.4, 13.8 and 17.0+/−0.2 theta, wherein the crystalline form has less intensity for a peak at 3.8+/−0.2 theta than the intensity for each of the peaks at 4.7, 7.4, 13.8 and 17.0+/−0.2 theta.

28. The crystalline form of claim 27, wherein the crystalline form is 99% pure as area percentage HPLC.

29. The crystalline form of claim 27, wherein crystalline form is obtained 99% free of other crystalline forms by weight.

30. A crystalline form of nateglinide characterized by an XRPD pattern or an FTIR spectrum as substantially depicted in a figure selected from the group consisting of FIG. 31, FIG. 65, FIG. 66, FIG. 67, FIG. 68 and FIG. 69, wherein peaks in the XRPD patterns have a variation of +/−0.2 theta.

31. A crystalline form of nateglinide characterized by an XRPD pattern with peaks consisting essentially of 4.7, 7.4, 13.8 and 17.0+/−0.2 theta.

32. A crystalline form of nateglinide, characterized by an XRPD pattern with peaks at 4.7, 7.4, 13.8 and 17.0+/−0.2 theta, prepared by the process of claim 8.

33. A crystalline form of nateglinide, characterized by an XRPD pattern with peaks at 4.7, 7.4, 13.8 and 17.0+/−0.2 theta, prepared by the process of claim 15.

34. A crystalline form of nateglinide, characterized by an XRPD pattern with peaks at 4.7, 7.4, 13.8 and 17.0+/−0.2 theta, prepared by the process of claim 17.

35. A crystalline form of nateglinide, characterized by an XRPD pattern with peaks at 4.7, 7.4, 13.8 and 17.0+/−0.2 theta, prepared by the process of claim 23.

36. A crystalline form of nateglinide, characterized by an XRPD pattern with peaks at 4.7, 7.4, 13.8 and 17.0+/−0.2 theta, prepared by the process of claim 26.

* * * * *